United States Patent
Davidson

(10) Patent No.: US 10,905,750 B2
(45) Date of Patent: Feb. 2, 2021

(54) GRP78 ANTAGONIST THAT BLOCK BINDING OF RECEPTOR TYROSINE KINASE ORPHAN RECEPTORS AS IMMUNOTHERAPY ANTICANCER AGENTS

(71) Applicant: CREATIVE BIOTHERAPEUTICS, LLC, Gurnee, IL (US)

(72) Inventor: Donald J. Davidson, Gurnee, IL (US)

(73) Assignees: Donald J. Davidson, Gurnee, IL (US); Creative BioTherapeutics, Gurnee, IL (US)

( * ) Notice: Subject to any disclaimer, the term of this patent is extended or adjusted under 35 U.S.C. 154(b) by 0 days.

(21) Appl. No.: 16/184,247

(22) Filed: Nov. 8, 2018

(65) Prior Publication Data
US 2019/0142913 A1    May 16, 2019

Related U.S. Application Data

(60) Provisional application No. 62/584,564, filed on Nov. 10, 2017.

(51) Int. Cl.
| | |
|---|---|
| *A61K 38/00* | (2006.01) |
| *A61K 38/49* | (2006.01) |
| *A61P 35/00* | (2006.01) |
| *A61K 47/68* | (2017.01) |

(52) U.S. Cl.
CPC .......... *A61K 38/49* (2013.01); *A61K 47/6811* (2017.08); *A61K 47/6849* (2017.08); *A61K 47/6851* (2017.08); *A61P 35/00* (2018.01); *C07K 2319/30* (2013.01); *C07K 2319/32* (2013.01)

(58) Field of Classification Search
None
See application file for complete search history.

(56) References Cited

U.S. PATENT DOCUMENTS

| | | | |
|---|---|---|---|
| 7,495,068 B2 | 2/2009 | Davidson et al. | |
| 7,741,286 B2 | 6/2010 | Bridon et al. | |
| 9,933,434 B2 | 4/2018 | Kipps et al. | |
| 9,938,350 B2 | 4/2018 | Kipps et al. | |
| 2008/0318212 A1* | 12/2008 | Wilson | C12Q 1/6886 435/6.14 |
| 2009/0239850 A1* | 9/2009 | Cance | A61K 31/17 514/222.2 |
| 2010/0015128 A1* | 1/2010 | Lee | A61P 35/00 424/130.1 |

OTHER PUBLICATIONS

Caty Casas; "GRP78 at the Centre of the Stage in Cancer and Neuroprotection", Frontiers in Neuroscience, Apr. 2017, vol. 11, Article 177; 15 pages.

Mohammed Hojjat-Farsangi, et al; "Spontaneous Immunity Against the Receptor Tyrosine Kinase ROR1 in Patients with Chronic Lymphocytic Leukemia", PLOS ONE; Nov. 12, 2015, 10(11), 15 pages.

Allessandra Gentile, et al; "Ror1 Is a Pseudokinase That is Crucial for Met-Driven Tumorigenesis", Cancer Res. 71 Apr. 15, 2011, pp. 3132-3141; Published Onine First Apr. 12, 2011.

Allessandra Gentile, et al; "The ROR1 pseudokinase diversifies signaling outputs in MET-addicted cancer cells", International Journal of Cancer, Nov. 15, 2014;135(10), pp. 2305-2316; Epub Apr. 15, 2014.

Eun-Hwa, Jung, et al; "Targeting ROR1 inhibits the self-renewal and invasive ability of glioblastoma stem cells", Cell Biochemistry and Function, 34; 149-157, Published online Feb. 28, 2016 in Wiley Online Library.

Bo Ram Kang, et al; "Cell surface GRP78 as a biomarker and target for suppressing glioma cells", Scientific Reports, Oct. 7, 2016, 7 pages.

Hae Kyung Lee, et al; "GRP78 is overexpressed in glioblastomas and regulates glioma cell growth and apoptosis", Neuro-Oncology; Jun. 10, 2008; 10(3): 236-243.

Zongwei Li, et al; "Glucose regulated protein 78: A critical link between tumor microenvironment and cancer hallmarks", Biochimica et Biophysica Acta; Available online Mar. 9, 2012; 10 pages.

Sabrina R. Perri, et al; "Plasminogen Kringle 5 blocks tumor progression by antiangiogenic and proinflammatory pathways", Mol Cancer Ther Feb. 2007, 6(2): 441-9.

Zachary Rosenes, et al; "The Anti-Cancer IgM Monoclonal Antibody PAT-SM6 Binds with High Avidity to the Unfolded Protein Response Regulator GRP78", PLOS ONE, Sep. 2012, vol. 7, Issue 9, 11 pages.

Muyang Yang, et al; "Glucose-Regulated Protein 78-Induced Myeloid Antigen-Presenting Cells Maintained Tolerogenic Signature upon LPS Stimulation", Frontiers in Immunology, Dec. 2016, vol. 7, Article 552, 12 pages.

Suping Zhang, et al; "ROR1 Is Expressed in Human Breast Cancer and Associated with Enhanced Tumor-Cell Growth", PLOS ONE, Mar. 2012, vol. 7, Issue 3,12 pages.

* cited by examiner

*Primary Examiner* — Jeanette M Lieb

(57) ABSTRACT

Glucose-regulated protein (GRP78) antagonists that block, interfere, and/or inhibit binding of receptor tyrosine kinase orphan receptors (RORs) are described for use as immunotherapy anticancer. These GRP78 antagonists inhibit surface bound GRP78 binding and receptor signaling and are believed to mimic the behavior of anti-angiogenic kringles found in mammalian plasminogen and in receptor tyrosine kinase orphan receptors. These GRP78 antagonist may be free peptide fragments, or peptide fragments covalently fused to blood borne proteins such as albumin or immunoglobins, or modified peptide fragments that a designed to bind to blood or tissue peptides when introduced in vivo into the blood stream of a patient.

3 Claims, 25 Drawing Sheets
(16 of 25 Drawing Sheet(s) Filed in Color)
Specification includes a Sequence Listing.

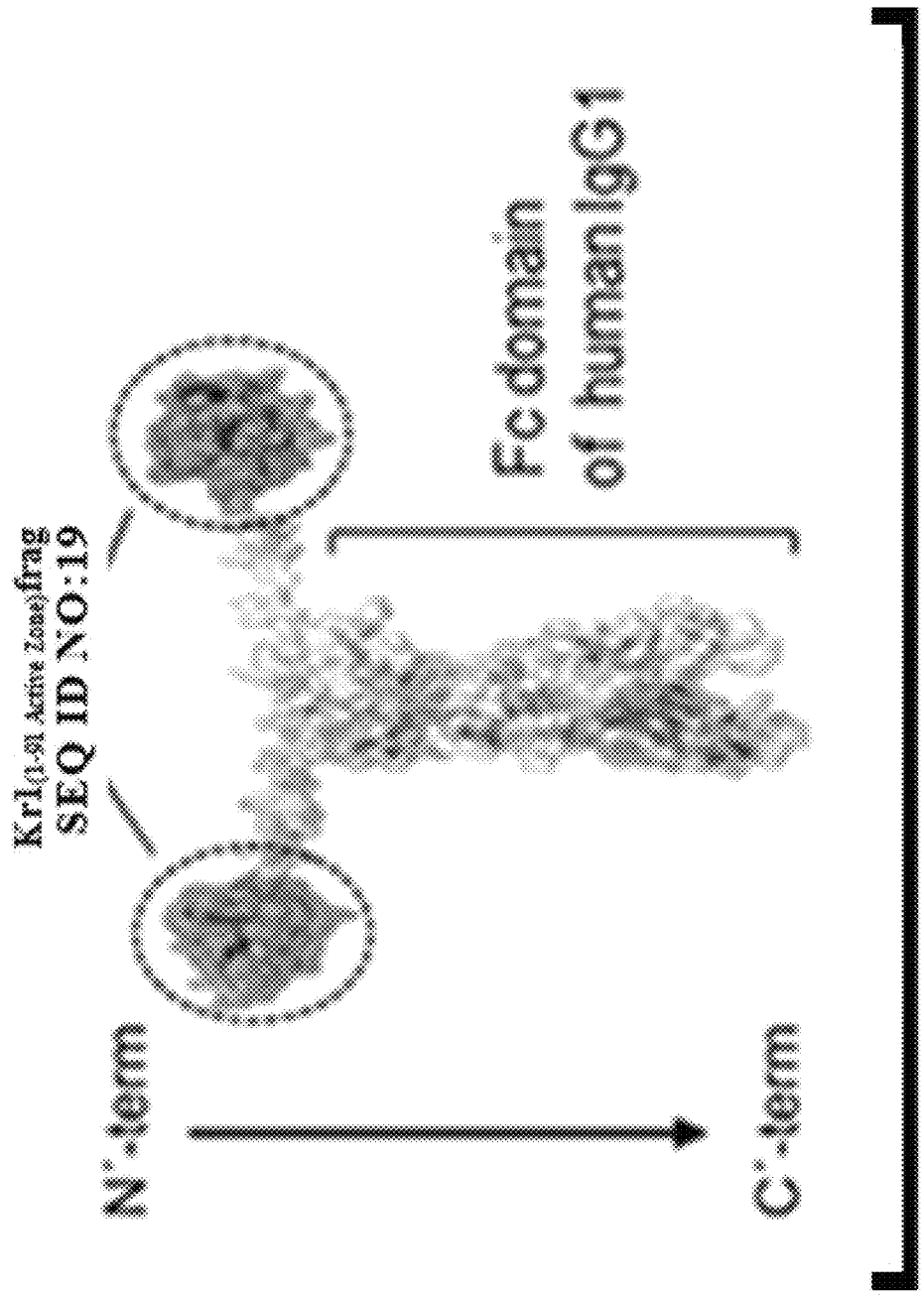

SEQUENCE LISTING

```
<160> NUMBER OF SEQ ID NOS: 189

<210> SEQ ID NO 1
<211> LENGTH: 89
<212> TYPE: PRT
<213> ORGANISM: Artificial Sequence
<220> FEATURE:
<223> OTHER INFORMATION: Synthetic Peptide
      K5(3-89 Active Zone)

<400> SEQUENCE: 1

Ser Glu Glu Asp Cys Met Phe Gly Asn Gly Lys Gly Tyr Arg Gly Lys
1               5                   10                  15

Arg Ala Thr Thr Val Thr Gly Thr Pro Cys Gln Asp Trp Ala Ala Gln
            20                  25                  30

Glu Pro His Arg His Ser Ile Phe Thr Pro Glu Thr Asn Pro Arg Ala
        35                  40                  45

Gly Leu Glu Lys Asn Tyr Cys Arg Asn Pro Asp Gly Asp Val Gly Gly
    50                  55                  60

Pro Trp Cys Tyr Thr Thr Asn Pro Arg Lys Leu Tyr Asp Tyr Cys Asp
65                  70                  75                  80

Val Pro Gln Cys Ala Ala Pro Lys Ser
                85

<210> SEQ ID NO 2
<211> LENGTH: 317
<212> TYPE: PRT
<213> ORGANISM: Artificial Sequence
<220> FEATURE:
<223> OTHER INFORMATION: Synthetic Peptide
      K5(3-89 Active Zone)frag-Fc

<400> SEQUENCE: 2

Ser Glu Glu Asp Cys Met Phe Gly Asn Gly Lys Gly Tyr Arg Gly Lys
1               5                   10                  15

Arg Ala Thr Thr Val Thr Gly Thr Pro Cys Gln Asp Trp Ala Ala Gln
            20                  25                  30

Glu Pro His Arg His Ser Ile Phe Thr Pro Glu Thr Asn Pro Arg Ala
        35                  40                  45

Gly Leu Glu Lys Asn Tyr Cys Arg Asn Pro Asp Gly Asp Val Gly Gly
    50                  55                  60

Pro Trp Cys Tyr Thr Thr Asn Pro Arg Lys Leu Tyr Asp Tyr Cys Asp
65                  70                  75                  80

Val Pro Gln Cys Ala Ala Pro Lys Ser Cys Asp Lys Thr His Thr Cys
                85                  90                  95

Pro Pro Cys Pro Ala Pro Glu Leu Leu Gly Gly Pro Ser Val Phe Leu
                100                 105                 110

Phe Pro Pro Lys Pro Lys Asp Thr Leu Met Ile Ser Arg Thr Pro Glu
            115                 120                 125

Val Thr Cys Val Val Val Asp Val Ser His Glu Asp Pro Glu Val Lys
        130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
```

```
                    165                 170                 175
Thr Val Leu His Gln Asp Trp Leu Asn Gly Lys Glu Tyr Lys Cys Lys
            180                 185                 190

Val Ser Asn Lys Ala Leu Pro Ala Pro Ile Glu Lys Thr Ile Ser Lys
        195                 200                 205

Ala Lys Gly Gln Pro Arg Glu Pro Gln Val Tyr Thr Leu Pro Pro Ser
    210                 215                 220

Arg Asp Glu Leu Thr Lys Asn Gln Val Ser Leu Thr Cys Leu Val Lys
225                 230                 235                 240

Gly Phe Tyr Pro Ser Asp Ile Ala Val Glu Trp Glu Ser Asn Gly Gln
            245                 250                 255

Pro Glu Asn Asn Tyr Lys Thr Thr Pro Pro Val Leu Asp Ser Asp Gly
        260                 265                 270

Ser Phe Phe Leu Tyr Ser Lys Leu Thr Val Asp Lys Ser Arg Trp Gln
    275                 280                 285

Gln Gly Asn Val Phe Ser Cys Ser Val Met His Glu Ala Leu His Asn
290                 295                 300

His Tyr Thr Gln Lys Ser Leu Ser Leu Ser Pro Gly Lys
305                 310                 315

<210> SEQ ID NO 3
<211> LENGTH: 254
<212> TYPE: PRT
<213> ORGANISM: Artificial Sequence
<220> FEATURE:
<223> OTHER INFORMATION: Synthetic Peptide
      K5(57-81 Active Zone)frag -Fc

<400> SEQUENCE: 3

Arg Asn Pro Asp Gly Asp Val Gly Gly Pro Trp Cys Tyr Thr Thr Asn
1               5                   10                  15

Pro Arg Lys Leu Tyr Asp Tyr Cys Lys Ser Cys Asp Lys Thr His Thr
            20                  25                  30

Cys Pro Pro Cys Pro Ala Pro Glu Leu Leu Gly Gly Pro Ser Val Phe
        35                  40                  45

Leu Phe Pro Pro Lys Pro Lys Asp Thr Leu Met Ile Ser Arg Thr Pro
    50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
            85                  90                  95

Lys Pro Arg Glu Glu Gln Tyr Asn Ser Thr Tyr Arg Val Val Ser Val
        100                 105                 110

Leu Thr Val Leu His Gln Asp Trp Leu Asn Gly Lys Glu Tyr Lys Cys
    115                 120                 125

Lys Val Ser Asn Lys Ala Leu Pro Ala Pro Ile Glu Lys Thr Ile Ser
130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
            165                 170                 175

Lys Gly Phe Tyr Pro Ser Asp Ile Ala Val Glu Trp Glu Ser Asn Gly
        180                 185                 190

Gln Pro Glu Asn Asn Tyr Lys Thr Thr Pro Pro Val Leu Asp Ser Asp
    195                 200                 205
```

```
Gly Ser Phe Phe Leu Tyr Ser Lys Leu Thr Val Asp Lys Ser Arg Trp
            210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 4
<211> LENGTH: 254
<212> TYPE: PRT
<213> ORGANISM: Artificial Sequence
<220> FEATURE:
<223> OTHER INFORMATION: Synthetic Peptide
      K5(57-81 Active Zone w Ala sub Cys)frag -Fc

<400> SEQUENCE: 4

Arg Asn Pro Asp Gly Asp Val Gly Gly Pro Trp Ala Tyr Thr Thr Asn
1               5                   10                  15

Pro Arg Lys Leu Tyr Asp Tyr Ala Lys Ser Cys Asp Lys Thr His Thr
            20                  25                  30

Cys Pro Pro Cys Pro Ala Pro Glu Leu Leu Gly Gly Pro Ser Val Phe
            35                  40                  45

Leu Phe Pro Pro Lys Pro Lys Asp Thr Leu Met Ile Ser Arg Thr Pro
50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
            115                 120                 125

Lys Val Ser Asn Lys Ala Leu Pro Ala Pro Ile Glu Lys Thr Ile Ser
130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
            195                 200                 205

Gly Ser Phe Phe Leu Tyr Ser Lys Leu Thr Val Asp Lys Ser Arg Trp
            210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 5
<211> LENGTH: 254
<212> TYPE: PRT
<213> ORGANISM: Artificial Sequence
<220> FEATURE:
<223> OTHER INFORMATION: Synthetic Peptide
      K5(57-81 Active Zone w Val sub Cys)frag-Fc

<400> SEQUENCE: 5
```

Arg Asn Pro Asp Gly Asp Val Gly Gly Pro Trp Val Tyr Thr Thr Asn
1               5                   10                  15

Pro Arg Lys Leu Tyr Asp Tyr Val Lys Ser Cys Asp Lys Thr His Thr
            20                  25                  30

Cys Pro Pro Cys Pro Ala Pro Glu Leu Leu Gly Gly Pro Ser Val Phe
            35                  40                  45

Leu Phe Pro Pro Lys Pro Lys Asp Thr Leu Met Ile Ser Arg Thr Pro
    50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
            115                 120                 125

Lys Val Ser Asn Lys Ala Leu Pro Ala Pro Ile Glu Lys Thr Ile Ser
            130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
            195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 6
<211> LENGTH: 254
<212> TYPE: PRT
<213> ORGANISM: Artificial Sequence
<220> FEATURE:
<223> OTHER INFORMATION: Synthetic Peptide
      K5(57-81 Active Zone w Ile sub Cys)frag-Fc

<400> SEQUENCE: 6

Arg Asn Pro Asp Gly Asp Val Gly Gly Pro Trp Ile Tyr Thr Thr Asn
1               5                   10                  15

Pro Arg Lys Leu Tyr Asp Tyr Ile Lys Ser Cys Asp Lys Thr His Thr
            20                  25                  30

Cys Pro Pro Cys Pro Ala Pro Glu Leu Leu Gly Gly Pro Ser Val Phe
            35                  40                  45

Leu Phe Pro Pro Lys Pro Lys Asp Thr Leu Met Ile Ser Arg Thr Pro
    50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

```
Leu Thr Val Leu His Gln Asp Trp Leu Asn Gly Lys Glu Tyr Lys Cys
            115                 120                 125

Lys Val Ser Asn Lys Ala Leu Pro Ala Pro Ile Glu Lys Thr Ile Ser
        130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 7
<211> LENGTH: 254
<212> TYPE: PRT
<213> ORGANISM: Artificial Sequence
<220> FEATURE:
<223> OTHER INFORMATION: Synthetic Peptide
      K5(57-81 Active Zone w Leu sub Cys)frag-Fc

<400> SEQUENCE: 7

Arg Asn Pro Asp Gly Asp Val Gly Gly Pro Trp Leu Tyr Thr Thr Asn
1               5                   10                  15

Pro Arg Lys Leu Tyr Asp Tyr Leu Lys Ser Cys Asp Lys Thr His Thr
                20                  25                  30

Cys Pro Pro Cys Pro Ala Pro Glu Leu Leu Gly Gly Pro Ser Val Phe
            35                  40                  45

Leu Phe Pro Pro Lys Pro Lys Asp Thr Leu Met Ile Ser Arg Thr Pro
50                  55                  60

Glu Val Thr Cys Val Val Val As

```
                        210                 215                 220
Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 8
<211> LENGTH: 250
<212> TYPE: PRT
<213> ORGANISM: Artificial Sequence
<220> FEATURE:
<223> OTHER INFORMATION: Synthetic Peptide
      K5(70-89 Active Zone)frag-Fc

<400> SEQUENCE: 8

Tyr Thr Thr Asn Pro Arg Lys Leu Tyr Asp Tyr Cys Asp Val Pro Gln
1               5                   10                  15

Cys Ala Ala Pro Lys Ser Cys Asp Lys Thr His Thr Cys Pro Pro Cys
            20                  25                  30

Pro Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 9
<211> LENGTH: 250
<212> TYPE: PRT
<213> ORGANISM: Artificial Sequence
<220> FEATURE:
<223> OTHER INFORMATION: Synthetic Peptide
      K5(70-89 Active Zone with Ala sub Cys)frag-Fc

<400> SEQUENCE: 9

Tyr Thr Thr Asn Pro Arg Lys Leu Tyr Asp Tyr Ala Asp Val Pro Gln
```

```
                1               5                      10                     15
            Ala Ala Ala Pro Lys Ser Cys Asp Lys Thr His Thr Cys Pro Pro Cys
                            20                  25                  30

Pro Ala Pro Glu Leu Leu Gly Gly Pro Ser Val Phe Leu Phe Pro Pro
                            35                  40                  45

Lys Pro Lys Asp Thr Leu Met Ile Ser Arg Thr Pro Glu Val Thr Cys
                        50                  55                  60

Val Val Val Asp Val Ser His Glu Asp Pro Glu Val Lys Phe Asn Trp
            65                  70                  75                  80

Tyr Val Asp Gly Val Glu Val His Asn Ala Lys Thr Lys Pro Arg Glu
                            85                  90                  95

Glu Gln Tyr Asn Ser Thr Tyr Arg Val Val Ser Val Leu Thr Val Leu
                            100                 105                 110

His Gln Asp Trp Leu Asn Gly Lys Glu Tyr Lys Cys Lys Val Ser Asn
                        115                 120                 125

Lys Ala Leu Pro Ala Pro Ile Glu Lys Thr Ile Ser Lys Ala Lys Gly
                    130                 135                 140

Gln Pro Arg Glu Pro Gln Val Tyr Thr Leu Pro Pro Ser Arg Asp Glu
            145                 150                 155                 160

Leu Thr Lys Asn Gln Val Ser Leu Thr Cys Leu Val Lys Gly Phe Tyr
                            165                 170                 175

Pro Ser Asp Ile Ala Val Glu Trp Glu Ser Asn Gly Gln Pro Glu Asn
                        180                 185                 190

Asn Tyr Lys Thr Thr Pro Pro Val Leu Asp Ser Asp Gly Ser Phe Phe
                        195                 200                 205

Leu Tyr Ser Lys Leu Thr Val Asp Lys Ser Arg Trp Gln Gln Gly Asn
                    210                 215                 220

Val Phe Ser Cys Ser Val Met His Glu Ala Leu His Asn His Tyr Thr
            225                 230                 235                 240

Gln Lys Ser Leu Ser Leu Ser Pro Gly Lys
                            245                 250

<210> SEQ ID NO 10
<211> LENGTH: 250
<212> TYPE: PRT
<213> ORGANISM: Artificial Sequence
<220> FEATURE:
<223> OTHER INFORMATION: Synthetic Peptide
      K5(70-89 Active Zone with Val sub Cys)frag-Fc

<400> SEQUENCE: 10

Tyr Thr Thr Asn Pro Arg Lys Leu Tyr Asp Tyr Val Asp Val Pro Gln
            1               5                   10                  15

Val Ala Ala Pro Lys Ser Cys Asp Lys Thr His Thr Cys Pro Pro Cys
                            20                  25                  30

Pro Ala Pro Glu Leu Leu Gly Gly Pro Ser Val Phe Leu Phe Pro Pro
                            35                  40                  45

Lys Pro Lys Asp Thr Leu Met Ile Ser Arg Thr Pro Glu Val Thr Cys
                        50                  55                  60

Val Val Val Asp Val Ser His Glu Asp Pro Glu Val Lys Phe Asn Trp
            65                  70                  75                  80

Tyr Val Asp Gly Val Glu Val His Asn Ala Lys Thr Lys Pro Arg Glu
                            85                  90                  95

Glu Gln Tyr Asn Ser Thr Tyr Arg Val Val Ser Val Leu Thr Val Leu
                            100                 105                 110
```

-continued

```
His Gln Asp Trp Leu Asn Gly Lys Glu Tyr Lys Cys Lys Val Ser Asn
            115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 11
<211> LENGTH: 250
<212> TYPE: PRT
<213> ORGANISM: Artificial Sequence
<220> FEATURE:
<223> OTHER INFORMATION: Synthetic Peptide
      K5(70-89 Active Zone with Ile sub Cys)frag-Fc

<400> SEQUENCE: 11

Tyr Thr Thr Asn Pro Arg Lys Leu Tyr Asp Tyr Ile Asp Val Pro Gln
1               5                   10                  15

Ile Ala Ala Pro Lys Ser Cys Asp Lys Thr His Thr Cys Pro Pro Cys
            20                  25                  30

Pro Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
    130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220
```

```
Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 12
<211> LENGTH: 250
<212> TYPE: PRT
<213> ORGANISM: Artificial Sequence
<220> FEATURE:
<223> OTHER INFORMATION: Synthetic Peptide
      K5(70-89 Active Zone with Leu sub Cys)frag-Fc

<400> SEQUENCE: 12

Tyr Thr Thr Asn Pro Arg Lys Leu Tyr Asp Tyr Leu Asp Val Pro Gln
1               5                   10                  15

Leu Ala Ala Pro Lys Ser Cys Asp Lys Thr His Thr Cys Pro Pro Cys
                20                  25                  30

Pro Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 13
<211> LENGTH: 246
<212> TYPE: PRT
<213> ORGANISM: Artificial Sequence
<220> FEATURE:
<223> OTHER INFORMATION: Synthetic Peptide
      K5(74-89 Active Zone)frag-Fc

<400> SEQUENCE: 13

Pro Arg Lys Leu Tyr Asp Tyr Cys Asp Val Pro Gln Cys Ala Ala Pro
1               5                   10                  15
```

```
Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 14
<211> LENGTH: 246
<212> TYPE: PRT
<213> ORGANISM: Artificial Sequence
<220> FEATURE:
<223> OTHER INFORMATION: Synthetic Peptide
      K5(74-89 Active Zone w Ala sub Cys)frag-Fc

<400> SEQUENCE: 14

Pro Arg Lys Leu Tyr Asp Tyr Ala Asp Val Pro Gln Ala Ala Ala Pro
1               5                   10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
```

```
            115                 120                 125
Ala Pro Ile Glu Lys Thr Ile Ser Lys Ala Lys Gly Gln Pro Arg Glu
        130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 15
<211> LENGTH: 246
<212> TYPE: PRT
<213> ORGANISM: Artificial Sequence
<220> FEATURE:
<223> OTHER INFORMATION: Synthetic Peptide
      K5(74-89 Active Zone w Val sub Cys)frag-Fc

<400> SEQUENCE: 15

Pro Arg Lys Leu Tyr Asp Tyr Val Asp Val Pro Gln Val Ala Ala Pro
1               5                   10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220
```

Ser Val Met His Glu Ala Leu His Asn His Tyr Thr Gln Lys Ser Leu
225                 230                 235                 240

Ser Leu Ser Pro Gly Lys
                245

<210> SEQ ID NO 16
<211> LENGTH: 246
<212> TYPE: PRT
<213> ORGANISM: Artificial Sequence
<220> FEATURE:
<223> OTHER INFORMATION: Synthetic Peptide
      K5(74-89 Active Zone w Ile sub Cys)frag-Fc

<400> SEQUENCE: 16

Pro Arg Lys Leu Tyr Asp Tyr Ile Asp Val Pro Gln Ile Ala Ala Pro
1               5                   10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 17
<211> LENGTH: 246
<212> TYPE: PRT
<213> ORGANISM: Artificial Sequence
<220> FEATURE:
<223> OTHER INFORMATION: Synthetic Peptide
      K5(74-89 Active Zone w Leu sub Cys)frag-Fc

<400> SEQUENCE: 17

Pro Arg Lys Leu Tyr Asp Tyr Leu Asp Val Pro Gln Leu Ala Ala Pro
1               5                   10                  15

Lys Ser Cys Asp Lys Thr His Thr Cys Pro Pro Cys Pro Ala Pro Glu
              20                  25                  30

Leu Leu Gly Gly Pro Ser Val Phe Leu Phe Pro Lys Pro Lys Asp
         35                  40                  45

Thr Leu Met Ile Ser Arg Thr Pro Glu Val Thr Cys Val Val Val Asp
 50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
              85                  90                  95

Ser Thr Tyr Arg Val Val Ser Val Leu Thr Val Leu His Gln Asp Trp
             100                 105                 110

Leu Asn Gly Lys Glu Tyr Lys Cys Lys Val Ser Asn Lys Ala Leu Pro
             115                 120                 125

Ala Pro Ile Glu Lys Thr Ile Ser Lys Ala Lys Gly Gln Pro Arg Glu
         130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                 165                 170                 175

Ala Val Glu Trp Glu Ser Asn Gly Gln Pro Glu Asn Asn Tyr Lys Thr
             180                 185                 190

Thr Pro Pro Val Leu Asp Ser Asp Gly Ser Phe Phe Leu Tyr Ser Lys
         195                 200                 205

Leu Thr Val Asp Lys Ser Arg Trp Gln Gln Gly Asn Val Phe Ser Cys
210                 215                 220

Ser Val Met His Glu Ala Leu His Asn His Tyr Thr Gln Lys Ser Leu
225                 230                 235                 240

Ser Leu Ser Pro Gly Lys
                 245

<210> SEQ ID NO 18
<211> LENGTH: 237
<212> TYPE: PRT
<213> ORGANISM: Artificial Sequence
<220> FEATURE:
<223> OTHER INFORMATION: Synthetic Peptide
      K5(74-80 Active Zone)frag-Fc

<400> SEQUENCE: 18

Pro Arg Lys Leu Tyr Asp Tyr Lys Ser Cys Asp Lys Thr His Thr Cys
 1               5                  10                  15

Pro Pro Cys Pro Ala Pro Glu Leu Leu Gly Gly Pro Ser Val Phe Leu
             20                  25                  30

Phe Pro Pro Lys Pro Lys Asp Thr Leu Met Ile Ser Arg Thr Pro Glu
         35                  40                  45

Val Thr Cys Val Val Val Asp Val Ser His Glu Asp Pro Glu Val Lys
 50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
             85                  90                  95

Thr Val Leu His Gln Asp Trp Leu Asn Gly Lys Glu Tyr Lys Cys Lys
                 100                 105                 110

Val Ser Asn Lys Ala Leu Pro Ala Pro Ile Glu Lys Thr Ile Ser Lys
             115                 120                 125

```
Ala Lys Gly Gln Pro Arg Glu Pro Gln Val Tyr Thr Leu Pro Pro Ser
        130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 19
<211> LENGTH: 93
<212> TYPE: PRT
<213> ORGANISM: Artificial Sequence
<220> FEATURE:
<223> OTHER INFORMATION: Synthetic Peptide
      Kr1(1-93 Active Zone)frag

<400> SEQUENCE: 19

Gly Ser Asn Lys Asn His Lys Cys Tyr Asn Ser Thr Gly Val Asp Tyr
1               5                   10                  15

Arg Gly Thr Val Ser Val Thr Lys Ser Gly Arg Gln Cys Gln Pro Trp
            20                  25                  30

Asn Ser Gln Tyr Pro His Thr His Thr Phe Thr Ala Leu Arg Phe Pro
        35                  40                  45

Glu Leu Asn Gly Gly His Ser Tyr Cys Arg Asn Pro Gly Asn Gln Lys
    50                  55                  60

Glu Ala Pro Trp Cys Phe Thr Leu Asp Glu Asn Phe Lys Ser Asp Leu
65                  70                  75                  80

Cys Asp Ile Pro Ala Cys Asp Ser Lys Asp Ser Asp Ile
                85                  90

<210> SEQ ID NO 20
<211> LENGTH: 317
<212> TYPE: PRT
<213> ORGANISM: Artificial Sequence
<220> FEATURE:
<223> OTHER INFORMATION: Synthetic Peptide
      Kr1(3-91 Active Zone)frag-Fc

<400> SEQUENCE: 20

Asn Lys Asn His Lys Cys Tyr Asn Ser Thr Gly Val Asp Tyr Arg Gly
1               5                   10                  15

Thr Val Ser Val Thr Lys Ser Gly Arg Gln Cys Gln Pro Trp Asn Ser
            20                  25                  30

Gln Tyr Pro His Thr His Thr Phe Thr Ala Leu Arg Phe Pro Glu Leu
        35                  40                  45

Asn Gly Gly His Ser Tyr Cys Arg Asn Pro Gly Asn Gln Lys Glu Ala
    50                  55                  60

Pro Trp Cys Phe Thr Leu Asp Glu Asn Phe Lys Ser Asp Leu Cys Asp
65                  70                  75                  80

Ile Pro Ala Cys Asp Ser Lys Asp Ser Cys Asp Lys Thr His Thr Cys
                85                  90                  95
```

Pro Pro Cys Pro Ala Pro Glu Leu Leu Gly Gly Pro Ser Val Phe Leu
            100                 105                 110

Phe Pro Pro Lys Pro Lys Asp Thr Leu Met Ile Ser Arg Thr Pro Glu
            115                 120                 125

Val Thr Cys Val Val Val Asp Val Ser His Glu Asp Pro Glu Val Lys
130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
                165                 170                 175

Thr Val Leu His Gln Asp Trp Leu Asn Gly Lys Glu Tyr Lys Cys Lys
            180                 185                 190

Val Ser Asn Lys Ala Leu Pro Ala Pro Ile Glu Lys Thr Ile Ser Lys
            195                 200                 205

Ala Lys Gly Gln Pro Arg Glu Pro Gln Val Tyr Thr Leu Pro Pro Ser
210                 215                 220

Arg Asp Glu Leu Thr Lys Asn Gln Val Ser Leu Thr Cys Leu Val Lys
225                 230                 235                 240

Gly Phe Tyr Pro Ser Asp Ile Ala Val Glu Trp Glu Ser Asn Gly Gln
                245                 250                 255

Pro Glu Asn Asn Tyr Lys Thr Thr Pro Pro Val Leu Asp Ser Asp Gly
            260                 265                 270

Ser Phe Phe Leu Tyr Ser Lys Leu Thr Val Asp Lys Ser Arg Trp Gln
            275                 280                 285

Gln Gly Asn Val Phe Ser Cys Ser Val Met His Glu Ala Leu His Asn
            290                 295                 300

His Tyr Thr Gln Lys Ser Leu Ser Leu Ser Pro Gly Lys
305                 310                 315

<210> SEQ ID NO 21
<211> LENGTH: 262
<212> TYPE: PRT
<213> ORGANISM: Artificial Sequence
<220> FEATURE:
<223> OTHER INFORMATION: Synthetic Peptide
      Kr1(58-91 Active Zone)frag-Fc

<400> SEQUENCE: 21

Arg Asn Pro Gly Asn Gln Lys Glu Ala Pro Trp Cys Phe Thr Leu Asp
1               5                   10                  15

Glu Asn Phe Lys Ser Asp Leu Cys Asp Ile Pro Ala Cys Asp Ser Lys
            20                  25                  30

Asp Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro

```
                        130                 135                 140
Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                    165                 170                 175

Gln Val Ser Leu Thr Cys Leu Val Lys Gly Phe Tyr Pro Ser Asp Ile
                180                 185                 190

Ala Val Glu Trp Glu Ser Asn Gly Gln Pro Glu Asn Asn Tyr Lys Thr
                195                 200                 205

Thr Pro Pro Val Leu Asp Ser Asp Gly Ser Phe Phe Leu Tyr Ser Lys
            210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260
```

<210> SEQ ID NO 22
<211> LENGTH: 262
<212> TYPE: PRT
<213> ORGANISM: Artificial Sequence
<220> FEATURE:
<223> OTHER INFORMATION: Synthetic Peptide
      Kr1(58-91 Active Zone with Ala sub Cys)frag-Fc

<400> SEQUENCE: 22

```
Arg Asn Pro Gly Asn Gln Lys Glu Ala Pro Trp Ala Phe Thr Leu Asp
1               5                   10                  15

Glu Asn Phe Lys Ser Asp Leu Ala Asp Ile Pro Ala Ala Asp Ser Lys
                20                  25                  30

Asp Ser Cys Asp Lys Thr His Thr Cys Pro Pro Cys Pro Ala Pro Glu
                35                  40                  45

Leu Leu Gly Gly Pro Ser Val Phe Leu Phe Pro Pro Lys Pro Lys Asp
            50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
                100                 105                 110

Ser Thr Tyr Arg Val Val Ser Val Leu Thr Val Leu His Gln Asp Trp
            115                 120                 125

Leu Asn Gly Lys Glu Tyr Lys Cys Lys Val Ser Asn Lys Ala Leu Pro
            130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                    165                 170                 175

Gln Val Ser Leu Thr Cys Leu Val Lys Gly Phe Tyr Pro Ser Asp Ile
                180                 185                 190

Ala Val Glu Trp Glu Ser Asn Gly Gln Pro Glu Asn Asn Tyr Lys Thr
                195                 200                 205

Thr Pro Pro Val Leu Asp Ser Asp Gly Ser Phe Phe Leu Tyr Ser Lys
            210                 215                 220
```

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
            245                 250                 255

Ser Leu Ser Pro Gly Lys
            260

<210> SEQ ID NO 23
<211> LENGTH: 262
<212> TYPE: PRT
<213> ORGANISM: Artificial Sequence
<220> FEATURE:
<223> OTHER INFORMATION: Synthetic Peptide
      Kr1(58-91 Active Zone with Val sub Cys)frag-Fc

<400> SEQUENCE: 23

Arg Asn Pro Gly Asn Gln Lys Glu Ala Pro Trp Val Phe Thr Leu Asp
1               5                   10                  15

Glu Asn Phe Lys Ser Asp Leu Val Asp Ile Pro Ala Val Asp Ser Lys
            20                  25                  30

Asp Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
            85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
            245                 250                 255

Ser Leu Ser Pro Gly Lys
            260

<210> SEQ ID NO 24
<211> LENGTH: 262
<212> TYPE: PRT
<213> ORGANISM: Artificial Sequence
<220> FEATURE:
<223> OTHER INFORMATION: Synthetic Peptide
      Kr1(58-91 Active Zone with Ile sub Cys)frag-Fc

<400> SEQUENCE: 24

Arg Asn Pro Gly Asn Gln Lys Glu Ala Pro Trp Ile Phe Thr Leu Asp
1               5                   10                  15

Glu Asn Phe Lys Ser Asp Leu Ile Asp Ile Pro Ala Ile Asp Ser Lys
                20                  25                  30

Asp Ser Cys Asp Lys Thr His Thr Cys Pro Pro Cys Pro Ala Pro Glu
            35                  40                  45

Leu Leu Gly Gly Pro Ser Val Phe Leu Phe Pro Pro Lys Pro Lys Asp
        50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260

<210> SEQ ID NO 25
<211> LENGTH: 262
<212> TYPE: PRT
<213> ORGANISM: Artificial Sequence
<220> FEATURE:
<223> OTHER INFORMATION: Synthetic Peptide
      Kr1(58-91 Active Zone with Leu sub Cys)frag-Fc

<400> SEQUENCE: 25

Arg Asn Pro Gly Asn Gln Lys Glu Ala Pro Trp Leu Phe Thr Leu Asp
1               5                   10                  15

Glu Asn Phe Lys Ser Asp Leu Leu Asp Ile Pro Ala Leu Asp Ser Lys
                20                  25                  30

Asp Ser Cys Asp Lys Thr His Thr Cys Pro Pro Cys Pro Ala Pro Glu
            35                  40                  45

Leu Leu Gly Gly Pro Ser Val Phe Leu Phe Pro Pro Lys Pro Lys Asp
        50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
            85                  90                  95

Val Glu Val His Asn Ala Lys Thr Lys Pro Arg Glu Glu Gln Tyr Asn
           100                 105                 110

Ser Thr Tyr Arg Val Val Ser Val Leu Thr Val Leu His Gln Asp Trp
           115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
            165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
            195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
            245                 250                 255

Ser Leu Ser Pro Gly Lys
            260

<210> SEQ ID NO 26
<211> LENGTH: 251
<212> TYPE: PRT
<213> ORGANISM: Artificial Sequence
<220> FEATURE:
<223> OTHER INFORMATION: Synthetic Peptide
      Kr1(58-80 Active Zone)frag-Fc

<400> SEQUENCE: 26

Arg Asn Pro Gly Asn Gln Lys Glu Ala Pro Trp Cys Phe Thr Leu Asp
1               5                   10                  15

Glu Asn Phe Lys Ser Asp Leu Cys Asp Lys Thr His Thr Cys Pro Pro
            20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
            85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
    115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe 165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
            245                 250

<210> SEQ ID NO 27
<211> LENGTH: 251
<212> TYPE: PRT
<213> ORGANISM: Artificial Sequence
<220> FEATURE:
<223> OTHER INFORMATION: Synthetic Peptide
     Kr1(58-80 Active Zone w Ala sub Cys)frag-Fc

<400> SEQUENCE: 27

Arg Asn Pro Gly Asn Gln Lys Glu Ala Pro Trp Ala Phe Thr Leu Asp
1               5                   10                  15

Glu Asn Phe Lys Ser Asp Leu Cys Asp Lys Thr His Thr Cys Pro Pro
            20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
            165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
            245                 250

<210> SEQ ID NO 28
<211> LENGTH: 251

<212> TYPE: PRT
<213> ORGANISM: Artificial Sequence
<220> FEATURE:
<223> OTHER INFORMATION: Synthetic Peptide
      Kr1(58-80 Active Zone w Val sub Cys)frag-Fc

<400> SEQUENCE: 28

Arg Asn Pro Gly Asn Gln Lys Glu Ala Pro Trp Val Phe Thr Leu Asp
1               5                   10                  15

Glu Asn Phe Lys Ser Asp Leu Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
                100                 105                 110

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
                180                 185                 190

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 29
<211> LENGTH: 251
<212> TYPE: PRT
<213> ORGANISM: Artificial Sequence
<220> FEATURE:
<223> OTHER INFORMATION: Synthetic Peptide
      Kr1(58-80 Active Zone w Ile sub Cys)frag-Fc

<400> SEQUENCE: 29

Arg Asn Pro Gly Asn Gln Lys Glu Ala Pro Trp Ile Phe Thr Leu Asp
1               5                   10                  15

Glu Asn Phe Lys Ser Asp Leu Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
50                  55                  60

```
Cys Val Val Asp Val Ser His Glu Asp Pro Glu Val Lys Phe Asn
 65                  70                  75                  80

Trp Tyr Val Asp Gly Val Glu Val His Asn Ala Lys Thr Lys Pro Arg
                 85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 30
<211> LENGTH: 251
<212> TYPE: PRT
<213> ORGANISM: Artificial Sequence
<220> FEATURE:
<223> OTHER INFORMATION: Synthetic Peptide
      Kr1(58-80 Active Zone w Leu sub Cys)frag-Fc

<400> SEQUENCE: 30

Arg Asn Pro Gly Asn Gln Lys Glu Ala Pro Trp Leu Phe Thr Leu Asp
1               5                   10                  15

Glu Asn Phe Lys Ser Asp Leu Cys Asp Lys Thr His Thr Cys Pro Pro
                20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
 65                  70                  75                  80

Trp Tyr Val Asp Gly Val Glu Val His Asn Ala Lys Thr Lys Pro Arg
                 85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175
```

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
            245                 250

<210> SEQ ID NO 31
<211> LENGTH: 239
<212> TYPE: PRT
<213> ORGANISM: Artificial Sequence
<220> FEATURE:
<223> OTHER INFORMATION: Synthetic Peptide
      Kr1(70-80 Active Zone)frag-Fc

<400> SEQUENCE: 31

Phe Thr Leu Asp Glu Asn Phe Lys Ser Asp Leu Cys Asp Lys Thr His
1               5                   10                  15

Thr Cys Pro Pro Cys Pro Ala Pro Glu Leu Leu Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Val Asp Val Ser His Glu Asp Pro Glu
50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
130                 135                 140

Pro Ser Arg Asp Glu Leu Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Val Phe Ser Cys Ser Val Met His Glu Ala Leu
210                 215                 220

His Asn His Tyr Thr Gln Lys Ser Leu Ser Leu Ser Pro Gly Lys
225                 230                 235

<210> SEQ ID NO 32
<211> LENGTH: 236
<212> TYPE: PRT
<213> ORGANISM: Artificial Sequence
<220> FEATURE:
<223> OTHER INFORMATION: Synthetic Peptide Kr1(73-80 Active Zone)frag-Fc

<400> SEQUENCE: 32

Asp Glu Asn Phe Lys Ser Asp Leu Cys Asp Lys Thr His Thr Cys Pro
1               5                   10                  15
Pro Cys Pro Ala Pro Glu Leu Leu Gly Gly Pro Ser Val Phe Leu Phe
            20                  25                  30
Pro Pro Lys Pro Lys Asp Thr Leu Met Ile Ser Arg Thr Pro Glu Val
        35                  40                  45
Thr Cys Val Val Val Asp Val Ser His Glu Asp Pro Glu Val Lys Phe
    50                  55                  60
Asn Trp Tyr Val Asp Gly Val Glu Val His Asn Ala Lys Thr Lys Pro
65                  70                  75                  80
Arg Glu Glu Gln Tyr Asn Ser Thr Tyr Arg Val Val Ser Val Leu Thr
                85                  90                  95
Val Leu His Gln Asp Trp Leu Asn Gly Lys Glu Tyr Lys Cys Lys Val
            100                 105                 110
Ser Asn Lys Ala Leu Pro Ala Pro Ile Glu Lys Thr Ile Ser Lys Ala
        115                 120                 125
Lys Gly Gln Pro Arg Glu Pro Gln Val Tyr Thr Leu Pro Pro Ser Arg
    130                 135                 140
Asp Glu Leu Thr Lys Asn Gln Val Ser Leu Thr Cys Leu Val Lys Gly
145                 150                 155                 160
Phe Tyr Pro Ser Asp Ile Ala Val Glu Trp Glu Ser Asn Gly Gln Pro
                165                 170                 175
Glu Asn Asn Tyr Lys Thr Thr Pro Pro Val Leu Asp Ser Asp Gly Ser
            180                 185                 190
Phe Phe Leu Tyr Ser Lys Leu Thr Val Asp Lys Ser Arg Trp Gln Gln
        195                 200                 205
Gly Asn Val Phe Ser Cys Ser Val Met His Glu Ala Leu His Asn His
    210                 215                 220
Tyr Thr Gln Lys Ser Leu Ser Leu Ser Pro Gly Lys
225                 230                 235

<210> SEQ ID NO 33
<211> LENGTH: 85
<212> TYPE: PRT
<213> ORGANISM: Artificial Sequence
<220> FEATURE:
<223> OTHER INFORMATION: Synthetic Peptide
      Kr2(1-85 Active Zone)frag

<400> SEQUENCE: 33

Gly Arg Tyr His Gln Cys Tyr Asn Gly Ser Gly Met Asp Tyr Arg Gly
1               5                   10                  15
Thr Ala Ser Thr Thr Lys Ser Gly His Gln Cys Gln Pro Trp Ala Leu
            20                  25                  30
Gln His Pro His Ser His His Leu Ser Ser Thr Asp Phe Pro Glu Leu
        35                  40                  45
Gly Gly Gly His Ala Tyr Cys Arg Asn Pro Gly Gly Gln Met Glu Gly
    50                  55                  60
Pro Trp Cys Phe Thr Gln Asn Lys Asn Val Arg Met Glu Leu Cys Asp
65                  70                  75                  80
Val Pro Ser Cys Ser
                85

<210> SEQ ID NO 34
<211> LENGTH: 316
<212> TYPE: PRT
<213> ORGANISM: Artificial Sequence
<220> FEATURE:
<223> OTHER INFORMATION: Synthetic Peptide Kr2(1-85 Active Zone)frag-Fc

<400> SEQUENCE: 34

```
Gly Arg Tyr His Gln Cys Tyr Asn Gly Ser Gly Met Asp Tyr Arg Gly
 1               5                  10                  15

Thr Ala Ser Thr Thr Lys Ser Gly His Gln Cys Gln Pro Trp Ala Leu
             20                  25                  30

Gln His Pro His Ser His His Leu Ser Ser Thr Asp Phe Pro Glu Leu
         35                  40                  45

Gly Gly Gly His Ala Tyr Cys Arg Asn Pro Gly Gly Gln Met Glu Gly
     50                  55                  60

Pro Trp Cys Phe Thr Gln Asn Lys Asn Val Arg Met Glu Leu Cys Asp
65                  70                  75                  80

Val Pro Ser Cys Ser Pro Lys Ser Cys Asp Lys Thr His Thr Cys Pro
                 85                  90                  95

Pro Cys Pro Ala Pro Glu Leu Leu Gly Gly Pro Ser Val Phe Leu Phe
            100                 105                 110

Pro Pro Lys Pro Lys Asp Thr Leu Met Ile Ser Arg Thr Pro Glu Val
        115                 120                 125

Thr Cys Val Val Val Asp Val Ser His Glu Asp Pro Glu Val Lys Phe
    130                 135                 140

Asn Trp Tyr Val Asp Gly Val Glu Val His Asn Ala Lys Thr Lys Pro
145                 150                 155                 160

Arg Glu Glu Gln Tyr Asn Ser Thr Tyr Arg Val Val Ser Val Leu Thr
                165                 170                 175

Val Leu His Gln Asp Trp Leu Asn Gly Lys Glu Tyr Lys Cys Lys Val
            180                 185                 190

Ser Asn Lys Ala Leu Pro Ala Pro Ile Glu Lys Thr Ile Ser Lys Ala
        195                 200                 205

Lys Gly Gln Pro Arg Glu Pro Gln Val Tyr Thr Leu Pro Pro Ser Arg
    210                 215                 220

Asp Glu Leu Thr Lys Asn Gln Val Ser Leu Thr Cys Leu Val Lys Gly
225                 230                 235                 240

Phe Tyr Pro Ser Asp Ile Ala Val Glu Trp Glu Ser Asn Gly Gln Pro
                245                 250                 255

Glu Asn Asn Tyr Lys Thr Thr Pro Pro Val Leu Asp Ser Asp Gly Ser
            260                 265                 270

Phe Phe Leu Tyr Ser Lys Leu Thr Val Asp Lys Ser Arg Trp Gln Gln
        275                 280                 285

Gly Asn Val Phe Ser Cys Ser Val Met His Glu Ala Leu His Asn His
    290                 295                 300

Tyr Thr Gln Lys Ser Leu Ser Leu Ser Pro Gly Lys
305                 310                 315
```

<210> SEQ ID NO 35
<211> LENGTH: 261
<212> TYPE: PRT
<213> ORGANISM: Artificial Sequence
<220> FEATURE:
<223> OTHER INFORMATION: Synthetic Peptide Kr2(56-85 Active Zone)frag-Fc

<400> SEQUENCE: 35

```
Arg Asn Pro Gly Gly Gln Met Glu Gly Pro Trp Cys Phe Thr Gln Asn
1               5                   10                  15

Lys Asn Val Arg Met Glu Leu Cys Asp Val Pro Ser Cys Ser Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260
```

```
<210> SEQ ID NO 36
<211> LENGTH: 261
<212> TYPE: PRT
<213> ORGANISM: Artificial Sequence
<220> FEATURE:
<223> OTHER INFORMATION: Synthetic Peptide
      Kr2(56-85 Active Zone w Ala sub Cys)frag-Fc
```

<400> SEQUENCE: 36

```
Arg Asn Pro Gly Gly Gln Met Glu Gly Pro Trp Ala Phe Thr Gln Asn
1               5                   10                  15

Lys Asn Val Arg Met Glu Leu Ala Asp Val Pro Ser Ala Ser Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80
```

-continued

```
Ser His Glu Asp Pro Glu Val Lys Phe Asn Trp Tyr Val Asp Gly Val
             85                  90                  95

Glu Val His Asn Ala Lys Thr Lys Pro Arg Glu Glu Gln Tyr Asn Ser
           100                 105                 110

Thr Tyr Arg Val Val Ser Val Leu Thr Val Leu His Gln Asp Trp Leu
       115                 120                 125

Asn Gly Lys Glu Tyr Lys Cys Lys Val Ser Asn Lys Ala Leu Pro Ala
   130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
            165                 170                 175

Val Ser Leu Thr Cys Leu Val Lys Gly Phe Tyr Pro Ser Asp Ile Ala
        180                 185                 190

Val Glu Trp Glu Ser Asn Gly Gln Pro Glu Asn Asn Tyr Lys Thr Thr
    195                 200                 205

Pro Pro Val Leu Asp Ser Asp Gly Ser Phe Phe Leu Tyr Ser Lys Leu
210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
            245                 250                 255

Leu Ser Pro Gly Lys
            260

<210> SEQ ID NO 37
<211> LENGTH: 261
<212> TYPE: PRT
<213> ORGANISM: Artificial Sequence
<220> FEATURE:
<223> OTHER INFORMATION: Synthetic Peptide
      Kr2(56-85 Active Zone w Val sub Cys)frag-Fc

<400> SEQUENCE: 37

Arg Asn Pro Gly Gly Gln Met Glu Gly Pro Trp Val Phe Thr Gln Asn
1               5                   10                  15

Lys Asn Val Arg Met Glu Leu Val Asp Val Pro Ser Val Ser Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
             85                  90                  95

Glu Val His Asn Ala Lys Thr Lys Pro Arg Glu Glu Gln Tyr Asn Ser
           100                 105                 110

Thr Tyr Arg Val Val Ser Val Leu Thr Val Leu His Gln Asp Trp Leu
       115                 120                 125

Asn Gly Lys Glu Tyr Lys Cys Lys Val Ser Asn Lys Ala Leu Pro Ala
   130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
            165                 170                 175
```

```
Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
            195                 200                 205

Pro Pro Val Leu Asp Ser Asp Gly Ser Phe Phe Leu Tyr Ser Lys Leu
            210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260

<210> SEQ ID NO 38
<211> LENGTH: 261
<212> TYPE: PRT
<213> ORGANISM: Artificial Sequence
<220> FEATURE:
<223> OTHER INFORMATION: Synthetic Peptide
      Kr2(56-85 Active Zone w Ile sub Cys)frag-Fc

<400> SEQUENCE: 38

Arg Asn Pro Gly Gly Gln Met Glu Gly Pro Trp Ile Phe Thr Gln Asn
1               5                   10                  15

Lys Asn Val Arg Met Glu Leu Ile Asp Val Pro Ser Ile Ser Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
            195                 200                 205

Pro Pro Val Leu Asp Ser Asp Gly Ser Phe Phe Leu Tyr Ser Lys Leu
            210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
```

<210> SEQ ID NO 39
<211> LENGTH: 261
<212> TYPE: PRT
<213> ORGANISM: Artificial Sequence
<220> FEATURE:
<223> OTHER INFORMATION: Synthetic Peptide
      Kr2(56-85 Active Zone w Leu sub Cys)frag-Fc

<400> SEQUENCE: 39

```
Arg Asn Pro Gly Gly Gln Met Glu Gly Pro Trp Leu Phe Thr Gln Asn
1               5                   10                  15

Lys Asn Val Arg Met Glu Leu Leu Asp Val Pro Ser Leu Ser Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260
```

<210> SEQ ID NO 40
<211> LENGTH: 249
<212> TYPE: PRT
<213> ORGANISM: Artificial Sequence
<220> FEATURE:
<223> OTHER INFORMATION: Synthetic Peptide
      Kr2(68-85 Active Zone)frag-Fc

<400> SEQUENCE: 40

```
Phe Thr Gln Asn Lys Asn Val Arg Met Glu Leu Cys Asp Val Pro Ser
1               5                   10                  15

Cys Ser Pro Lys Ser Cys Asp Lys Thr His Thr Cys Pro Pro Cys Pro
```

```
                    20                  25                  30
Ala Pro Glu Leu Leu Gly Gly Pro Ser Val Phe Leu Phe Pro Pro Lys
                35                  40                  45

Pro Lys Asp Thr Leu Met Ile Ser Arg Thr Pro Glu Val Thr Cys Val
         50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
            130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 41
<211> LENGTH: 249
<212> TYPE: PRT
<213> ORGANISM: Artificial Sequence
<220> FEATURE:
<223> OTHER INFORMATION: Synthetic Peptide
      Kr2(68-85  Active Zone w Ala sub Cys)frag-Fc

<400> SEQUENCE: 41

Phe Thr Gln Asn Lys Asn Val Arg Met Glu Leu Ala Asp Val Pro Ser
1               5                   10                  15

Ala Ser Pro Lys Ser Cys Asp Lys Thr His Thr Cys Pro Pro Cys Pro
                20                  25                  30

Ala Pro Glu Leu Leu Gly Gly Pro Ser Val Phe Leu Phe Pro Pro Lys
                35                  40                  45

Pro Lys Asp Thr Leu Met Ile Ser Arg Thr Pro Glu Val Thr Cys Val
         50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
            115                 120                 125
```

```
Ala Leu Pro Ala Pro Ile Glu Lys Thr Ile Ser Lys Ala Lys Gly Gln
            130                 135                 140

Lys Ser Leu Ser Leu Ser Pro Gly Lys
            245

<210> SEQ ID NO 43
<211> LENGTH: 249
<212> TYPE: PRT
<213> ORGANISM: Artificial Sequence
<220> FEATURE:
<223> OTHER INFORMATION: Synthetic Peptide
      Kr2(68-85 Active Zone w Ile sub Cys)frag-Fc

<400> SEQUENCE: 43

Phe Thr Gln Asn Lys Asn Val Arg Met Glu Leu Ile Asp Val Pro Ser
1               5                   10                  15

Ile Ser Pro Lys Ser Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
            245

<210> SEQ ID NO 44
<211> LENGTH: 249
<212> TYPE: PRT
<213> ORGANISM: Artificial Sequence
<220> FEATURE:
<223> OTHER INFORMATION: Synthetic Peptide
      Kr2(68-85 Active Zone w Leu sub Cys)frag-Fc

<400> SEQUENCE: 44

Phe Thr Gln Asn Lys Asn Val Arg Met Glu Leu Leu Asp Val Pro Ser
1               5                   10                  15

Leu Ser Pro Lys Ser Cys Asp Lys Thr His Thr Cys Pro Pro Cys Pro
            20                  25                  30

```
Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 45
<211> LENGTH: 241
<212> TYPE: PRT
<213> ORGANISM: Artificial Sequence
<220> FEATURE:
<223> OTHER INFORMATION: Synthetic Peptide
      Kr2(68-79 Active Zone w Lys sub Cys)frag-Fc

<400> SEQUENCE: 45

Phe Thr Gln Asn Lys Asn Val Arg Met Glu Leu Lys Ser Cys Asp Lys
 1               5                  10                  15

Thr His Thr Cys Pro Pro Cys Pro Ala Pro Glu Leu Leu Gly Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
 50                  55                  60

Pro Glu Val Lys Phe Asn Trp Tyr Val Asp Gly Val Glu Val His Asn
 65                  70                  75                  80

Ala Lys Thr Lys Pro Arg Glu Glu Gln Tyr Asn Ser Thr Tyr Arg Val
                 85                  90                  95

Val Ser Val Leu Thr Val Leu His Gln Asp Trp Leu Asn Gly Lys Glu
            100                 105                 110

Tyr Lys Cys Lys Val Ser Asn Lys Ala Leu Pro Ala Pro Ile Glu Lys
        115                 120                 125

Thr Ile Ser Lys Ala Lys Gly Gln Pro Arg Glu Pro Gln Val Tyr Thr
```

```
                130             135             140
Leu Pro Pro Ser Arg Asp Glu Leu Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys

<210> SEQ ID NO 46
<211> LENGTH: 24
<212> TYPE: PRT
<213> ORGANISM: Artificial Sequence
<220> FEATURE:
<223> OTHER INFORMATION: Synthetic Peptide
      Kr1(58-81 Active Zone w Ala sub Cys
      and w Lys sub Cys)frag

<400> SEQUENCE: 46

Arg Asn Pro Gly Asn Gln Lys Glu Ala Pro Trp Ala Phe Thr Leu Asp
1               5                   10                  15

Glu Asn Phe Lys Ser Asp Leu Lys
            20

<210> SEQ ID NO 47
<211> LENGTH: 24
<212> TYPE: PRT
<213> ORGANISM: Artificial Sequence
<220> FEATURE:
<223> OTHER INFORMATION: Synthetic Peptide
      Kr1(58-81 Active Zone w Val sub Cys
      and w Lys sub Cys)frag

<400> SEQUENCE: 47

Arg Asn Pro Gly Asn Gln Lys Glu Ala Pro Trp Val Phe Thr Leu Asp
1               5                   10                  15

Glu Asn Phe Lys Ser Asp Leu Lys
            20

<210> SEQ ID NO 48
<211> LENGTH: 24
<212> TYPE: PRT
<213> ORGANISM: Artificial Sequence
<220> FEATURE:
<223> OTHER INFORMATION: Synthetic Peptide
      Kr1(58-81 Active Zone w Ile sub Cys
      and w Lys sub Cys)frag

<400> SEQUENCE: 48

Arg Asn Pro Gly Asn Gln Lys Glu Ala Pro Trp Ile Phe Thr Leu Asp
1               5                   10                  15

Glu Asn Phe Lys Ser Asp Leu Lys
            20

<210> SEQ ID NO 49
<211> LENGTH: 24
```

```
<212> TYPE: PRT
<213> ORGANISM: Artificial Sequence
<220> FEATURE:
<223> OTHER INFORMATION: Synthetic Peptide
      Kr1(58-81 Active Zone w Leu sub Cys
      and w Lys sub Cys)frag

<400> SEQUENCE: 49

Arg Asn Pro Gly Asn Gln Lys Glu Ala Pro Trp Leu Phe Thr Leu Asp
1               5                   10                  15

Glu Asn Phe Lys Ser Asp Leu Lys
            20

<210> SEQ ID NO 50
<211> LENGTH: 23
<212> TYPE: PRT
<213> ORGANISM: Artificial Sequence
<220> FEATURE:
<223> OTHER INFORMATION: Synthetic Peptide
      Kr1(58-80 Active Zone w Ala sub Cys)frag

<400> SEQUENCE: 50

Arg Asn Pro Gly Asn Gln Lys Glu Ala Pro Trp Ala Phe Thr Leu Asp
1               5                   10                  15

Glu Asn Phe Lys Ser Asp Leu
            20

<210> SEQ ID NO 51
<211> LENGTH: 23
<212> TYPE: PRT
<213> ORGANISM: Artificial Sequence
<220> FEATURE:
<223> OTHER INFORMATION: Synthetic Peptide
      Kr1(58-80 Active Zone w Val sub Cys)frag

<400> SEQUENCE: 51

Arg Asn Pro Gly Asn Gln Lys Glu Ala Pro Trp Val Phe Thr Leu Asp
1               5                   10                  15

Glu Asn Phe Lys Ser Asp Leu
            20

<210> SEQ ID NO 52
<211> LENGTH: 23
<212> TYPE: PRT
<213> ORGANISM: Artificial Sequence
<220> FEATURE:
<223> OTHER INFORMATION: Synthetic Peptide
      Kr1(58-80 Active Zone w Ile sub Cys)frag

<400> SEQUENCE: 52

Arg Asn Pro Gly Asn Gln Lys Glu Ala Pro Trp Ile Phe Thr Leu Asp
1               5                   10                  15

Glu Asn Phe Lys Ser Asp Leu
            20

<210> SEQ ID NO 53
<211> LENGTH: 23
<212> TYPE: PRT
<213> ORGANISM: Artificial Sequence
<220> FEATURE:
<223> OTHER INFORMATION: Synthetic Peptide
      Kr1(58-80 Active Zone w Leu sub Cys)frag

<400> SEQUENCE: 53

Arg Asn Pro Gly Asn Gln Lys Glu Ala Pro Trp Leu Phe Thr Leu Asp
1               5                   10                  15
```

```
Glu Asn Phe Lys Ser Asp Leu
            20

<210> SEQ ID NO 54
<211> LENGTH: 12
<212> TYPE: PRT
<213> ORGANISM: Artificial Sequence
<220> FEATURE:
<223> OTHER INFORMATION: Synthetic Peptide
      Kr1(58-69 Active Zone w Lys sub Cys)frag

<400> SEQUENCE: 54

Arg Asn Pro Gly Asn Gln Lys Glu Ala Pro Trp Lys
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Peptide
      Kr1(58-68 Active Zone)frag

<400> SEQUENCE: 55

Arg Asn Pro Gly Asn Gln Lys Glu Ala Pro Trp
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Peptide
      Kr1(70-81 Active Zone w Lys sub Cys)frag

<400> SEQUENCE: 56

Phe Thr Leu Asp Glu Asn Phe Lys Ser Asp Leu Lys
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic Peptide
      Kr1(70-80 Active Zone)frag

<400> SEQUENCE: 57

Phe Thr Leu Asp Glu Asn Phe Lys Ser Asp Leu
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic Peptide
      Kr1(71-80 Active Zone)frag

<400> SEQUENCE: 58

Thr Leu Asp Glu Asn Phe Lys Ser Asp Leu
1               5                   10

<210> SEQ ID NO 59
<211> LENGTH: 9
<212> TYPE: PRT
<213> ORGANISM: Artificial Sequence
```

```
<220> FEATURE:
<223> OTHER INFORMATION: Synthetic Peptide
      Kr1(72-80 Active Zone)frag

<400> SEQUENCE: 59

Leu Asp Glu Asn Phe Lys Ser Asp Leu
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Peptide
      Kr1(73-80 Active Zone)frag

<400> SEQUENCE: 60

Asp Glu Asn Phe Lys Ser Asp Leu
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Peptide
      Kr1(73-79 Active Zone)frag

<400> SEQUENCE: 61

Asp Glu Asn Phe Lys Ser Asp
1               5

<210> SEQ ID NO 62
<211> LENGTH: 79
<212> TYPE: PRT
<213> ORGANISM: Artificial Sequence
<220> FEATURE:
<223> OTHER INFORMATION: Synthetic Peptide
      Kr2(6-84 Active Zone)frag

<400> SEQUENCE: 62

Cys Tyr Asn Gly Ser Gly Met Asp Tyr Arg Gly Thr Ala Ser Thr Thr
1               5                   10                  15

Lys Ser Gly His Gln Cys Gln Pro Trp Ala Leu Gln His Pro His Ser
            20                  25                  30

His His Leu Ser Ser Thr Asp Phe Pro Glu Leu Gly Gly Gly His Ala
        35                  40                  45

Tyr Cys Arg Asn Pro Gly Gly Gln Met Glu Gly Pro Trp Cys Phe Thr
    50                  55                  60

Gln Asn Lys Asn Val Arg Met Glu Leu Cys Asp Val Pro Ser Cys
65                  70                  75

<210> SEQ ID NO 63
<211> LENGTH: 24
<212> TYPE: PRT
<213> ORGANISM: Artificial Sequence
<220> FEATURE:
<223> OTHER INFORMATION: Synthetic Peptide
      Kr2(56-79 Active Zone w Ala sub Cys
      and Lys sub Cys)frag

<400> SEQUENCE: 63

Arg Asn Pro Gly Gly Gln Met Glu Gly Pro Trp Ala Phe Thr Gln Asn
1               5                   10                  15

Lys Asn Val Arg Met Glu Leu Lys
```

<210> SEQ ID NO 64
<211> LENGTH: 24
<212> TYPE: PRT
<213> ORGANISM: Artificial Sequence
<220> FEATURE:
<223> OTHER INFORMATION: Synthetic Peptide
      Kr2(56-79 Active Zone w Val sub Cys
      and Lys sub Cys)frag

<400> SEQUENCE: 64

Arg Asn Pro Gly Gly Gln Met Glu Gly Pro Trp Val Phe Thr Gln Asn
1               5                   10                  15

Lys Asn Val Arg Met Glu Leu Lys
            20

<210> SEQ ID NO 65
<211> LENGTH: 24
<212> TYPE: PRT
<213> ORGANISM: Artificial Sequence
<220> FEATURE:
<223> OTHER INFORMATION: Synthetic Peptide
      Kr2(56-79 Active Zone w Ile sub Cys
      and Lys sub Cys)

<400> SEQUENCE: 65

Arg Asn Pro Gly Gly Gln Met Glu Gly Pro Trp Ile Phe Thr Gln Asn
1               5                   10                  15

Lys Asn Val Arg Met Glu Leu Lys
            20

<210> SEQ ID NO 66
<211> LENGTH: 24
<212> TYPE: PRT
<213> ORGANISM: Artificial Sequence
<220> FEATURE:
<223> OTHER INFORMATION: Synthetic Peptide
      Kr2(56-79 Active Zone w Leu sub Cys
      and Lys sub Cys)frag

<400> SEQUENCE: 66

Arg Asn Pro Gly Gly Gln Met Glu Gly Pro Trp Leu Phe Thr Gln Asn
1               5                   10                  15

Lys Asn Val Arg Met Glu Leu Lys
            20

<210> SEQ ID NO 67
<211> LENGTH: 23
<212> TYPE: PRT
<213> ORGANISM: Artificial Sequence
<220> FEATURE:
<223> OTHER INFORMATION: Synthetic Peptide
      Kr2(56-78 Active Zone w Ala sub Cys)frag

<400> SEQUENCE: 67

Arg Asn Pro Gly Gly Gln Met Glu Gly Pro Trp Ala Phe Thr Gln Asn
1               5                   10                  15

Lys Asn Val Arg Met Glu Leu
            20

<210> SEQ ID NO 68
<211> LENGTH: 23
<212> TYPE: PRT
<213> ORGANISM: Artificial Sequence
<220> FEATURE:

<223> OTHER INFORMATION: Synthetic Peptide
      Kr2(56-78 Active Zone w Val sub Cys)frag

<400> SEQUENCE: 68

Arg Asn Pro Gly Gly Gln Met Glu Gly Pro Trp Val Phe Thr Gln Asn
1               5                   10                  15

Lys Asn Val Arg Met Glu Leu
            20

<210> SEQ ID NO 69
<211> LENGTH: 23
<212> TYPE: PRT
<213> ORGANISM: Artificial Sequence
<220> FEATURE:
<223> OTHER INFORMATION: Synthetic Peptide
      Kr2(56-78 Active Zone w Ile sub Cys)frag

<400> SEQUENCE: 69

Arg Asn Pro Gly Gly Gln Met Glu Gly Pro Trp Ile Phe Thr Gln Asn
1               5                   10                  15

Lys Asn Val Arg Met Glu Leu
            20

<210> SEQ ID NO 70
<211> LENGTH: 23
<212> TYPE: PRT
<213> ORGANISM: Artificial Sequence
<220> FEATURE:
<223> OTHER INFORMATION: Synthetic Peptide
      Kr2(56-78 Active Zone w Leu sub Cys)frag

<400> SEQUENCE: 70

Arg Asn Pro Gly Gly Gln Met Glu Gly Pro Trp Leu Phe Thr Gln Asn
1               5                   10                  15

Lys Asn Val Arg Met Glu Leu
            20

<210> SEQ ID NO 71
<211> LENGTH: 12
<212> TYPE: PRT
<213> ORGANISM: Artificial Sequence
<220> FEATURE:
<223> OTHER INFORMATION: Synthetic Peptide
      Kr2(56-67 Active Zone with Lys sub Cys)frag

<400> SEQUENCE: 71

Arg Asn Pro Gly Gly Gln Met Glu Gly Pro Trp Lys
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic Peptide
      Kr2(56-66 Active Zone)frag

<400> SEQUENCE: 72

Arg Asn Pro Gly Gly Gln Met Glu Gly Pro Trp
1               5                   10

<210> SEQ ID NO 73
<211> LENGTH: 12
<212> TYPE: PRT
<213> ORGANISM: Artificial Sequence
<220> FEATURE:

<223> OTHER INFORMATION: Synthetic Peptide
      Kr2(68-79 Active Zone w Lys sub Cys)frag

<400> SEQUENCE: 73

Phe Thr Gln Asn Lys Asn Val Arg Met Glu Leu Lys
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic Peptide
      Kr2(68-78 Active Zone)frag

<400> SEQUENCE: 74

Phe Thr Gln Asn Lys Asn Val Arg Met Glu Leu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic Peptide
      Kr2(69-78 Active Zone)frag

<400> SEQUENCE: 75

Thr Gln Asn Lys Asn Val Arg Met Glu Leu
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Synthetic Peptide
      Kr2(70-78 Active Zone)frag

<400> SEQUENCE: 76

Gln Asn Lys Asn Val Arg Met Glu Leu
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic Peptide
      Kr2(70-77 Active Zone)frag

<400> SEQUENCE: 77

Gln Asn Lys Asn Val Arg Met Glu
1               5

<210> SEQ ID NO 78
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Ala sub Cys
      and w Lys sub Cys)frag
<220> FEATURE:
<221> NAME/KEY: VARIANT
<222> LOCATION: 1
<223> OTHER INFORMATION: Xaa is Arg linked to NAc

<400> SEQUENCE: 78

```
Xaa Asn Pro Gly Asn Gln Lys Glu Ala Pro Trp Ala Phe Thr Leu Asp
1               5                   10                  15

Glu Asn Phe Lys Ser Asp Leu Lys
            20

<210> SEQ ID NO 79
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Val sub Cys
      and w Lys sub Cys)frag
<220> FEATURE:
<221> NAME/KEY: VARIANT
<222> LOCATION: 1
<223> OTHER INFORMATION: Xaa is Arg linked to NAc

<400> SEQUENCE: 79

Xaa Asn Pro Gly Asn Gln Lys Glu Ala Pro Trp Val Phe Thr Leu Asp
1               5                   10                  15

Glu Asn Phe Lys Ser Asp Leu Lys
            20

<210> SEQ ID NO 80
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Ile sub Cys
      and w Lys sub Cys)frag
<220> FEATURE:
<221> NAME/KEY: VARIANT
<222> LOCATION: 1
<223> OTHER INFORMATION: Xaa is Arg linked to NAc

<400> SEQUENCE: 80

Xaa Asn Pro Gly Asn Gln Lys Glu Ala Pro Trp Ile Phe Thr Leu Asp
1               5                   10                  15

Glu Asn Phe Lys Ser Asp Leu Lys
            20

<210> SEQ ID NO 81
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Leu sub Cys
      and w Lys sub Cys)frag
<220> FEATURE:
<221> NAME/KEY: VARIANT
<222> LOCATION: 1
<223> OTHER INFORMATION: Xaa is Arg linked to NAc

<400> SEQUENCE: 81

Xaa Asn Pro Gly Asn Gln Lys Glu Ala Pro Trp Leu Phe Thr Leu Asp
1               5                   10                  15

Glu Asn Phe Lys Ser Asp Leu Lys
            20

<210> SEQ ID NO 82
<211> LENGTH: 24
<212> TYPE: PRT
<213> ORGANISM: Artificial Sequence
<220> FEATURE:
```

```
<223> OTHER INFORMATION: Synthetic Peptide
      Mod-Kr1(58-81 Active Zone w Ala sub Cys
      and w Lys sub Cys)frag
<220> FEATURE:
<221> NAME/KEY: VARIANT
<222> LOCATION: 1
<223> OTHER INFORMATION: Xaa is Arg linked to MPA

<400> SEQUENCE: 82

Xaa Asn Pro Gly Asn Gln Lys Glu Ala Pro Trp Ala Phe Thr Leu Asp
1               5                   10                  15

Glu Asn Phe Lys Ser Asp Leu Lys
            20

<210> SEQ ID NO 83
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Val sub Cys
      and w Lys sub Cys)frag
<220> FEATURE:
<221> NAME/KEY: VARIANT
<222> LOCATION: 1
<223> OTHER INFORMATION: Xaa is Arg linked to MPA

<400> SEQUENCE: 83

Xaa Asn Pro Gly Asn Gln Lys Glu Ala Pro Trp Val Phe Thr Leu Asp
1               5                   10                  15

Glu Asn Phe Lys Ser Asp Leu Lys
            20

<210> SEQ ID NO 84
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Ile sub Cys
      and w Lys sub Cys)frag
<220> FEATURE:
<221> NAME/KEY: VARIANT
<222> LOCATION: 1
<223> OTHER INFORMATION: Xaa is Arg linked to MPA

<400> SEQUENCE: 84

Xaa Asn Pro Gly Asn Gln Lys Glu Ala Pro Trp Ile Phe Thr Leu Asp
1               5                   10                  15

Glu Asn Phe Lys Ser Asp Leu Lys
            20

<210> SEQ ID NO 85
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Leu sub Cys
      and w Lys sub Cys)frag
<220> FEATURE:
<221> NAME/KEY: VARIANT
<222> LOCATION: 1
<223> OTHER INFORMATION: Xaa is Arg linked to MPA

<400> SEQUENCE: 85

Xaa Asn Pro Gly Asn Gln Lys Glu Ala Pro Trp Leu Phe Thr Leu Asp
1               5                   10                  15
```

Glu Asn Phe Lys Ser Asp Leu Lys
            20

<210> SEQ ID NO 86
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Ala sub Cys
      and w Lys sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 86

Xaa Asn Pro Gly Asn Gln Lys Glu Ala Pro Trp Ala Phe Thr Leu Asp
1               5                   10                  15

Glu Asn Phe Lys Ser Asp Leu Lys
            20

<210> SEQ ID NO 87
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Val sub Cys
      and w Lys sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 87

Xaa Asn Pro Gly Asn Gln Lys Glu Ala Pro Trp Val Phe Thr Leu Asp
1               5                   10                  15

Glu Asn Phe Lys Ser Asp Leu Lys
            20

<210> SEQ ID NO 88
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Ile sub Cys
      and w Lys sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 88

Xaa Asn Pro Gly Asn Gln Lys Glu Ala Pro Trp Ile Phe Thr Leu Asp
1               5                   10                  15

Glu Asn Phe Lys Ser Asp Leu Lys
            20

<210> SEQ ID NO 89
<211> LENGTH: 24
<212> TYPE: PRT
<213> ORGANISM: Artificial Sequence
<220> FEATURE:
<223> OTHER INFORMATION: Synthetic Peptide
      Mod-Kr1(58-81 Active Zone w Leu sub Cys
      and w Lys sub Cys)frag
<220> FEATURE:

```
<221> NAME/KEY: VARIANT
<222> LOCATION: 1
<223> OTHER INFORMATION: Xaa is Arg linked to MPA-AEEA

<400> SEQUENCE: 89

Xaa Asn Pro Gly Asn Gln Lys Glu Ala Pro Trp Leu Phe Thr Leu Asp
1               5                   10                  15

Glu Asn Phe Lys Ser Asp Leu Lys
            20

<210> SEQ ID NO 90
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-81 Active Zone w Ala sub Cys
      and w Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
<222> LOCATION: 23
<223> OTHER INFORMATION: Xaa is Lys linked to N-epsilon-MPA

<400> SEQUENCE: 90

Xaa Pro Gly Asn Gln Lys Glu Ala Pro Trp Ala Phe Thr Leu Asp Glu
1               5                   10                  15

Asn Phe Lys Ser Asp Leu Xaa
            20

<210> SEQ ID NO 91
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-81 Active Zone w Val sub Cys
      and w Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
<222> LOCATION: 23
<223> OTHER INFORMATION: Xaa is Lys linked to N-epsilon-MPA

<400> SEQUENCE: 91

Xaa Pro Gly Asn Gln Lys Glu Ala Pro Trp Val Phe Thr Leu Asp Glu
1               5                   10                  15

Asn Phe Lys Ser Asp Leu Xaa
            20

<210> SEQ ID NO 92
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-81 Active Zone w Ile sub Cys
      and w Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
```

```
<222> LOCATION: 23
<223> OTHER INFORMATION: Xaa is Lys linked to N-epsilon-MPA

<400> SEQUENCE: 92

Xaa Pro Gly Asn Gln Lys Glu Ala Pro Trp Ile Phe Thr Leu Asp Glu
1               5                   10                  15

Asn Phe Lys Ser Asp Leu Xaa
            20

<210> SEQ ID NO 93
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-81 Active Zone w Leu sub Cys
      and w Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
<222> LOCATION: 23
<223> OTHER INFORMATION: Xaa is Lys linked to N-epsilon-MPA

<400> SEQUENCE: 93

Xaa Pro Gly Asn Gln Lys Glu Ala Pro Trp Leu Phe Thr Leu Asp Glu
1               5                   10                  15

Asn Phe Lys Ser Asp Leu Xaa
            20

<210> SEQ ID NO 94
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone w Ala sub Cys)frag
<220> FEATURE:
<221> NAME/KEY: VARIANT
<222> LOCATION: 1
<223> OTHER INFORMATION: Xaa is Arg linked to NAc

<400> SEQUENCE: 94

Xaa Asn Pro Gly Asn Gln Lys Glu Ala Pro Trp Ala Phe Thr Leu Asp
1               5                   10                  15

Glu Asn Phe Lys Ser Asp Leu
            20

<210> SEQ ID NO 95
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone w Val sub Cys)frag
<220> FEATURE:
<221> NAME/KEY: VARIANT
<222> LOCATION: 1
<223> OTHER INFORMATION: Xaa is Arg linked to NAc

<400> SEQUENCE: 95

Xaa Asn Pro Gly Asn Gln Lys Glu Ala Pro Trp Val Phe Thr Leu Asp
1               5                   10                  15

Glu Asn Phe Lys Ser Asp Leu
            20
```

<210> SEQ ID NO 96
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone w Ile sub Cys)frag
<220> FEATURE:
<221> NAME/KEY: VARIANT
<222> LOCATION: 1
<223> OTHER INFORMATION: Xaa is Arg linked to NAc

<400> SEQUENCE: 96

Xaa Asn Pro Gly Asn Gln Lys Glu Ala Pro Trp Ile Phe Thr Leu Asp
1               5                   10                  15

Glu Asn Phe Lys Ser Asp Leu
            20

<210> SEQ ID NO 97
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone w Leu sub Cys)frag
<220> FEATURE:
<221> NAME/KEY: VARIANT
<222> LOCATION: 1
<223> OTHER INFORMATION: Xaa is Arg linked to NAc

<400> SEQUENCE: 97

Xaa Asn Pro Gly Asn Gln Lys Glu Ala Pro Trp Leu Phe Thr Leu Asp
1               5                   10                  15

Glu Asn Phe Lys Ser Asp Leu
            20

<210> SEQ ID NO 98
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone w Ala sub Cys)frag
<220> FEATURE:
<221> NAME/KEY: VARIANT
<222> LOCATION: 1
<223> OTHER INFORMATION: Xaa is Arg linked to MPA

<400> SEQUENCE: 98

Xaa Asn Pro Gly Asn Gln Lys Glu Ala Pro Trp Ala Phe Thr Leu Asp
1               5                   10                  15

Glu Asn Phe Lys Ser Asp Leu
            20

<210> SEQ ID NO 99
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone w Val sub Cys)frag
<220> FEATURE:
<221> NAME/KEY: VARIANT
<222> LOCATION: 1
<223> OTHER INFORMATION: Xaa is Arg linked to MPA

<400> SEQUENCE: 99

Xaa Asn Pro Gly Asn Gln Lys Glu Ala Pro Trp Val Phe Thr Leu Asp

```
1               5                   10                  15

Glu Asn Phe Lys Ser Asp Leu
            20

<210> SEQ ID NO 100
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone w Ile sub Cys)frag
<220> FEATURE:
<221> NAME/KEY: VARIANT
<222> LOCATION: 1
<223> OTHER INFORMATION: Xaa is Arg linked to MPA

<400> SEQUENCE: 100

Xaa Asn Pro Gly Asn Gln Lys Glu Ala Pro Trp Ile Phe Thr Leu Asp
1               5                   10                  15

Glu Asn Phe Lys Ser Asp Leu
            20

<210> SEQ ID NO 101
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone w Leu sub Cys)frag
<220> FEATURE:
<221> NAME/KEY: VARIANT
<222> LOCATION: 1
<223> OTHER INFORMATION: Xaa is Arg linked to MPA

<400> SEQUENCE: 101

Xaa Asn Pro Gly Asn Gln Lys Glu Ala Pro Trp Leu Phe Thr Leu Asp
1               5                   10                  15

Glu Asn Phe Lys Ser Asp Leu
            20

<210> SEQ ID NO 102
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone)
<220> FEATURE:
<221> NAME/KEY: VARIANT
<222> LOCATION: 1
<223> OTHER INFORMATION: Xaa is Arg linked to MPA-AEEA

<400> SEQUENCE: 102

Xaa Asn Pro Gly Asn Gln Lys Glu Ala Pro Trp Ala Phe Thr Leu Asp
1               5                   10                  15

Glu Asn Phe Lys Ser Asp Leu
            20

<210> SEQ ID NO 103
<211> LENGTH: 23
<212> TYPE: PRT
<213> ORGANISM: Artificial Sequence
<220> FEATURE:
<223> OTHER INFORMATION: Synthetic Peptide
      Mod-Kr1(58-80 Active Zone)frag
<220> FEATURE:
<221> NAME/KEY: VARIANT
<222> LOCATION: 1
```

<223> OTHER INFORMATION: Xaa is Arg linked to MPA-AEEA

<400> SEQUENCE: 103

Xaa As

```
<221> NAME/KEY: VARIANT
<222> LOCATION: 1
<223> OTHER INFORMATION: Xaa is Arg linked to MPA

<400> SEQUENCE: 107

Xaa Asn Pro Gly Asn Gln Lys Glu Ala Pro Trp Lys
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic Peptide
      Mod-Kr1(58-69 Active Zone w Lys sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 108

Xaa Asn Pro Gly Asn Gln Lys Glu Ala Pro Trp Lys
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic Peptide
      Mod-Kr1(58-69 Active Zone w Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
<222> LOCATION: 12
<223> OTHER INFORMATION: Xaa is Lys linked to N-epsilon-MPA

<400> SEQUENCE: 109

Xaa Asn Pro Gly Asn Gln Lys Glu Ala Pro Trp Xaa
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic Peptide
      Mod-Kr1(58-68 Active Zone)frag
<220> FEATURE:
<221> NAME/KEY: VARIANT
<222> LOCATION: 1
<223> OTHER INFORMATION: Xaa is Arg linked to NAc

<400> SEQUENCE: 110

Xaa Asn Pro Gly Asn Gln Lys Glu Ala Pro Trp
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic Peptide
      Mod-Kr1(58-68 Active Zone)frag
<220> FEATURE:
<221> NAME/KEY: VARIANT
<222> LOCATION: 1
<223> OTHER INFORMATION: Xaa is Arg linked to MPA
```

```
<400> SEQUENCE: 111

Xaa Asn Pro Gly Asn Gln Lys Glu Ala Pro Trp
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic Peptide
      Mod-Kr1(58-68 Active Zone)frag
<220> FEATURE:
<221> NAME/KEY: VARIANT
<222> LOCATION: 1
<223> OTHER INFORMATION: Xaa is Arg linked to MPA-AEEA

<400> SEQUENCE: 112

Xaa Asn Pro Gly Asn Gln Lys Glu Ala Pro Trp
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic Peptide
      Mod-Kr1(70-81 Active Zone w Lys sub Cys)frag
<220> FEATURE:
<221> NAME/KEY: VARIANT
<222> LOCATION: 1
<223> OTHER INFORMATION: Xaa is Phe linked to NAc

<400> SEQUENCE: 113

Xaa Thr Leu Asp Glu Asn Phe Lys Ser Asp Leu Lys
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic Peptide
      Mod-Kr1(70-81 Active Zone w Lys sub Cys)frag
<220> FEATURE:
<221> NAME/KEY: VARIANT
<222> LOCATION: 1
<223> OTHER INFORMATION: Xaa is Phe linked to MPA

<400> SEQUENCE: 114

Xaa Thr Leu Asp Glu Asn Phe Lys Ser Asp Leu Lys
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Synthetic Peptide
      Mod-Kr1(70-81 Active Zone w Lys sub Cys)frag
<220> FEATURE:
<221> NAME/KEY: VARIANT
<222> LOCATION: 1
<223> OTHER INFORMATION: Xaa is Phe linked to MPA-AEEA

<400> SEQUENCE: 115

Xaa Thr Leu Asp Glu Asn Phe Lys Ser Asp Leu Lys
1               5                   10
```

```
<210> SEQ ID NO 116
<211> LENGTH: 12
<212> TYPE: PRT
<213> ORGANISM: Artificial Sequence
<220> FEATURE:
<223> OTHER INFORMATION: Synthetic Peptide
      Mod-Kr1(70-81 Active Zone w Lys sub Cys)frag
<220> FEATURE:
<221> NAME/KEY: VARIANT
<222> LOCATION: 1
<223> OTHER INFORMATION: Xaa is Phe linked to NAc
<220> FEATURE:
<221> NAME/KEY: VARIANT
<222> LOCATION: 12
<223> OTHER INFORMATION: Xaa is Lys linked to N-epsilon-MPA

<400> SEQUENCE: 116

Xaa Thr Leu Asp Glu Asn Phe Lys Ser Asp Leu Xaa
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic Peptide
      Mod-Kr1(70-80 Active Zone)frag
<220> FEATURE:
<221> NAME/KEY: VARIANT
<222> LOCATION: 1
<223> OTHER INFORMATION: Xaa is Phe linked to NAc

<400> SEQUENCE: 117

Xaa Thr Leu Asp Glu Asn Phe Lys Ser Asp Leu
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic Peptide
      Mod-Kr1(70-80 Active Zone)frag
<220> FEATURE:
<221> NAME/KEY: VARIANT
<222> LOCATION: 1
<223> OTHER INFORMATION: Xaa is Phe linked to MPA

<400> SEQUENCE: 118

Xaa Thr Leu Asp Glu Asn Phe Lys Ser Asp Leu
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic Peptide
      Mod-Kr1(70-80 Active Zone)frag
<220> FEATURE:
<221> NAME/KEY: VARIANT
<222> LOCATION: 1
<223> OTHER INFORMATION: Xaa is Phe linked to MPA-AEEA

<400> SEQUENCE: 119

Xaa Thr Leu Asp Glu Asn Phe Lys Ser Asp Leu
1               5                   10

<210> SEQ ID NO 120
<211> LENGTH: 10
<212> TYPE: PRT
```

```
<213> ORGANISM: Artificial Sequence
<220> FEATURE:
<223> OTHER INFORMATION: Synthetic Peptide
      Mod-Kr1(71-80 Active Zone)frag
<220> FEATURE:
<221> NAME/KEY: VARIANT
<222> LOCATION: 1
<223> OTHER INFORMATION: Xaa is Thr linked to NAc

<400> SEQUENCE: 120

Xaa Leu Asp Glu Asn Phe Lys Ser Asp Leu
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic Peptide
      Mod-Kr1(71-80 Active Zone)frag
<220> FEATURE:
<221> NAME/KEY: VARIANT
<222> LOCATION: 1
<223> OTHER INFORMATION: Xaa is Thr linked to MPA

<400> SEQUENCE: 121

Xaa Leu Asp Glu Asn Phe Lys Ser Asp Leu
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic Peptide
      Mod-Kr1(71-80 Active Zone)frag
<220> FEATURE:
<221> NAME/KEY: VARIANT
<222> LOCATION: 1
<223> OTHER INFORMATION: Xaa is Thr linked to MPA-AEEA

<400> SEQUENCE: 122

Xaa Leu Asp Glu Asn Phe Lys Ser Asp Leu
1               5                   10

<210> SEQ ID NO 123
<211> LENGTH: 9
<212> TYPE: PRT
<213> ORGANISM: Artificial Sequence
<220> FEATURE:
<223> OTHER INFORMATION: Synthetic Peptide
      Mod-Kr1(72-80 Active Zone)frag
<220> FEATURE:
<221> NAME/KEY: VARIANT
<222> LOCATION: 1
<223> OTHER INFORMATION: Xaa is Leu linked to NAc

<400> SEQUENCE: 123

Xaa Asp Glu Asn Phe Lys Ser Asp Leu
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic Peptide
      Mod-Kr1(72-80 Active Zone)frag
<220> FEATURE:
<221> NAME/KEY: VARIANT
<222> LOCATION: 1
```

```
<223> OTHER INFORMATION: Xaa is Leu linked to MPA

<400> SEQUENCE: 124

Xaa Asp Glu Asn Phe Lys Ser Asp Leu
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic Peptide
      Mod-Kr1(72-80 Active Zone)frag
<220> FEATURE:
<221> NAME/KEY: VARIANT
<222> LOCATION: 1
<223> OTHER INFORMATION: Xaa is Leu linked to MPA-AEEA

<400> SEQUENCE: 125

Xaa Asp Glu Asn Phe Lys Ser Asp Leu
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic Peptide
      Mod-Kr1(73-80 Active Zone)frag
<220> FEATURE:
<221> NAME/KEY: VARIANT
<222> LOCATION: 1
<223> OTHER INFORMATION: Xaa is Asp linked to NAc

<400> SEQUENCE: 126

Xaa Glu Asn Phe Lys Ser Asp Leu
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic Peptide
      Mod-Kr1(73-80 Active Zone)frag
<220> FEATURE:
<221> NAME/KEY: VARIANT
<222> LOCATION: 1
<223> OTHER INFORMATION: Xaa is Asp linked to MPA

<400> SEQUENCE: 127

Xaa Glu Asn Phe Lys Ser Asp Leu
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic Peptide
      Mod-Kr1(73-80 Active Zone)frag
<220> FEATURE:
<221> NAME/KEY: VARIANT
<222> LOCATION: 1
<223> OTHER INFORMATION: Xaa is Asp linked to MPA-AEEA

<400> SEQUENCE: 128

Xaa Glu Asn Phe Lys Ser Asp Leu
1               5
```

<210> SEQ ID NO 129
<211> LENGTH: 7
<212> TYPE: PRT
<213> ORGANISM: Artificial Sequence
<220> FEATURE:
<223> OTHER INFORMATION: Synthetic Peptide
     Mod-Kr1(73-79 Active Zone)frag
<220> FEATURE:
<221> NAME/KEY: VARIANT
<222> LOCATION: 1
<223> OTHER INFORMATION: Xaa is Asp linked to NAc

<400> SEQUENCE: 129

Xaa Glu Asn Phe Lys Ser Asp
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic Peptide
     Mod-Kr1(73-79 Active Zone)frag
<220> FEATURE:
<221> NAME/KEY: VARIANT
<222> LOCATION: 1
<223> OTHER INFORMATION: Xaa is Asp linked to MPA

<400> SEQUENCE: 130

Xaa Glu Asn Phe Lys Ser Asp
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic Peptide
     Mod-Kr1(73-79 Active Zone)frag
<220> FEATURE:
<221> NAME/KEY: VARIANT
<222> LOCATION: 1
<223> OTHER INFORMATION: Xaa is Asp linked to MPA-AEEA

<400> SEQUENCE: 131

Xaa Glu Asn Phe Lys Ser Asp
1               5

<210> SEQ ID NO 132
<211> LENGTH: 85
<212> TYPE: PRT
<213> ORGANISM: Artificial Sequence
<220> FEATURE:
<223> OTHER INFORMATION: Synthetic Peptide
     Kr2(1-85 Active Zone)frag
<220> FEATURE:
<221> NAME/KEY: VARIANT
<222> LOCATION: 1
<223> OTHER INFORMATION: Xaa is Gly is linked to NAc

<400> SEQUENCE: 132

Xaa Arg Tyr His Gln Cys Tyr Asn Gly Ser Gly Met Asp Tyr Arg Gly
1               5                   10                  15

Thr Ala Ser Thr Thr Lys Ser Gly His Gln Cys Gln Pro Trp Ala Leu
            20                  25                  30

Gln His Pro His Ser His His Leu Ser Ser Thr Asp Phe Pro Glu Leu
        35                  40                  45

Gly Gly Gly His Ala Tyr Cys Arg Asn Pro Gly Gly Gln Met Glu Gly

```
                  50                  55                  60
Pro Trp Cys Phe Thr Gln Asn Lys Asn Val Arg Met Glu Leu Cys Asp
65                  70                  75                  80

Val Pro Ser Cys Ser
                85

<210> SEQ ID NO 133
<211> LENGTH: 85
<212> TYPE: PRT
<213> ORGANISM: Artificial Sequence
<220> FEATURE:
<223> OTHER INFORMATION: Synthetic Peptide
      Kr2(1-85 Active Zone)frag
<220> FEATURE:
<221> NAME/KEY: VARIANT
<222> LOCATION: 1
<223> OTHER INFORMATION: Xaa is Gly is linked to MPA

<400> SEQUENCE: 133

Xaa Arg Tyr His Gln Cys Tyr Asn Gly Ser Gly Met Asp Tyr Arg Gly
1               5                   10                  15

Thr Ala Ser Thr Thr Lys Ser Gly His Gln Cys Gln Pro Trp Ala Leu
                20                  25                  30

Gln His Pro His Ser His His Leu Ser Ser Thr Asp Phe Pro Glu Leu
            35                  40                  45

Gly Gly Gly His Ala Tyr Cys Arg Asn Pro Gly Gly Gln Met Glu Gly
        50                  55                  60

Pro Trp Cys Phe Thr Gln Asn Lys Asn Val Arg Met Glu Leu Cys Asp
65                  70                  75                  80

Val Pro Ser Cys Ser
                85

<210> SEQ ID NO 134
<211> LENGTH: 85
<212> TYPE: PRT
<213> ORGANISM: Artificial Sequence
<220> FEATURE:
<223> OTHER INFORMATION: Synthetic Peptide
      Kr2(1-85 Active Zone)frag
<220> FEATURE:
<221> NAME/KEY: VARIANT
<222> LOCATION: 1
<223> OTHER INFORMATION: Xaa is Gly is linked to MPA-AEEA

<400> SEQUENCE: 134

Xaa Arg Tyr His Gln Cys Tyr Asn Gly Ser Gly Met Asp Tyr Arg Gly
1               5                   10                  15

Thr Ala Ser Thr Thr Lys Ser Gly His Gln Cys Gln Pro Trp Ala Leu
                20                  25                  30

Gln His Pro His Ser His His Leu Ser Ser Thr Asp Phe Pro Glu Leu
            35                  40                  45

Gly Gly Gly His Ala Tyr Cys Arg Asn Pro Gly Gly Gln Met Glu Gly
        50                  55                  60

Pro Trp Cys Phe Thr Gln Asn Lys Asn Val Arg Met Glu Leu Cys Asp
65                  70                  75                  80

Val Pro Ser Cys Ser
                85

<210> SEQ ID NO 135
<211> LENGTH: 24
<212> TYPE: PRT
<213> ORGANISM: Artificial Sequence
```

```
<220> FEATURE:
<223> OTHER INFORMATION: Synthetic Peptide
      Mod-Kr2(56-79 Active Zone w Ala sub Cys
      and Lys sub Cys)frag
<220> FEATURE:
<221> NAME/KEY: VARIANT
<222> LOCATION: 1
<223> OTHER INFORMATION: Xaa is Arg linked to NAc

<400> SEQUENCE: 135

Xaa Asn Pro Gly Gly Gln Met Glu Gly Pro Trp Ala Phe Thr Gln Asn
1               5                   10                  15

Lys Asn Val Arg Met Glu Leu Lys
            20

<210> SEQ ID NO 136
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Val sub Cys
      and Lys sub Cys)frag
<220> FEATURE:
<221> NAME/KEY: VARIANT
<222> LOCATION: 1
<223> OTHER INFORMATION: Xaa is Arg linked to NAc

<400> SEQUENCE: 136

Xaa Asn Pro Gly Gly Gln Met Glu Gly Pro Trp Val Phe Thr Gln Asn
1               5                   10                  15

Lys Asn Val Arg Met Glu Leu Lys
            20

<210> SEQ ID NO 137
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Ile sub Cys
      and Lys sub Cys)frag
<220> FEATURE:
<221> NAME/KEY: VARIANT
<222> LOCATION: 1
<223> OTHER INFORMATION: Xaa is Arg linked to NAc

<400> SEQUENCE: 137

Xaa Asn Pro Gly Gly Gln Met Glu Gly Pro Trp Ile Phe Thr Gln Asn
1               5                   10                  15

Lys Asn Val Arg Met Glu Leu Lys
            20

<210> SEQ ID NO 138
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Leu sub Cys
      and Lys sub Cys)frag
<220> FEATURE:
<221> NAME/KEY: VARIANT
<222> LOCATION: 1
<223> OTHER INFORMATION: Xaa is Arg linked to NAc

<400> SEQUENCE: 138

Xaa Asn Pro Gly Gly Gln Met Glu Gly Pro Trp Leu Phe Thr Gln Asn
1               5                   10                  15
```

Lys Asn Val Arg Met Glu Leu Lys
            20

<210> SEQ ID NO 139
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Ala sub Cys
      and Lys sub Cys)frag
<220> FEATURE:
<221> NAME/KEY: VARIANT
<222> LOCATION: 1
<223> OTHER INFORMATION: Xaa is Arg linked to MPA

<400> SEQUENCE: 139

Xaa Asn Pro Gly Gly Gln Met Glu Gly Pro Trp Ala Phe Thr Gln Asn
1               5                   10                  15

Lys Asn Val Arg Met Glu Leu Lys
            20

<210> SEQ ID NO 140
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Val sub Cys
      and Lys sub Cys)frag
<220> FEATURE:
<221> NAME/KEY: VARIANT
<222> LOCATION: 1
<223> OTHER INFORMATION: Xaa is Arg linked to MPA

<400> SEQUENCE: 140

Xaa Asn Pro Gly Gly Gln Met Glu Gly Pro Trp Val Phe Thr Gln Asn
1               5                   10                  15

Lys Asn Val Arg Met Glu Leu Lys
            20

<210> SEQ ID NO 141
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Ile sub Cys
      and Lys sub Cys)frag
<220> FEATURE:
<221> NAME/KEY: VARIANT
<222> LOCATION: 1
<223> OTHER INFORMATION: Xaa is Arg linked to MPA

<400> SEQUENCE: 141

Xaa Asn Pro Gly Gly Gln Met Glu Gly Pro Trp Ile Phe Thr Gln Asn
1               5                   10                  15

Lys Asn Val Arg Met Glu Leu Lys
            20

<210> SEQ ID NO 142
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Leu sub Cys
      and Lys sub Cys)frag

```
<220> FEATURE:
<221> NAME/KEY: VARIANT
<222> LOCATION: 1
<223> OTHER INFORMATION: Xaa is Arg linked to MPA

<400> SEQUENCE: 142

Xaa Asn Pro Gly Gly Gln Met Glu Gly Pro Trp Leu Phe Thr Gln Asn
1               5                   10                  15

Lys Asn Val Arg Met Glu Leu Lys
            20

<210> SEQ ID NO 143
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Ala sub Cys
      and Lys sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 143

Xaa Asn Pro Gly Gly Gln Met Glu Gly Pro Trp Ala Phe Thr Gln Asn
1               5                   10                  15

Lys Asn Val Arg Met Glu Leu Lys
            20

<210> SEQ ID NO 144
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Val sub Cys
      and Lys sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 144

Xaa Asn Pro Gly Gly Gln Met Glu Gly Pro Trp Val Phe Thr Gln Asn
1               5                   10                  15

Lys Asn Val Arg Met Glu Leu Lys
            20

<210> SEQ ID NO 145
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Ile sub Cys
      and Lys sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 145

Xaa Asn Pro Gly Gly Gln Met Glu Gly Pro Trp Ile Phe Thr Gln Asn
1               5                   10                  15

Lys Asn Val Arg Met Glu Leu Lys
            20
```

```
<210> SEQ ID NO 146
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Leu sub Cys
      and Lys sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 146

Xaa Asn Pro Gly Gly Gln Met Glu Gly Pro Trp Leu Phe Thr Gln Asn
1               5                   10                  15

Lys Asn Val Arg Met Glu Leu Lys
            20

<210> SEQ ID NO 147
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Ala sub Cys
      and Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
<222> LOCATION: 24
<223> OTHER INFORMATION: Xaa is Lys linked to N-epsilon-MPA

<400> SEQUENCE: 147

Xaa Asn Pro Gly Gly Gln Met Glu Gly Pro Trp Ala Phe Thr Gln Asn
1               5                   10                  15

Lys Asn Val Arg Met Glu Leu Xaa
            20

<210> SEQ ID NO 148
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Val sub Cys
      and Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
<222> LOCATION: 24
<223> OTHER INFORMATION: Xaa is Lys linked to N-epsilon-MPA

<400> SEQUENCE: 148

Xaa Asn Pro Gly Gly Gln Met Glu Gly Pro Trp Val Phe Thr Gln Asn
1               5                   10                  15

Lys Asn Val Arg Met Glu Leu Xaa
            20

<210> SEQ ID NO 149
<211> LENGTH: 24
<212> TYPE: PRT
<213> ORGANISM: Artificial Sequence
```

```
<220> FEATURE:
<223> OTHER INFORMATION: Synthetic Peptide
      Mod-Kr2(56-79 Active Zone w Ile sub Cys
      and Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
<222> LOCATION: 24
<223> OTHER INFORMATION: Xaa is Lys linked to N-epsilon-MPA

<400> SEQUENCE: 149

Xaa Asn Pro Gly Gly Gln Met Glu Gly Pro Trp Ile Phe Thr Gln Asn
1               5                   10                  15

Lys Asn Val Arg Met Glu Leu Xaa
            20

<210> SEQ ID NO 150
<211> LENGTH: 24
<212> TYPE: PRT
<213> ORGANISM: Artificial Sequence
<220> FEATURE:
<223> OTHER INFORMATION: Synthetic Peptide
      Mod-Kr2(56-79 Active Zone w Leu sub Cys
      and Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
<222> LOCATION: 24
<223> OTHER INFORMATION: Xaa is Lys linked to N-epsilon-MPA

<400> SEQUENCE: 150

Xaa Asn Pro Gly Gly Gln Met Glu Gly Pro Trp Leu Phe Thr Gln Asn
1               5                   10                  15

Lys Asn Val Arg Met Glu Leu Xaa
            20

<210> SEQ ID NO 151
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Ala sub Cys)frag
<220> FEATURE:
<221> NAME/KEY: VARIANT
<222> LOCATION: 1
<223> OTHER INFORMATION: Xaa is Arg linked to NAc

<400> SEQUENCE: 151

Xaa Asn Pro Gly Gly Gln Met Glu Gly Pro Trp Ala Phe Thr Gln Asn
1               5                   10                  15

Lys Asn Val Arg Met Glu Leu
            20

<210> SEQ ID NO 152
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Val sub Cys)frag
<220> FEATURE:
<221> NAME/KEY: VARIANT
<222> LOCATION: 1
```

<223> OTHER INFORMATION: Xaa is Arg linked to NAc

<400> SEQUENCE: 152

Xaa Asn Pro Gly Gly Gln Met Glu Gly Pro Trp Val Phe Thr Gln Asn
1               5                   10                  15

Lys Asn Val Arg Met Glu Leu
            20

<210> SEQ ID NO 153
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Ile sub Cys)frag
<220> FEATURE:
<221> NAME/KEY: VARIANT
<222> LOCATION: 1
<223> OTHER INFORMATION: Xaa is Arg linked to NAc

<400> SEQUENCE: 153

Xaa Asn Pro Gly Gly Gln Met Glu Gly Pro Trp Ile Phe Thr Gln Asn
1               5                   10                  15

Lys Asn Val Arg Met Glu Leu
            20

<210> SEQ ID NO 154
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Leu sub Cys)frag
<220> FEATURE:
<221> NAME/KEY: VARIANT
<222> LOCATION: 1
<223> OTHER INFORMATION: Xaa is Arg linked to NAc

<400> SEQUENCE: 154

Xaa Asn Pro Gly Gly Gln Met Glu Gly Pro Trp Leu Phe Thr Gln Asn
1               5                   10                  15

Lys Asn Val Arg Met Glu Leu
            20

<210> SEQ ID NO 155
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Ala sub Cys)frag
<220> FEATURE:
<221> NAME/KEY: VARIANT
<222> LOCATION: 1
<223> OTHER INFORMATION: Xaa is Arg linked to MPA

<400> SEQUENCE: 155

Xaa Asn Pro Gly Gly Gln Met Glu Gly Pro Trp Ala Phe Thr Gln Asn
1               5                   10                  15

Lys Asn Val Arg Met Glu Leu
            20

<210> SEQ ID NO 156
<211> LENGTH: 23
<212> TYPE: PRT
<213> ORGANISM: Artificial Sequence
<220> FEATURE:

<223> OTHER INFORMATION: Synthetic Peptide
      Mod-Kr2(56-78 Active Zone w Val sub Cys)frag
<220> FEATURE:
<221> NAME/KEY: VARIANT
<222> LOCATION: 1
<223> OTHER INFORMATION: Xaa is Arg linked to MPA

<400> SEQUENCE: 156

Xaa Asn Pro Gly Gly Gln Met Glu Gly Pro Trp Val Phe Thr Gln Asn
1               5                   10                  15

Lys Asn Val Arg Met Glu Leu
            20

<210> SEQ ID NO 157
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Ile sub Cys)frag
<220> FEATURE:
<221> NAME/KEY: VARIANT
<222> LOCATION: 1
<223> OTHER INFORMATION: Xaa is Arg linked to MPA

<400> SEQUENCE: 157

Xaa Asn Pro Gly Gly Gln Met Glu Gly Pro Trp Ile Phe Thr Gln Asn
1               5                   10                  15

Lys Asn Val Arg Met Glu Leu
            20

<210> SEQ ID NO 158
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Leu sub Cys)frag
<220> FEATURE:
<221> NAME/KEY: VARIANT
<222> LOCATION: 1
<223> OTHER INFORMATION: Xaa is Arg linked to MPA

<400> SEQUENCE: 158

Xaa Asn Pro Gly Gly Gln Met Glu Gly Pro Trp Leu Phe Thr Gln Asn
1               5                   10                  15

Lys Asn Val Arg Met Glu Leu
            20

<210> SEQ ID NO 159
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Ala sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 159

Xaa Asn Pro Gly Gly Gln Met Glu Gly Pro Trp Ala Phe Thr Gln Asn
1               5                   10                  15

Lys Asn Val Arg Met Glu Leu
            20

-continued

```
<210> SEQ ID NO 160
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Val sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 160

Xaa Asn Pro Gly Gly Gln Met Glu Gly Pro Trp Val Phe Thr Gln Asn
1               5                   10                  15

Lys Asn Val Arg Met Glu Leu
            20

<210> SEQ ID NO 161
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Ile sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 161

Xaa Asn Pro Gly Gly Gln Met Glu Gly Pro Trp Ile Phe Thr Gln Asn
1               5                   10                  15

Lys Asn Val Arg Met Glu Leu
            20

<210> SEQ ID NO 162
<211> LENGTH: 23
<212> TYPE: PRT
<213> ORGANISM: Artificial Sequence
<220> FEATURE:
<223> OTHER INFORMATION: Synthetic Peptide
      Mod-Kr2(56-78 Active Zone w Leu sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 162

Xaa Asn Pro Gly Gly Gln Met Glu Gly Pro Trp Leu Phe Thr Gln Asn
1               5                   10                  15

Lys Asn Val Arg Met Glu Leu
            20

<210> SEQ ID NO 163
<211> LENGTH: 12
<212> TYPE: PRT
<213> ORGANISM: Artificial Sequence
<220> FEATURE:
<223> OTHER INFORMATION: Synthetic Peptide
      Mod-Kr2(56-67 Active Zone w Lys sub Cys)frag
<220> FEATURE:
<221> NAME/KEY: VARIANT
<222> LOCATION: 1
<223> OTHER INFORMATION: Xaa is Arg linked to NAc

<400> SEQUENCE: 163

Xaa Asn Pro Gly Gly Gln Met Glu Gly Pro Trp Lys
1               5                   10
```

-continued

```
<210> SEQ ID NO 164
<211> LENGTH: 12
<212> TYPE: PRT
<213> ORGANISM: Artificial Sequence
<220> FEATURE:
<223> OTHER INFORMATION: Synthetic Peptide
      Mod-Kr2(56-67 Active Zone w Lys sub Cys)frag
<220> FEATURE:
<221> NAME/KEY: VARIANT
<222> LOCATION: 1
<223> OTHER INFORMATION: Xaa is Arg linked to MPA

<400> SEQUENCE: 164

Xaa Asn Pro Gly Gly Gln Met Glu Gly Pro Trp Lys
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic Peptide
      Mod-Kr2(56-67 Active Zone w Lys sub Cys)frag
<220> FEATURE:
<221> NAME/KEY: VARIANT
<222> LOCATION: 1
<223> OTHER INFORMATION: Xaa is Arg linked to MPA-AEEA

<400> SEQUENCE: 165

Xaa Asn Pro Gly Gly Gln Met Glu Gly Pro Trp Lys
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Synthetic Peptide
      Mod-Kr2(56-67 Active Zone w Lys sub Cys)frag
<220> FEATURE:
<221> NAME/KEY: VARIANT
<222> LOCATION: 1
<223> OTHER INFORMATION: Xaa is Arg linked to NAc
<220> FEATURE:
<221> NAME/KEY: VARIANT
<222> LOCATION: 12
<223> OTHER INFORMATION: Xaa is Lys linked to N-epsilon-MPA

<400> SEQUENCE: 166

Xaa Asn Pro Gly Gly Gln Met Glu Gly Pro Trp Xaa
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Synthetic Peptide
      Mod-Kr2(56-66 Active Zone)frag
<220> FEATURE:
<221> NAME/KEY: VARIANT
<222> LOCATION: 1
<223> OTHER INFORMATION: Xaa is Arg linked to NAc

<400> SEQUENCE: 167

Xaa Asn Pro Gly Gly Gln Met Glu Gly Pro Trp
1               5                   10

<210> SEQ ID NO 168
```

```
<211> LENGTH: 11
<212> TYPE: PRT
<213> ORGANISM: Artificial Sequence
<220> FEATURE:
<223> OTHER INFORMATION: Synthetic Peptide
      Mod-Kr2(56-66 Active Zone)frag
<220> FEATURE:
<221> NAME/KEY: VARIANT
<222> LOCATION: 1
<223> OTHER INFORMATION: Xaa is Arg linked to MPA

<400> SEQUENCE: 168

Xaa Asn Pro Gly Gly Gln Met Glu Gly Pro Trp
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Synthetic Peptide
      Mod-Kr2(56-66 Active Zone)frag
<220> FEATURE:
<221> NAME/KEY: VARIANT
<222> LOCATION: 1
<223> OTHER INFORMATION: Xaa is Arg linked to MPA-AEEA

<400> SEQUENCE: 169

Xaa Asn Pro Gly Gly Gln Met Glu Gly Pro Trp
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Synthetic Peptide
      Mod-Kr2(68-79 Active Zone w Lys sub Cys)frag
<220> FEATURE:
<221> NAME/KEY: VARIANT
<222> LOCATION: 1
<223> OTHER INFORMATION: Xaa is Phe linked to NAc

<400> SEQUENCE: 170

Xaa Thr Gln Asn Lys Asn Val Arg Met Glu Leu Lys
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Synthetic Peptide
      Mod-Kr2(68-79 Active Zone w Lys sub Cys)frag
<220> FEATURE:
<221> NAME/KEY: VARIANT
<222> LOCATION: 1
<223> OTHER INFORMATION: Xaa is Phe linked to MPA

<400> SEQUENCE: 171

Xaa Thr Gln Asn Lys Asn Val Arg Met Glu Leu Lys
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Synthetic Peptide
      Mod-Kr2(68-79 Active Zone w Lys sub Cys)frag
<220> FEATURE:
```

```
<221> NAME/KEY: VARIANT
<222> LOCATION: 1
<223> OTHER INFORMATION: Xaa is Phe linked to MPA-AEEA

<400> SEQUENCE: 172

Xaa Thr Gln Asn Lys Asn Val Arg Met Glu Leu Lys
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Synthetic Peptide
      Mod-Kr2(68-79 Active Zone w Lys sub Cys)frag
<220> FEATURE:
<221> NAME/KEY: VARIANT
<222> LOCATION: 1
<223> OTHER INFORMATION: Phe is NAc-Phe
<220> FEATURE:
<221> NAME/KEY: VARIANT
<222> LOCATION: 12
<223> OTHER INFORMATION: Xaa is Lys linked to N-epsilon-MPA

<400> SEQUENCE: 173

Xaa Thr Gln Asn Lys Asn Val Arg Met Glu Leu Xaa
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Synthetic Peptide
      Mod-Kr2(68-78 Active Zone)frag
<220> FEATURE:
<221> NAME/KEY: VARIANT
<222> LOCATION: 1
<223> OTHER INFORMATION: Xaa is Phe linked to NAc

<400> SEQUENCE: 174

Xaa Thr Gln Asn Lys Asn Val Arg Met Glu Leu
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Synthetic Peptide
      Mod-Kr2(68-78 Active Zone)frag
<220> FEATURE:
<221> NAME/KEY: VARIANT
<222> LOCATION: 1
<223> OTHER INFORMATION: Xaa is Phe linked to MPA

<400> SEQUENCE: 175

Xaa Thr Gln Asn Lys Asn Val Arg Met Glu Leu
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Synthetic Peptide
      Mod-Kr2(68-78 Active Zone)frag
<220> FEATURE:
<221> NAME/KEY: VARIANT
<222> LOCATION: 1
<223> OTHER INFORMATION: Xaa is Phe linked to MPA-AEEA
```

```
<400> SEQUENCE: 176

Xaa Thr Gln Asn Lys Asn Val Arg Met Glu Leu
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Synthetic Peptide
      Mod-Kr2(69-78 Active Zone)frag
<220> FEATURE:
<221> NAME/KEY: VARIANT
<222> LOCATION: 1
<223> OTHER INFORMATION: Xaa is Thr linked to NAc

<400> SEQUENCE: 177

Xaa Gln Asn Lys Asn Val Arg Met Glu Leu
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Synthetic Peptide
      Mod-Kr2(69-78 Active Zone)frag
<220> FEATURE:
<221> NAME/KEY: VARIANT
<222> LOCATION: 1
<223> OTHER INFORMATION: Xaa is Thr linked to MPA

<400> SEQUENCE: 178

Xaa Gln Asn Lys Asn Val Arg Met Glu Leu
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Synthetic Peptide
      Mod-Kr2(69-78 Active Zone)frag
<220> FEATURE:
<221> NAME/KEY: VARIANT
<222> LOCATION: 1
<223> OTHER INFORMATION: Xaa is Thr linked to MPA-AEEA

<400> SEQUENCE: 179

Xaa Gln Asn Lys Asn Val Arg Met Glu Leu
1               5                   10

<210> SEQ ID NO 180
<211> LENGTH: 9
<212> TYPE: PRT
<213> ORGANISM: Artificial Sequence
<220> FEATURE:
<223> OTHER INFORMATION: Synthetic Peptide
      Mod-Kr2(70-78 Active Zone)frag
<220> FEATURE:
<221> NAME/KEY: VARIANT
<222> LOCATION: 1
<223> OTHER INFORMATION: Xaa is Gln linked to NAc

<400> SEQUENCE: 180

Xaa Asn Lys Asn Val Arg Met Glu Leu
1               5
```

```
<210> SEQ ID NO 181
<211> LENGTH: 9
<212> TYPE: PRT
<213> ORGANISM: Artificial Sequence
<220> FEATURE:
<223> OTHER INFORMATION: Synthetic Peptide
      Mod-Kr2(70-78 Active Zone)frag
<220> FEATURE:
<221> NAME/KEY: VARIANT
<222> LOCATION: 1
<223> OTHER INFORMATION: Xaa is Gln linked to MPA

<400> SEQUENCE: 181

Xaa Asn Lys Asn Val Arg Met Glu Leu
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Peptide
      Mod-Kr2(70-78 Active Zone)frag
<220> FEATURE:
<221> NAME/KEY: VARIANT
<222> LOCATION: 1
<223> OTHER INFORMATION: Xaa is Gln linked to MPA-AEEA

<400> SEQUENCE: 182

Xaa Asn Lys Asn Val Arg Met Glu Leu
1               5

<210> SEQ ID NO 183
<211> LENGTH: 8
<212> TYPE: PRT
<213> ORGANISM: Artificial Sequence
<220> FEATURE:
<223> OTHER INFORMATION: Synthetic Peptide
      Mod-Kr2(70-77 Active Zone)frag
<220> FEATURE:
<221> NAME/KEY: VARIANT
<222> LOCATION: 1
<223> OTHER INFORMATION: Xaa is Gln linked to NAc

<400> SEQUENCE: 183

Xaa Asn Lys Asn Val Arg Met Glu
1               5

<210> SEQ ID NO 184
<211> LENGTH: 8
<212> TYPE: PRT
<213> ORGANISM: Artificial Sequence
<220> FEATURE:
<223> OTHER INFORMATION: Synthetic Peptide
      Mod-Kr2(70-77 Active Zone)frag
<220> FEATURE:
<221> NAME/KEY: VARIANT
<222> LOCATION: 1
<223> OTHER INFORMATION: Xaa is Gln linked to MPA

<400> SEQUENCE: 184

Xaa Asn Lys Asn Val Arg Met Glu
1               5

<210> SEQ ID NO 185
<211> LENGTH: 8
<212> TYPE: PRT
<213> ORGANISM: Artificial Sequence
<220> FEATURE:
<223> OTHER INFORMATION: Synthetic Peptide
      Mod-Kr2(70-77 Active Zone)frag
```

```
<220> FEATURE:
<221> NAME/KEY: VARIANT
<222> LOCATION: 1
<223> OTHER INFORMATION: Xaa is Gln linked to MPA-AEEA

<400> SEQUENCE: 185

Xaa Asn Lys Asn Val Arg Met Glu
1               5

<210> SEQ ID NO 186
<211> LENGTH: 93
<212> TYPE: PRT
<213> ORGANISM: Artificial Sequence
<220> FEATURE:
<223> OTHER INFORMATION: Synthetic Peptide
      Mod-Kr1(1-93 Active Zone)frag
<220> FEATURE:
<221> NAME/KEY: VARIANT
<222> LOCATION: 1
<223> OTHER INFORMATION: Xaa is Gly linked to NAc

<400> SEQUENCE: 186

Xaa Ser Asn Lys Asn His Lys Cys Tyr Asn Ser Thr Gly Val Asp Tyr
1               5                   10                  15

Arg Gly Thr Val Ser Val Thr Lys Ser Gly Arg Gln Cys Gln Pro Trp
            20                  25                  30

Asn Ser Gln Tyr Pro His Thr His Thr Phe Thr Ala Leu Arg Phe Pro
        35                  40                  45

Glu Leu Asn Gly Gly His Ser Tyr Cys Arg Asn Pro Gly Asn Gln Lys
    50                  55                  60

Glu Ala Pro Trp Cys Phe Thr Leu Asp Glu Asn Phe Lys Ser Asp Leu
65                  70                  75                  80

Cys Asp Ile Pro Ala Cys Asp Ser Lys Asp Ser Asp Ile
                85                  90

<210> SEQ ID NO 187
<211> LENGTH: 93
<212> TYPE: PRT
<213> ORGANISM: Artificial Sequence
<220> FEATURE:
<223> OTHER INFORMATION: Synthetic Peptide
      Mod-Kr1(1-93 Active Zone)frag
<220> FEATURE:
<221> NAME/KEY: VARIANT
<222> LOCATION: 1
<223> OTHER INFORMATION: Xaa is Gly linked to MPA

<400> SEQUENCE: 187

Xaa Ser Asn Lys Asn His Lys Cys Tyr Asn Ser Thr Gly Val Asp Tyr
1               5                   10                  15

Arg Gly Thr Val Ser Val Thr Lys Ser Gly Arg Gln Cys Gln Pro Trp
            20                  25                  30

Asn Ser Gln Tyr Pro His Thr His Thr Phe Thr Ala Leu Arg Phe Pro
        35                  40                  45

Glu Leu Asn Gly Gly His Ser Tyr Cys Arg Asn Pro Gly Asn Gln Lys
    50                  55                  60

Glu Ala Pro Trp Cys Phe Thr Leu Asp Glu Asn Phe Lys Ser Asp Leu
65                  70                  75                  80

Cys Asp Ile Pro Ala Cys Asp Ser Lys Asp Ser Asp Ile
                85                  90

<210> SEQ ID NO 188
<211> LENGTH: 93
```

```
<212> TYPE: PRT
<213> ORGANISM: Artificial Sequence
<220> FEATURE:
<223> OTHER INFORMATION: Synthetic Peptide
      Mod-Kr1(1-93 Active Zone)frag
<220> FEATURE:
<221> NAME/KEY: VARIANT
<222> LOCATION: 1
<223> OTHER INFORMATION: Xaa is Gly linked to MPA-AEEA

<400> SEQUENCE: 188

Xaa Ser Asn Lys Asn His Lys Cys Tyr Asn Ser Thr Gly Val Asp Tyr
1               5                   10                  15

Arg Gly Thr Val Ser Val Thr Lys Ser Gly Arg Gln Cys Gln Pro Trp
            20                  25                  30

Asn Ser Gln Tyr Pro His Thr His Thr Phe Thr Ala Leu Arg Phe Pro
        35                  40                  45

Glu Leu Asn Gly Gly His Ser Tyr Cys Arg Asn Pro Gly Asn Gln Lys
    50                  55                  60

Glu Ala Pro Trp Cys Phe Thr Leu Asp Glu Asn Phe Lys Ser Asp Leu
65                  70                  75                  80

Cys Asp Ile Pro Ala Cys Asp Ser Lys Asp Ser Asp Ile
                85                  90

<210> SEQ ID NO 189
<211> LENGTH: 91
<212> TYPE: PRT
<213> ORGANISM: Artificial Sequence
<220> FEATURE:
<223> OTHER INFORMATION: Synthetic Peptide
      K5(1-91 Active Zone)frag

<400> SEQUENCE: 189

Gly Ser Ser Glu Glu Asp Cys Met Phe Gly Asn Gly Lys Gly Tyr Arg
1               5                   10                  15

Gly Lys Arg Ala Thr Thr Val Thr Gly Thr Pro Cys Gln Asp Trp Ala
            20                  25                  30

Ala Gln Glu Pro His Arg His Ser Ile Phe Thr Pro Glu Thr Asn Pro
        35                  40                  45

Arg Ala Gly Leu Glu Lys Asn Tyr Cys Arg Asn Pro Asp Gly Asp Val
    50                  55                  60

Gly Gly Pro Trp Cys Tyr Thr Thr Asn Pro Arg Lys Leu Tyr Asp Tyr
65                  70                  75                  80

Cys Asp Val Pro Gln Cys Ala Ala Pro Asp Ile
                85                  90
```

US 10,905,750 B2

GRP78 ANTAGONIST THAT BLOCK BINDING OF RECEPTOR TYROSINE KINASE ORPHAN RECEPTORS AS IMMUNOTHERAPY ANTICANCER AGENTS

CROSS-REFERENCE TO RELATED APPLICATIONS

This application claims priority from U.S. provisional patent application No. 62/584,564 filed Nov. 10, 2017, which is incorporated by reference as if fully set forth herein.

TECHNICAL FIELD

The present invention relates generally to the area of immunomodulation of immune cells (tolerogenic dendritic cells) and the induced apoptosis of tumor cells and endothelial cells by using GRP78 antagonists. More particularly the present invention relates to peptide fragments and fusion composites having kringle like sequences. These GRP78 antagonists block or at least hinder GRP78 from binding to receptor tyrosine kinase orphan receptors (RORs) and inhibit RORs activity. In particular, the invention relates to compositions and methods for modulating or interfering with GRP78 binding to the kringle domains of RORs whereby producing immunomodulatory effects on dendritic cells, anti-angiogenic effects on activated endothelial cells and apoptotic effects on cancer cells.

BACKGROUND OF THE INVENTION

The process by which new blood vessels are formed, i.e., angiogenesis, is a highly regulated and essential process of controlling the growth of the primary cells of capillary blood vessels (i.e., endothelial cells). Angiogenesis is believed to involve a highly complex interaction of a number of different cell types and different molecules that regulate endothelial cell growth and is essential for reproduction, development and wound repair. Under non-stress conditions, these cells and molecules maintain the vascular system in a quiescent state for extended periods. However, during stress conditions such as during wound repair, these same systems of cells and molecules undergo rapid proliferation and turnover within relatively short periods of time. Even though angiogenesis is a highly regulated and complex biological process under normal conditions, a number of diseases associated with unregulated angiogenesis. Unregulated angiogenesis can either cause a particular angiogenic type disease directly or indirectly aggravate an existing pathological condition. Cancerous tumor growth and metastasis are well known to be associated with angiogenesis.

For example, the kringle 5 region of plasminogen and various other kringle 5 region peptides are of particular interest in that they have been shown to interfere with the angiogenic processes and are thus believed to be capable of inhibiting angiogenesis. The usefulness of these anti-angiogenic kringle 5 region peptides is limited due to their relatively rapid in vivo degradation via kidney excretion, liver metabolism, and decomposition from endogeneous peptidases which lead to relatively very short half-lives. Accordingly, to achieve an effective therapy, these anti-angiogenic kringle 5 region peptides would have to be constantly infused into the patient in order to achieve adequate plasma levels for treating angiogenesis related diseases in mammals.

GRP78 mostly resides in the endoplasmic reticulum (ER), where it functions in protein folding and assembly, targeting misfolded protein for degradation, ER $Ca^{2+}$-binding and controlling the activation of trans-membrane ER stress sensors. GRP78 is a member of the 70 kilodalton heat shock protein (HSP70) family, and its up-regulation is part of the general cellular defense mechanism of stressed cells that is referred to as the unfolded protein response.

The expression of GRP78 and other members of the unfolded protein response in tumors has led to a significant scientific interest in targeting members of the unfolded protein response in cancer. Overexpression of GRP78 in many different cancers has established that GRP78 contributes to tumor growth and confers drug resistance to cancer cells. Accordingly soluble GRP78 and cell surface bound GRP78 are possible biomarkers and therapeutic targets for many cancers including glioblastoma. GRP78 has also been found to be released at times of cellular stress and has been shown to have extracellular properties that are anti-inflammatory or favor the resolution of inflammation. GRP78 produced by the tumor cells is believed to interfer with adaptive immune responses of antigen-presenting cells (APCs). Soluble GRP78 is believed to bind to membrane bound RORs of the APCs which induces of self-tolerance of APCs which helps explain how tumors can remain invisible from immune surveillance (FIG. 1). For example, patients with glioblastoma exhibit extreme immunosuppression, both systemically as well as within the tumor microenvironment. We now know that there are many factors produced by the tumor and tolerogenic immune cells that can induce immune tolerance and tumor resistance that are not inhibited by current therapies. For example, tumor derived soluble GRP78 can bind to immature dendritic cells (DCs) and regulate their maturation to produce a tolerogenic phenotype by upregulating IL-10, B7H1, B7H3, and B7H4 expression and down regulating maturity marker expression of CD86 leading to a tolerogenic phenotype that is stable with LPS stimulation. This immunosuppressive DC phenotype is stable upon lipopolysaccharide (LPS) stimulation. GRP78-treated dendritic cells also reduce T-cell proliferation and induce T-cell apoptosis. Finally, increased generation of T-regs from GRP78 treated myeloid antigen presenting cells were observed in vitro and ex vivo. This data shows that GRP78 surface binding on tumor cells leads to chemo-resistance and proliferation and suggest that GRP78 is a soluble immunomodulatory molecule.

To understand how GRP78 binding can lead to dendritic cell tolerance and tumor chemo-resistance, we have used pull down experiments to identify the surface binding protein. We have discovered that soluble GRP78 binds to a cell surface orphan tyrosine kinase receptors (RORs) on dendritic, glioma, and endothelial cells (FIG. 1). We have also discovered that our novel peptide GRP78 antagonists can reverse this tolerogenic and resistant phenotype. Our data demonstrates that GRP78 binds to the kringle domain of RORs leading to ROR signaling through several different non-canonical pathways. This ROR signaling in dendritic cells induces a tolerogenic phenotype and a resistant phenotype in tumor cells. Wnt5a has been shown to be a second ligand for ROR and binds to the frizzled domain, which leads to increased migration and proliferation of leukemia cells. We have shown that by blocking the GRP78 binding to ROR, the Wnt5a binding does not lead to activation of ROR.

Receptor tyrosine kinase orphan receptors (RORs) are transmembrane tyrosine kinase peptides that belong to a family of orphan receptor kinases in mammals that consist of two members ROR1 and ROR2. ROR1 consists of (1) a Ig-like domain (Ig), (2) a frizzled domain (FZD), (3) a kringle domain (KRD), (4) a transmembrane, and (5) a TKD-like tyrosine kinase domain (FIG. 2). The highest expression of ROR1 in tissues that are not in a tumor microenvironment, is during early embryonic development and that this expression of ROR1 drops strongly around day 16, with only very low expression levels observed in adult tissues. Mice with homozygous disruption in the ROR1 gene die within 24 hours after birth from respiratory defects.

In a tumor microenvironment, ROR1 can be found on the leukemia cells of patients with chronic lymphocytic leukemia, and either ROR1 or ROR2 is expressed by neoplastic cells of a variety of different cancers including glioblastoma. Cancer-cell expression of ROR1 has been associated with enhanced cancer-cell migration, epithelial mesenchymal transition, increased associated risk for relapse and metastasis, and unfavorable prognosis. More recently, ROR1 has been identified on ovarian cancer stem cells, which have enhanced capacity for migration/spheroid formation in vitro and engraftment/metastasis in vivo. ROR1 may function as a receptor for Wnt5a that induces noncanonical Wnt signaling which then potentially leads to enhanced tumor-cell growth, directional migration, and/or tissue-cell polarity during organogenesis. We have found that ROR1 is a receptor for tumor expressed soluble GRP78 on activated endothelial cells, stressed tumor cells and immature dendritic cells. The binding to GRP78 to the kringle domain on ROR1 leads to a cascade of signaling that can induce angiogenesis, chemo-resistance and dendritic cell tolerance (FIG. 1).

Thus, there is a need for compounds and methods that are useful in treating angiogenic diseases in mammals. More specifically, there is a need for compounds and methods that can reduce or reverse the tolerogenic phenotype of dendritic cells and reduce or reverse resistance to induce cell apoptosis with our GRP78 antagonists. More specifically, there is a need for angiogenesis inhibitors which are safe for therapeutic use and which exhibit selective toxicity with respect to the pathological condition such as by selectively inhibiting the proliferation of endothelial cells while exhibiting no or a low degree of toxicity to normal (ie. non-cancerous) cells. Such compounds should also be easily and cost-effectively made.

SUMMARY

The present invention is directed to GRP78 antagonists, more particularly to anti-angiogenic kringle fragment peptides from mammalian plasminogen, ROR1, and or ROR2. These kringle fragment peptides may be in the form of free kringle fragments peptides, or in a form fused onto immunoglobulin, or in a form modified with various linking agents that are designed to bind to blood or tissue peptides when introduced into the blood stream of a patient. These kringle fragments fused to immunoglobulin compound and the modified kringle fragments realize extended in vivo half-life times as compared to their corresponding non-modified kringle fragment peptides. These modified kringle fragment peptides include succimidyl or maleimido reactive linking groups which can then subsequently react with amino groups, hydroxyl groups and/or thiol groups of blood or tissue peptides to form the more stable biologically active components. The present invention also includes a method for treating a patient in need of antiangiogenesis therapy comprising administering these kringle containing antiangiogenic peptides to the patient. The present invention also includes compositions for treating a patient in need of anti-angiogenesis therapy comprising a compound containing at lease one of these kringle containing antiangiogenic peptides with a pharmaceutically acceptable excipient and/or optionally sustained release compounds to form a therapeutic composition.

This disclosure identifies three broadly defined different types of GRP78 antagonists that specifically inhibit surface bound GRP78 binding and receptor signaling. These broadly defined different grouping of GRP78 antagonists include (1) plasminogen kringle 5 fragment fusion compounds, (2) ROR1 kringle derivative compounds, and (3) ROR2 kringle derivative compounds.

This first type of GRP78 antagonists that are disclosed in the present application are the plasminogen kringle five fragment fusion compound includes various peptide fragments of K5 (SEQ ID NO: 189) fused to immunoglobulin herein abbreviated as the K5-frag-Fc fusion peptides. These K5-frag-Fc fusion peptides of the first type of GRP78 antagonists include but not limited to those selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

The second type of GRP78 antagonists that are disclosed in the present application are the ROR1 kringle derivatives that include the kringle active zone component itself (SEQ ID NO: 19) abbreviated as Kr1 or specifically the Kr1(1-93 Active Zone) fragment; Kr1 active zone fragment peptides here abbreviated as Kr1-frag peptides; Kr1 active zone fragment peptides fusion complexes herein abbreviated as Kr1-frag-Fc; and the modified active zone fragments of Kr1 herein abbreviated as mod-Kr1-frag peptides.

The Kr1-frag-Fc fusion peptides of the second type of GRP78 antagonists include but not limited to those selected from the group consisting of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, and SEQ ID NO:32.

The Kr1-frag peptides of the second type of GRP78 antagonists include but not limited to those selected from the group consisting of SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61.

The mod-Kr1-frag peptides of the second type of GRP78 antagonists include but not limited to those selected from the group consisting of SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:186, SEQ ID NO:187, and SEQ ID NO:188.

The third type of GRP78 antagonists that are disclosed in the present application are the ROR2 kringle derivatives that include SEQ ID NO:33 which is the abbreviated as Kr2 or specifically abbreviated the Kr2(1-85 Active Zone) fragment; Kr2 active zone fragment fusion peptides herein abbreviated as the Kr2-frag-Fc fusion peptides; active zone fragments of Kr2 herein abbreviated as Kr2-frag peptides; and the modified active zone fragments of Kr2 herein abbreviated as mod-Kr2-frag peptides.

The Kr2-Fc fusion peptides of the third type of GRP78 antagonists include but not limited to those selected from the group consisting of SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

The Kr2-frag peptides of the third type of GRP78 antagonists include but not limited to those selected from the group consisting of SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, and SEQ ID NO:77.

The mod-Kr2-frag peptides of the third type of GRP78 antagonists include but not limited to those selected from the group consisting of SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, and SEQ ID NO:185.

There has thus been outlined, rather broadly, the more important features of the invention in order that the detailed description thereof that follows may be better understood, and in order that the present contribution of the art may be better appreciated.

BRIEF DESCRIPTION OF THE FIGURES

The file of this patent contains at least one drawing executed in color. Copies of this patent with color drawing(s) will be provided by the Office upon request and payment of the necessary fee.

The invention will be better understood and aspects other than those set forth above will become apparent when consideration is given to the following detailed description thereof that makes reference to the following drawings. It is also understood that the drawings are not necessarily to scale and in some instances proportions may have been exaggerated in order to more clearly depict certain features of the invention.

FIG. 18C is a graphic depiction of Kr1(3-91 Active Zone)frag-Fc SEQ ID NO:20 duplexed protein with kringle domains fused to human immunoglobulin (Ig) domains showing that the singular Kr1(3-91 Active Zone)frag-Fc c SEQ ID NO:20 protein couples with itself to form a duplex composite that contains two Kr1(3-91 Active Zone)frag-Fc SEQ ID NO:20 fragments per duplex composite.

DETAILED DESCRIPTION OF THE INVENTION

Figure 1:
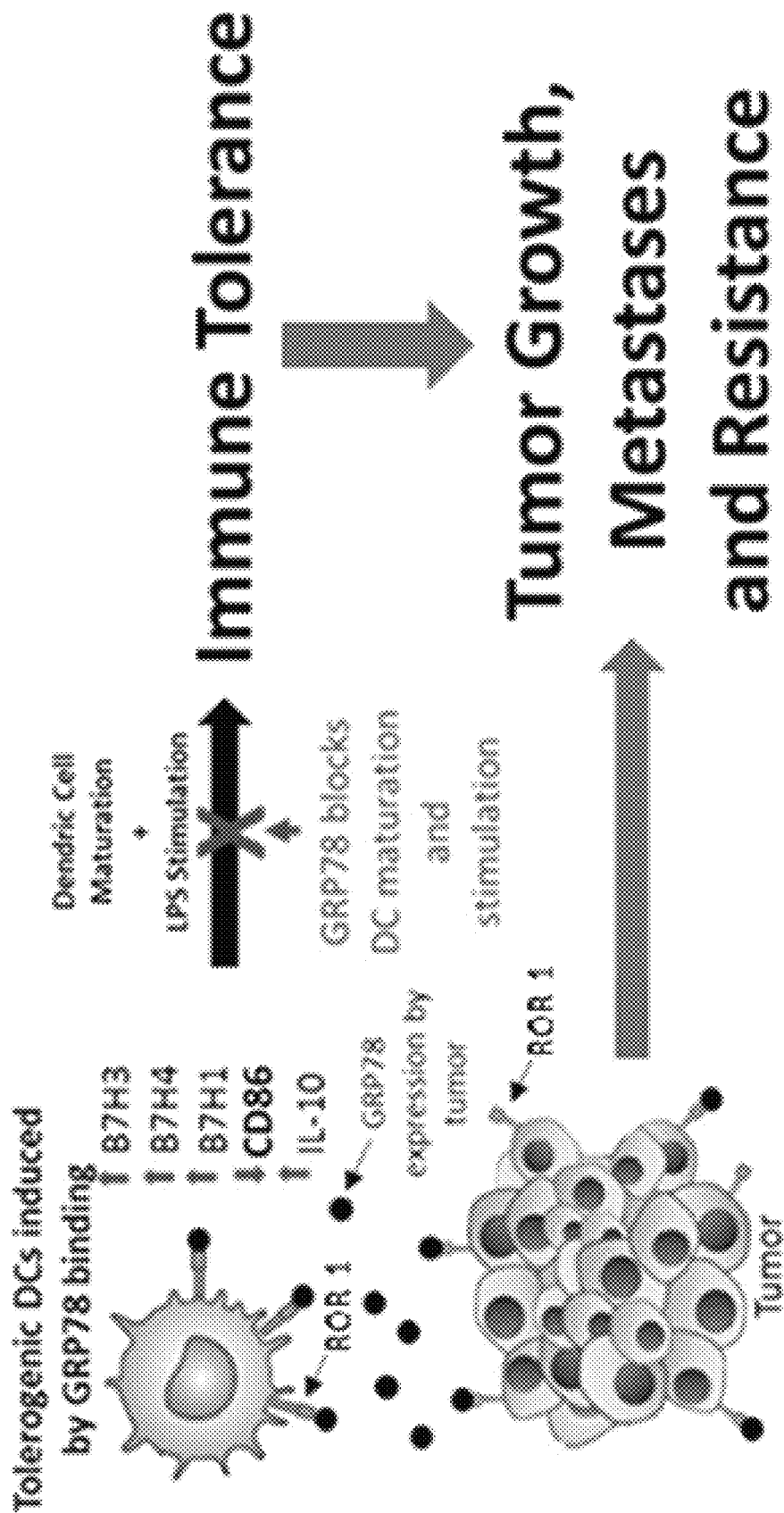
FIG. 1 depicts a stylized hypothetical mechanism of action for tolerogenic dendritic cells showing tumor expressed GRP78 binding to tumor and immune cells and which consequently leads to modified expression of B7H1, B7H3, B7H4, CD86 and IL-10.
Figure 2:
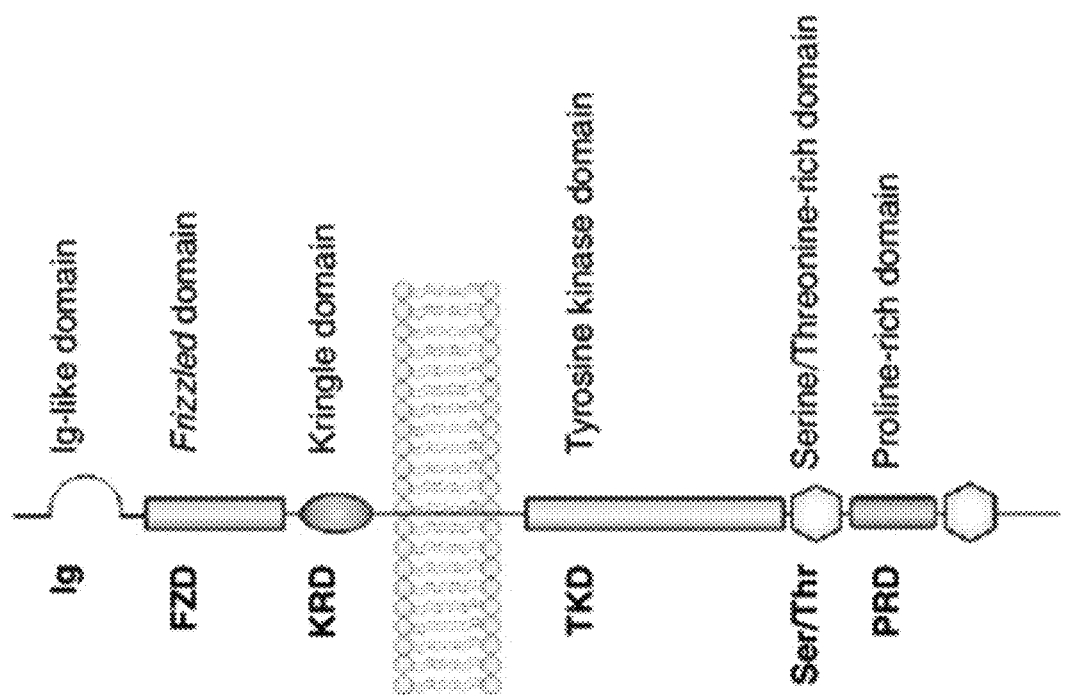
FIG. 2 depicts a stylized ROR1 bound to a cell membrane in which the ROR1 acts as surface receptor for GRP78 on glioma cells, activated endothelial cells and is highly expressed on dendritic cells.

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

Accordingly, the detailed discussion herein of one or more embodiments is not intended, nor is to be construed, to limit the metes and bounds of the patent protection afforded the present invention, in which the scope of patent protection is intended to be defined by the claims and their equivalents thereof. Therefore, embodiments not specifically addressed herein, such as adaptations, variations, modifications, and equivalent arrangements, should be and are considered to be implicitly disclosed by the illustrative embodiments and claims described herein and therefore fall within the scope of the present invention.

Further, it should be understood that, although steps of various the claimed method may be shown and described as being in a sequence or temporal order, the steps of any such method are not limited to being carried out in any particular sequence or order, absent an indication otherwise. That is, the claimed method steps are to be considered to be capable of being carried out in any sequential combination or permutation order while still falling within the scope of the present invention.

Additionally, it is important to note that each term used herein refers to that which a person skilled in the relevant art would understand such term to mean based on the contextual use of such term herein. To the extent that the meaning of a term used herein, as understood by the person skilled in the relevant art based on the contextual use of such term, differs in any way from any particular dictionary definition of such term, it is intended that the meaning of the term as understood by the person skilled in the relevant art should prevail.

As used herein, the term "kringle domain" refers to a conserved sequence that folds into large loops stabilized by 3 disulfide linkages, whose conformation is defined by a number of hydrogen bonds and small pieces of anti-parallel beta-sheet. Kringle domains are found in a varying number of copies in some plasma peptides including plasminogen, urokinase-type plasminogen activator, prothrombin, and human RORs.

As used herein, the term "kringle 5" (K5, hereinafter) refers to the region of mammalian plasminogen having three disulfide bonds which contribute to the specific three-dimensional confirmation defined by the fifth kringle region of the mammalian plasminogen molecule.

As used herein, the term "fusion conjugate" abbreviated as "Fc" refers to a polypeptide comprising an amino acid sequence drawn from two or more individual peptides. In the present invention fusion conjugates are understood to be fragments of kringle peptides chemically coupled to another protein to form a conjugate. Examples of fusion conjugates include a portion of the kringle 5 peptide fragment (SEQ ID NO: 1) coupled to a fragment of immunoglobulin. Molecular weights of fusion conjugates are between about 1,000 and about 25,000 kDa.

As used herein, the term "modified peptide" refers to a peptide fragment that has been modified by attaching a reactive group in which the modified peptide fragment is capable of forming a peptidase stabilized peptide through conjugation to blood components. The reactive group may be attached to the peptide by either via a linking group or optionally without using a linking group. One or more additional amino acids may be added to the peptide to facilitate the attachment of the reactive group. It is contemplated that modified peptides may be administered to a patient either by bolus or continuous introduction so that the modified peptides may then conjugate with blood components in vivo. Alternately it is contemplated that the modified peptides may be allowed to conjugate in vitro with any number of blood components such as immunoglobulin to form fusion compounds and then the resultant conjugated fusion compounds may then be administered in vivo.

As used herein, the term "peptidase stabilized peptide" refers to a modified peptide fragment that has been conjugated to a blood component, preferably via a covalent bond formation between the reactive group of the modified peptide fragment and a given functionality of the blood component. These peptidase stabilized peptides are believed to be more stable in the presence of peptidases in vivo than their non-stabilized peptide counterparts. Peptidase stabilized peptides exhibit at least a 10-50% increase in their respective half lifes as compared to their non-stabilized peptide counterparts.

As used herein, the term "linking groups" refers to a chemical moiety that links or connects a reactive group to a peptide fragment. Linking groups may be selected from the group consisting of alkyl, cycloalkyl, alkoxy, alkenyl, alkynyl, amino, groups, polycyclic, aryl, polyaryl, substituted aryl, heterocyclic, and substituted heterocyclic. Examples of some preferred linking groups include poly ethoxy aminoacids such as AEA ((2-amino) ethoxy acetic acid) and AEEA ([2-(2-amino)ethoxy)]ethoxy acetic acid) and maleimido groups such as gamma-maleimide butyrlamide (GMBA) or MPA. Further details on how to make and use any number of linking agents can be found in at least U.S. Pat. No. 7,144,854 which is incorporated in full herein.

Forming covalent bonds between the linking group and a functional group on a peptide fragment is preferably achieved by using a chemically reactive entity such as a carboxyl group, in particular esters, where the hydroxyl moiety is at a physiologically acceptable state that allows the linking or modification reaction to occur with a given peptide. While a number of different hydroxyl moieties may be employed in these linking agents, some of these preferred linking agents include those selected from the group consisting of N-hydroxysuccinimide (NHS), N-hydroxy-sulfosuccinimide (sulfo-NHS), maleimide-benzoyl-succinimide (MBS), gamma-maleimido-butyryloxy succinimide ester (GMBS) and maleimidopropionic acid (MPA).

Figure 3:
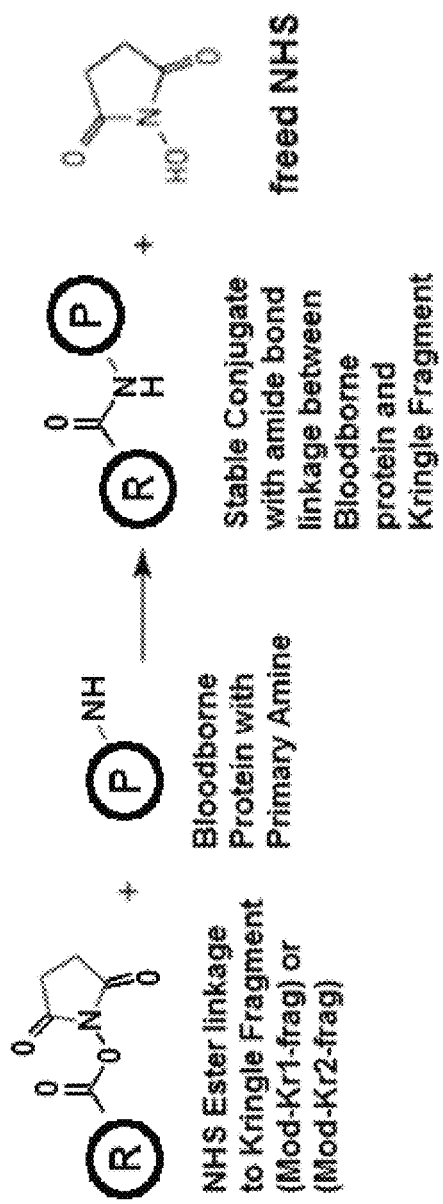
FIG. 3 reaction scheme of forming amide covalent bonds between kringle fragments and bloodborne proteins using N-hydroxysuccinimide esters as intermediates.

As used herein, the term "succinimidyl group" refers to a chemical moiety of a succinimide containing a reactive group also referred to as N-hydroxysuccinimide esters. The main reaction targets for using these N-hydroxysuccinimide esters are the primary amines peptides because they subsequently form amides with the peptide at physiological conditions (pHs between 7-9) as outlined in FIG. 3. The alpha-amine group at the N-terminus of the peptide reacts with the NHS esters to form a resultant amide bond (i.e., a stable conjugate) which also frees N-hydroxysuccinimide. Since these succinimidyl groups are generally quite stable in the presence of aqueous solutions then administration of these succinimidyl groups can be administered directly into the blood stream of the patient so that the coupling reaction can be achieved in vivo.

Figure 4:
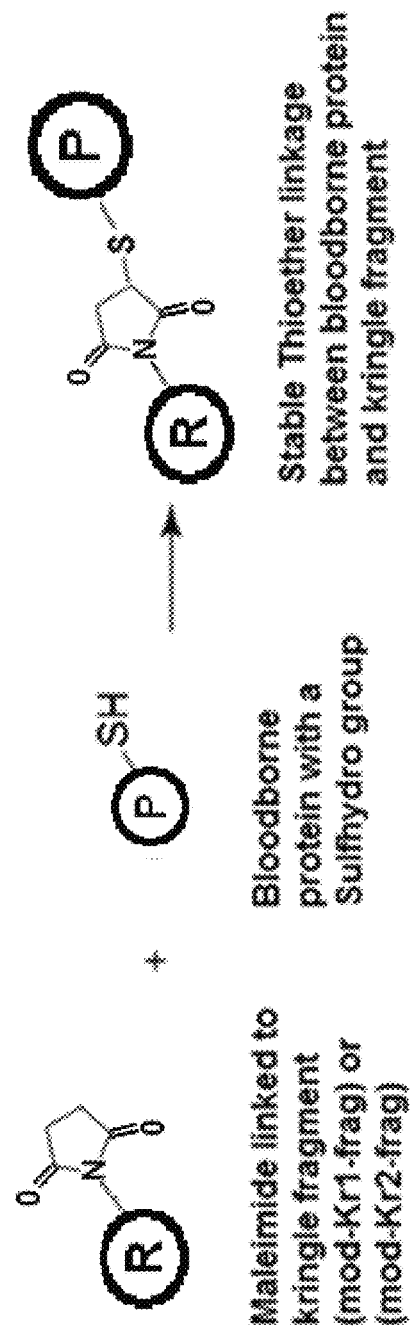
FIG. 4 reaction scheme of forming stable thioether linkages between kringle fragments and bloodborne proteins using maleimido groups as intermediates.

As used herein a "maleimido group" refers to a chemical moiety of a maleimido-containing reactive group such as gamma-maleimide butyrlamide (GMBA) or MPA. The main reaction targets for using these maleimido-containing reactive groups are sulfhydryl groups on peptides when the pH is between 6.5 and 7.4 in which the rate of reaction of maleimido groups with sulfhydryls can be up to 1000-fold faster than with amines. Under physiological conditions a resultant stable thioether linkage is formed between the maleimido group and the sulfhydryl of the peptide as illustrated in FIG. 4.

These maleimido groups are designed to react (in vivo or ex vivo protocols) with thiols groups on bloodborne proteins such as serum albumin or immunoglobulin forming stable thioether covalent linkages between the ROR1 or ROR2 kringle peptide fragments and that of the bloodborne proteins such as serum albumin or immunoglobulin. During in vivo administration these maleimido modified ROR1 and ROR2 kringle fragments (mod-Kr1-frag or mod-Kr2-frag) are intended to be directly introduced into the blood stream so that these maleimido groups can subsequently form stable thioether linkages to bloodborne proteins. These maleimido groups attached to the ROR1 and ROR2 kringle fragments are believed to be prone to unwanted degradation due to hydrolysis in the blood stream. Accordingly, these maleimido groups attached to the ROR1 and ROR2 kringle fragments are also intended to be directly introduced back into the blood stream by way of ex vivo treatment where the bloodborne proteins are first collected from the bloodstream and then reacted with the maleimido groups for form the stable thioether linkages between the bloodborne protein and the kringle fragment. Subsequent to ex vivo treatment, these bloodborne proteins thioether linked to the kringle fragments can then be readministered into the blood for in vivo treatment of the patient.

As used herein, the term "substantial sequence homology" means approximately 70% amino acid identity, more desirably approximately 80% amino acid identity and most desirably approximately 95% amino acid identity of the corresponding peptide sequence of human plasminogen. Sequences having substantial sequence homology to human plasminogen are referred to as "homologues". In addition to having substantial sequence homology, homologues of the present invention demonstrate like biological activity (i.e. anti-angiogenesis activity) as the kringle peptide fragments described herein. Because the amino acid sequence or the number of amino acids in a kringle peptide fragment may vary from species to species or from the method of production, the total number of amino acids in a kringle peptide fragment cannot, in some instances, be defined exactly. Given that these sequences are identical in at least 70% of their amino acids, it is to be understood that the amino acid sequence of a kringle peptide fragment is substantially similar among species and that methods of production of kringle peptide fragments provide kringle peptide fragments with substantial sequence homology to the corresponding amino acid sequences of found in human plasminogen, ROR1 and ROR2. It is well known in the art that modifications and changes can be made without substantially altering the biological function of that peptide. In making such changes, substitutions of like amino acid residues can be made on the basis of relative similarity of side-chain substituents, for example, their size, charge, hydrophobicity, hydrophilicity and the like. Alterations of the type described may be made to enhance the peptide's potency or stability to enzymatic breakdown or pharmacokinetics. Thus, sequences deemed as within the scope of the invention, include those analogous sequences characterized by a change in amino acid residue sequence or type wherein the change does not alter the fundamental nature and biological activity of the aforementioned kringle peptide fragments, kringle peptide modified fragments and/or fusion peptides.

As used herein, the term "receptor tyrosine kinase orphan receptor (ROR)" refers to a family of tyrosine kinase receptors including ROR1 and ROR2. An "ROR polypeptide" includes an amino acid sequence that has at least about 70% identity to the corresponding ROR1 or ROR2 over a comparison window of at least 15 contiguous amino acids. ROR polypeptides include full-length, wild-type ROR peptides, as well as ROR fragments (peptides), variants, and polypeptide derivatives. In alternative embodiments, this term encompasses polypeptides sharing at least about 80% identity to ROR1 or ROR2.

As used herein, the term "Wnt polynucleotide" refers to a family of conserved, cysteine-rich, secreted glycopeptides that have been found to be involved in critical aspects of early embryonic development. A "Wnt polypeptide" comprises an amino acid sequence that has at least about 70% identity, over a comparison window of at least 15 contiguous amino acids, to any polypeptide identified in Genbank as a Wnt. Wnt polypeptides include full-length, wildtype Wnt peptides, as well as Wnt fragments (peptides), variants, and polypeptide derivatives. In alternative embodiments, this term encompasses polypeptides sharing at least about 80% identity to a Wnt.

As used herein, the term "GRP78 polypeptides" include full-length, wild-type GRP78 peptides, as well as GRP78 fragments (peptides), variants, and polypeptide derivatives. In alternative embodiments, this term encompasses polypeptides sharing at least about 80% identity to a GRP78.

As used herein, an "antibody" refers to a protein consisting of one or more polypeptides substantially encoded by immunoglobulin genes or fragments of immunoglobulin genes. An antibody is said to be "specific for" a target molecule if the antibody specifically binds the target molecule. The site on the target molecule to which the antibody binds is termed an "epitope."

As used herein "immunoglobulin" protein can include the gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

A used herein, the term "small molecule" refers to a molecule having a molecular weight of less than about 5 kilodaltons.

A "modulator" of a polypeptide (e.g., GRP78, ROR1, or ROR2) is either an inhibitor or an enhancer of GRP78 or ROR1 or ROR2 action.

A "non-selective" modulator of a particular polypeptide (e.g., ROR1 or ROR2) is an agent that modulates other polypeptides (e.g., EGFR) at the concentrations typically employed for modulation of the particular polypeptide.

A "selective" modulator of a particular polypeptide significantly modulates the particular polypeptide at a concentration at which other polypeptides are not significantly modulated. Thus, a modulator can be selective for, e.g., GRP78, or ROR1 or ROR2 (as opposed to other tyrosine kinases) or can be selective for a subtype, such as, for example, GRP78 or ROR1 or ROR2.

A modulator "acts directly on" a polypeptide when the modulator binds to the polypeptide, respectively.

A modulator "acts indirectly on" a polypeptide when the modulator binds to a molecule other than the polypeptide, which binding results in modulation of polypeptide function.

An "inhibitor" or "antagonist" of a polypeptide is an agent that reduces, by any mechanism, any polypeptide action, as compared to that observed in the absence (or presence of a smaller amount) of the agent. For example, an inhibitor of a receptor can affect: (1) the expression, mRNA stability, protein trafficking, modification (e.g., phosphorylation), dimerization or degradation of a receptor or of a ligand for the receptor, or (2) one or more of the normal functions of the receptor. An inhibitor of a receptor can be non-selective or selective. Preferred inhibitors (antagonists) are generally peptides and molecules that act directly on, and are selective for, the target receptor.

One aspect of polypeptide function that can be inhibited is the specific binding of a polypeptide to another molecule, termed a "binding partner." The term "specific binding" is defined herein as the preferential binding of binding partners to another (e.g., two polypeptides, a polypeptide and polynucleotide, or two polynucleotides) at specific sites. The term "specifically binds" indicates that the binding preference (e.g., affinity) for the target molecule/sequence is at least 5-fold, and more preferably at least 20-fold over a non-specific target molecule (e.g. a randomly generated molecule lacking the specifically recognized site(s)).

An inhibitor can inhibit the binding of a polypeptide to a binding partner. As used herein, a "competitive inhibitor" of a particular polypeptide refers to any agent that inhibits the binding of the polypeptide by binding to the binding partner at the binding site or elsewhere. In competitive inhibition, the inhibitor binds the binding partner at or near the same binding site as the polypeptide, thus preventing the polypeptide from binding. In allosteric competitive inhibition, the inhibitor binds away from the binding site for the polypeptide, creating a conformational change in the binding partner such that the polypeptide can no longer bind to it.

As used herein, the term "biological sample" refers a sample derived from an organism and includes any organ, tissue, cell, or biological fluid. A biological sample may be derived, for example, from cells or tissue cultures in vitro or from a population os single-cell organisms.

As used herein, the phrases "an effective amount" and "an amount sufficient to" refer to amounts of a biologically active agent to produce an intended biological activity.

As used herein, the term "therapy" refers to any regimen aimed at the treatment or of any pathology and/or associated symptoms.

As used herein, the term "anti-angiogenic" refers to any effect that tends to inhibit the formation of new blood vessels and/or the growth of existing ones. "Antiangiogenesis therapy" is any regimen aimed at producing an anti-angiogenic effect. Examples of diseases that are amenable to anti-angiogenesis therapy include cancer, diabetic retinopathy, and rheumatoid arthritis.

As used herein, the term "apoptotic" refers to any effect that tends to result in cell death.

As used herein, the phrase "cancer therapy" refers to any regimen for the prophylaxis or treatment of cancer.

As used herein, the phrase "synthetic peptide" as used herein means a polymeric form of amino acids of any length, which may be chemically synthesized by methods well-known to an ordinarily skill practitioner. These synthetic peptides are useful in various applications.

As used herein, the term "polypeptide" as used herein indicates a molecular chain of amino acids and does not refer to a specific length of the product. Thus, peptides, oligopeptides and peptides are included within the definition of polypeptide. This term is also intended to refer to post-expression modifications of the polypeptide, for example, glycosylations, acetylations, phosphorylations and the like.

The term "antigen" as used herein indicates a compound, composition, or substance that can stimulate the production of antibodies or a T-cell response, including compositions that are injected or absorbed. An antigen (Ag) reacts with the products of specific humoral or cellular immunity. In some embodiments, an antigen also may be the specific binding target of the engineered CH2 scaffolds or binding moieties whether or not such interaction could produce an immunological response.

As used herein, terms "neoplasia" and "tumor" or "cancer" as used herein indicates an abnormal growth of tissue that results from excessive cell division. A tumor that does not metastasize is referred to as "benign." A tumor that invades the surrounding tissue and/or can metastasize is referred to as "malignant." Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

As used herein, term "pharmaceutically acceptable vehicles" as used herein indicates pharmaceutically acceptable carriers (vehicles) useful in this disclosure may be conventional but are not limited to conventional vehicles for pharmaceutical delivery of one or more therapeutic compounds, such as one or more kringle fusion conjugate, and additional pharmaceutical agents.

As used herein, the term "preventing" a disease as used herein to indicate inhibiting a disease in the full development of a disease.

The term "treating" a disease or pathological condition refers to a therapeutic intervention that ameliorates a sign or symptom of a disease or pathological condition after it has begun to develop.

The term "managing" a disease refers to a therapeutic intervention that does not allow the signs or symptoms of a disease to worsen.

The term "ameliorating" a disease refers to the reduction in the number or severity of signs or symptoms of a disease.

The term "purified" is understood to not necessarily requiring absolute purity; rather, it is intended as a relative term. Thus, for example, a purified kringle fusion conjugate peptide may be one that is isolated in whole or in part from naturally associated peptides and other contaminants in which the molecule is purified to a measurable degree relative to its naturally occurring state, for example, relative to its purity within a cell extract or biological fluid.

The term "therapeutically effective amount" refers to a quantity of a specified agent sufficient to achieve a desired effect in a subject being treated with that agent. The therapeutically effective amount of an agent useful for preventing, ameliorating, and/or treating a subject will be dependent on the subject being treated, the type and severity of the affliction, and the manner of administration of the therapeutic composition.

The term "half-life" typically refers to the time required for the plasma concentration of a drug to be reduced by one-half. The terms "half-life", "$t_{1/2}$", "elimination half-life" and "circulating half-life" are used interchangeably herein.

The term "antagonist", as used herein, includes any molecule that partially or fully blocks, inhibits, or neutralizes a biological activity of a native polypeptide disclosed herein. Methods for identifying antagonists of a polypeptide may comprise contacting a native polypeptide with a candidate antagonist molecule and measuring a detectable change in one or more biological activities normally associated with the native polypeptide.

The term "agonist" as used herein, includes any molecule that mimics a biological activity of a native polypeptide disclosed herein. Suitable agonist molecules specifically include agonist antibodies or antibody fragments, fragments or amino acid sequence variants of native polypeptides, peptides, small organic molecules, etc. Methods for identifying agonists of a native polypeptide may comprise contacting a native polypeptide with a candidate agonist molecule and measuring a detectable change in one or more biological activities normally associated with the native polypeptide.

The term "activity" for the purposes herein refers to an action or effect of a component of a fusion protein consistent with that of the corresponding native active protein, wherein "biological activity" or "bioactivity" as those terms are used interchangeably herein refers to an in vitro or in vivo biological function or effect, including but not limited to receptor binding, antagonist activity, agonist activity, or a cellular or physiologic response.

The term "therapeutic effect", as used herein, refers to a physiologic effect, including but not limited to the cure, mitigation, amelioration, or prevention of disease in humans or other animals, or to otherwise enhance physical or mental well-being of humans or animals.

As used herein, naturally-occurring amino acids and aminoacyl residue names used herein adhere to the IUPAC naming conventions. Accordingly, the terms "Ala," "Arg," "Asn," "Asp," "Cys," "Gln," "Glu," "Gly," "His," "Ile," "Leu," "Lys," "Met," "Phe," "Pro," "Ser," "Thr," "Trp," "Tyr" and "Val" refer to the amino acids alanine, arginine, asparagine, aspartic acid, cysteine, glutamine, glutaaaic acid, glycine, histidine, isoleucine, leucine, lysine, methionine, phenylalanine, proline, serine, threonine, tryptophan, tyrosine and valine and their corresponding amninoacyl residues in peptides in their L-, D- or D, L-forms.

Where no specific configuration is indicated, one skilled in the art would understand that the stereochemistry of the α-carbon of the amino acids and aminoacyl residues in peptides described in this specification and the appended claims is the naturally occurring or "L" configuration with the exception of the achiral molecule glycine and with the further exception of any amino acids which are achiral or otherwise designated as "D-."

The terms "amino acid sequence", "polypeptide", "peptide", and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation; or any other manipulation, such as conjugation with a labeling component. As used herein the term "amino acid" refers to either natural and/or unnatural or synthetic amino acids, including but not limited to glycine and both the D or L optical isomers, and amino acid analogs and peptide mimetics. Standard single or three letter codes are used to designate amino acids.

All peptide sequences are written according to the generally accepted convention whereby the α-N-terminal amino acid residue is on the left and the α-C-terminal is on the right. As used herein, the term "α-N-terminal" refers to the free alpha-amino group of an amino acid in a peptide, and the term "α-C-terminal" refers to the free alpha-carboxylic acid terminus of an amino acid in a peptide.

The term "peptide fragment" as used herein means a polymeric form of amino acids of any length, which may be chemically synthesized by methods well-known to an ordinarily skill practioner. These peptide fragments are useful in various applications.

"Polypeptide" as used herein indicates a molecular chain of amino acids and does not refer to a specific length of the product. Thus, peptides, oligopeptides and peptide fragments are included within the definition of polypeptide. This term is also intended to refer to post-expression modifications of the polypeptide, for example, glycosylations, acetylations, phosphorylations and the like.

All peptide sequences are written according to the generally accepted convention in which the α-N-terminal amino acid residue is on the left and the α-C-terminal is on the right. As used herein, the term "α-N-terminal" refers to the free alpha-amino group of an amino acid in a peptide, and the term α-C-terminal" refers to the free alpha-carboxylic acid terminus of an amino acid in a peptide.

As used herein, the term "prodrug" refers to compounds which are transformed in vivo to yield the parent compound, for example, any one of the modified kringle fragments of the present invention that subsequent couple onto blood-borne peptides subsequent to introduction of the modified kringle fragment into the blood stream.

As used herein, the term "pharmaceutically acceptable prodrug" refers to (1) those prodrugs of the compounds of the present invention which are, within the scope of sound medical judgment, suitable for use in contact with the tissues of humans and lower animals without undue toxicity, irritation, allergic response and the like, commensurate with a suitable benefit-to-risk ratio and effective for their intended use and (2) zwitterionic forms, where possible, of the parent compound.

As used herein, the term "antiangiogenesis activity" refers to the capability of a molecule to inhibit the growth of blood vessels.

As used herein, the term "endothelial inhibiting activity" refers to the capability of a molecule to inhibit angiogenesis in general and, for example, to inhibit the growth or migration of bovine capillary endothelial cells in culture in the presence of fibroblast growth factor or other known growth factors.

As used herein, the term "$ED_{50}$" is an abbreviation for the dose of a kringle peptide fragment or fusion protein which is effective to inhibit the growth of blood vessels or inhibit the growth of bovine capillary endothelial cells in culture in the presence of fibroblast growth factor or other known growth factors or inhibit the migration of endothelial cells by one-half of what the growth or migration would be in the absence of the inhibitor.

Figure 5:
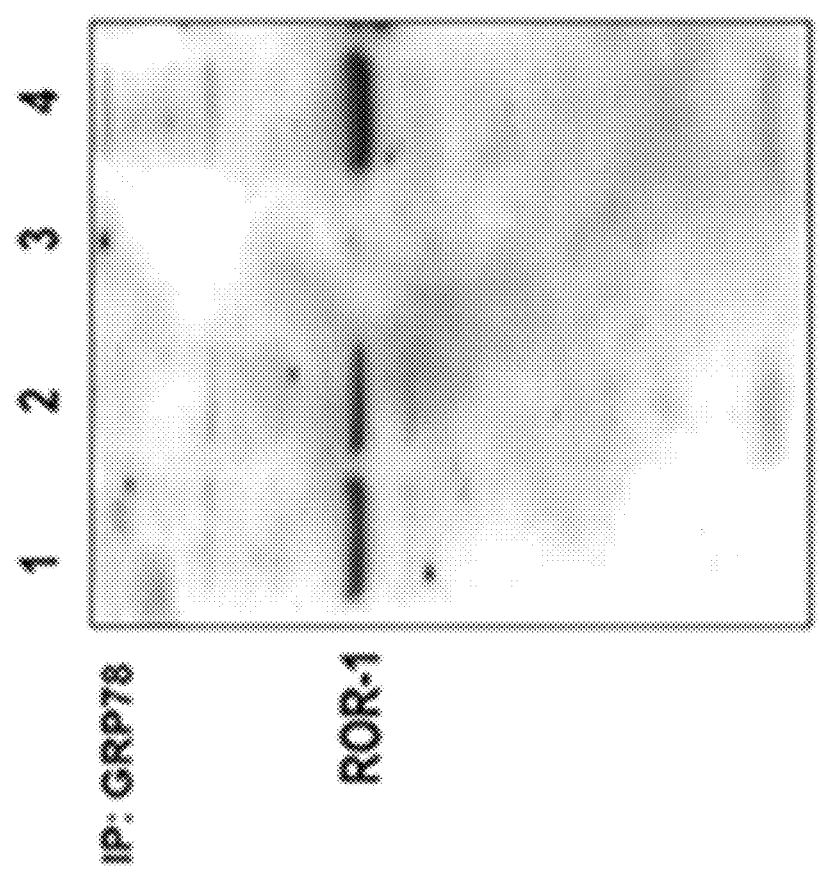
FIG. 5 is a Western blot from an electrophoresis gel showing immunoprecipitation (IP) of D54 glioma cell-surface protein lysates with the GRP78 protein IP with GRP78 wherein tract 1 designates none, tract 2 designates C-term GRP78 antibody, tract 3 designates C-term GRP78 antibody plus 100 nM of folded K5(3-89 Active Zone)frag SEQ ID NO: 1, and tract 4 designates C-term GRP78 antibody plus 100 nM of unfolded K5(3-89 Active Zone) frag SEQ ID NO:1.

The use of GRP78/ROR1 antagonists to break immune tolerance for the treatment of resistant cancers represents a major shift in cancer therapies. Few, if any, current anti-cancer therapies have anti-angiogenic, anti-tumor and immune modulatory activities similar to modified ROR1, ROR2, and K5 kringle domains. To understand what pathways could be responsible for these activities in tumor and dendritic cells, we used GRP78 binding and crosslinking pull down studies against the cell surface proteome of D54 glioma cells and dendritic cells. We have identified that ROR1 and ROR2 as a cell GRP78 surface receptor. FIG. 5 shows the immunoprecipitation of D54 glioma cells with GRP78 protein as analyzed in Western blot of D54 glioma cells surface protein lysate IP with GRP78 and competition in which tract 1 is none; tract 2 is C-terminus GRP78 antibody; tract 3 is C-terminus GRP78 antibody with 100 nM K5(3-89 Active Zone)frag SEQ ID NO:1; and tract 4 is C-terminus GRP78 antibody and 100 nM of unfolded K5(3-89 Active Zone)frag SEQ ID NO:1 kringle.

Figure 6:
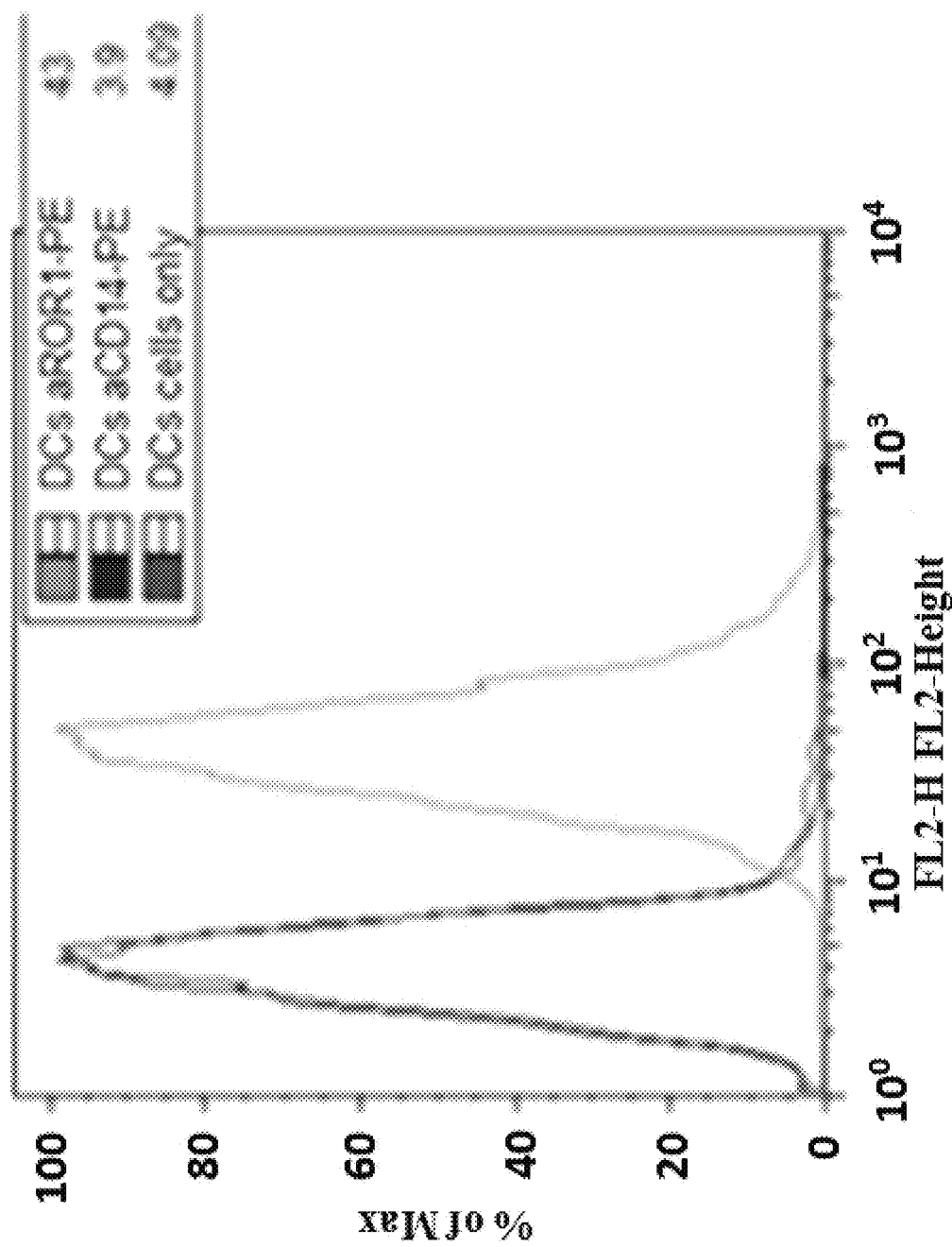
FIG. 6 is a flow cytometry analysis profile of immature DCs stained for ROR1 expression in which the immature DCs anti-ROR1-PE treated cells (i.e., DCs aROR1-PE depicted in the green distribution) was found to be distributed differently than both the immature untreated DCs cells (red distribution) and that of the immature DCs treated with anti-CD14-PE (blue distribution) which distributed nearly in an identical pattern.

To determine if ROR1 is expressed on immature dendritic cells, CD14$^+$ cells were isolated from human PBMCs and cultured in GM-CSF, and IL-4 for 7 days to produce immature DCs. The immature DCs were stained for ROR1 expression and analyzed by flow cytometry analysis, as shown in FIG. 6. The flow cytometry analysis of the immature DCs anti-ROR1-PE treated cells (i.e., DCs anti-ROR1-PE depicted in the green distribution pattern) was found to be distributed differently than both the immature untreated DCs cells (i.e., DC cells only depicted in the red distribution pattern) and that of the immature DCs treated with anti-CD14 (DCs anti-CD14-PE depicted in the blue pattern) which distributed nearly in an identical pattern. This flow cytometry analysis supports the hypothesis that immature dendritic cells express ROR1 in which the ROR1 kringle domain binds to GRP78. Comparison of GRP78 binding for the two kringle domains was also performed by ELISA in which it was found that ROR1 kringle Kr1(1-91 Active Zone)frag SEQ ID NO:19 (Kd=0.03 nM) binds to GRP78 20× tighter than the plasminogen kringle K5(3-89 Active Zone)frag SEQ ID NO:1 (Kd=0.6 nM).

Figure 7:
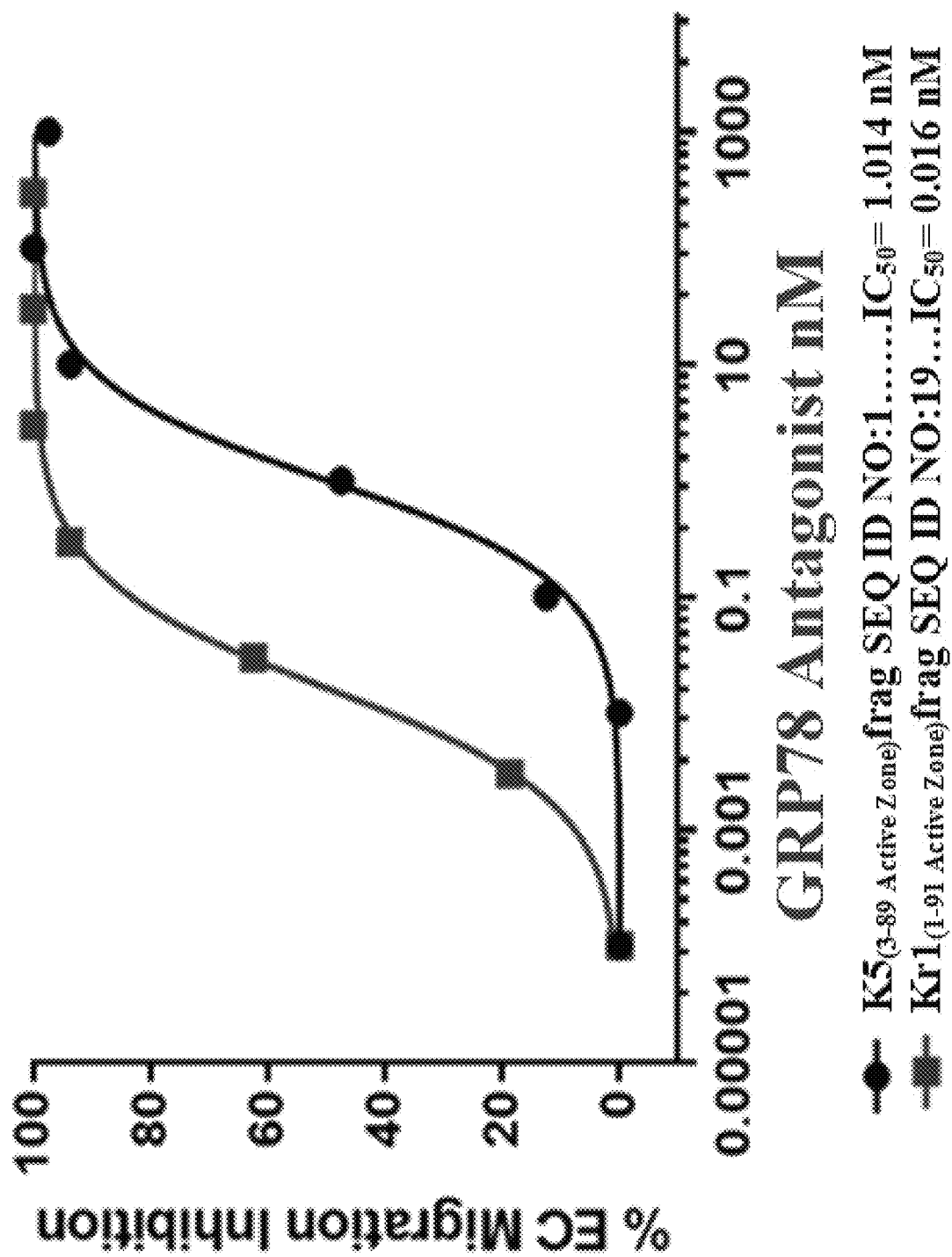
FIG. 7 is an endothelial cell migration assay (average of 3 runs) showing that (red -■-) SEQ ID NO:19 abbreviated as Kr1(1-91 Active Zone)frag SEQ ID NO:19 which was found to be more potent (50×) for inhibition than (black -●-) K5(3-89 Active Zone)frag SEQ ID NO: 1.

For functional assays, we have used several assays, one of which was the endothelial cell migration assay of FIG. 7. As expected, the Kr1(1-91 Active Zone)frag SEQ ID NO: 19 was found to be more potent (50×) for inhibition of endothelial cell (EC) migration than K5(3-89 Active Zone)frag SEQ ID NO: 1. Using siRNA knock down experiments, commercial ROR1 antibodies, and a recombinant ROR1 kringle domain (Kr1) with glioma cells, we can show that GRP78 binds to ROR1 on the cell surface and is necessary for increase cell proliferation. It is known that Wnt5 binding to ROR1 involves the non-canonical signaling pathway resulting in downstream increased phosphorylation of Pl-3K leading to tumor cell proliferation, and migration. We can show that this GRP78 binding to ROR1 and the resulting Pl-3K phosphorylation can be blocked by our GRP78 antagonists on the cell surface of tumor, endothelial cell (EC) and dendritic cells through the kringle domain of ROR1. This results in reduced proliferation, resistance and tolerance. Presented herewith are novel forms of long-lasting modified kringle domains. These novel forms have two kringle domains on an Fc portion of a human antibody backbone. Their molecular weights are around 70 kDa and data shows that the K5(3-89 Active Zone)frag-Fc SEQ ID NO:2 version in mice has a 300× longer half-life than that of K5(3-89 Active Zone)frag SEQ ID NO:1.

Figure 19A:
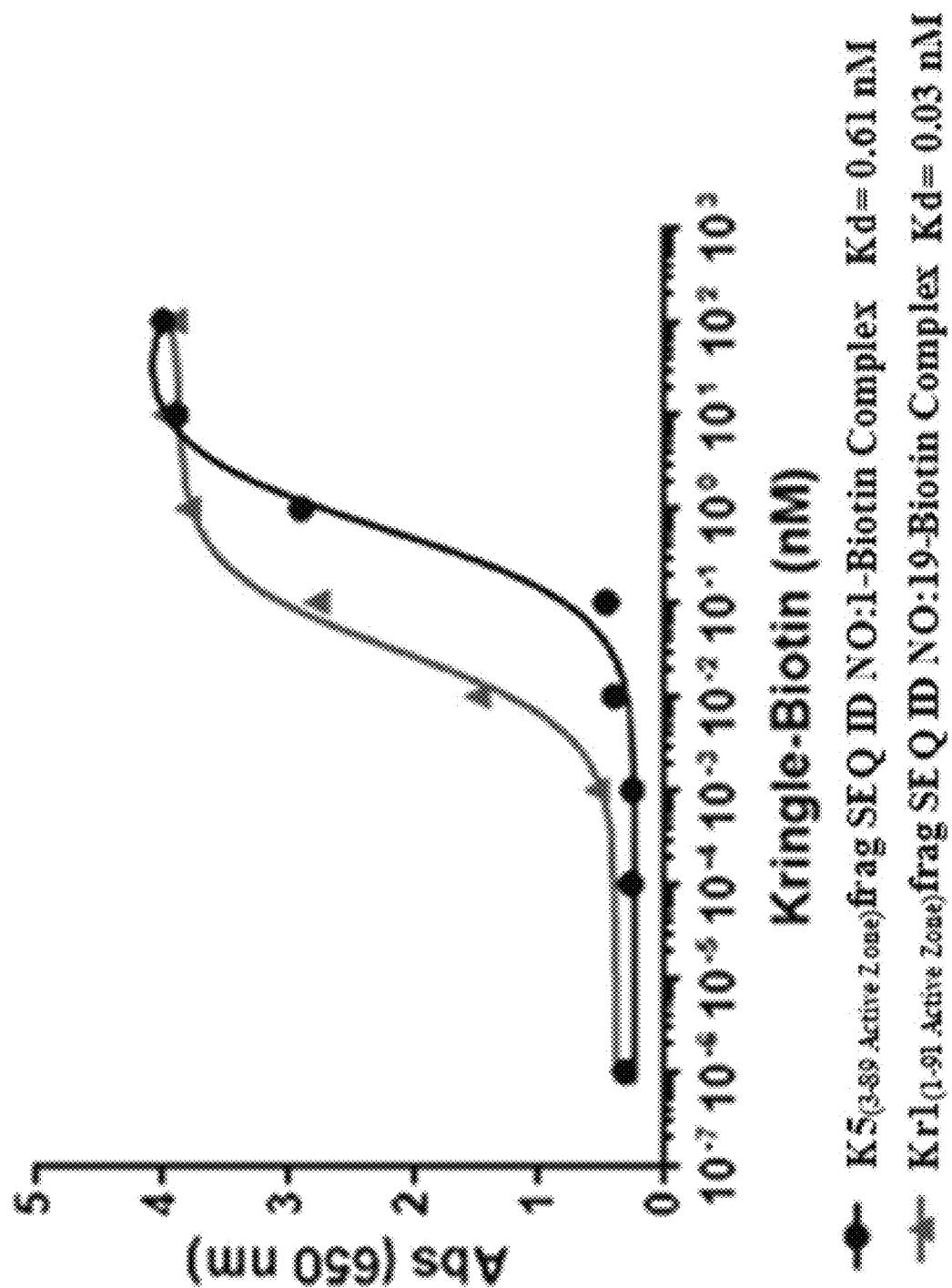
FIG. 19A show results of GRP78 antagonists binding to GRP78 in which GRP78 was coated on a 96 well plate and bound with either (black -●-) K5(3-89 Active Zone)frag SEQ ID NO:1-Biotin or (red -▲-) Kr1(1-91 Active Zone) frag SEQ ID NO:19-Biotin complex. Recombinant K5-fragment biotin and Kr1 fragment-biotin were used for binding. Neutra-avidin-HRP was used to detect binding after washing with PBS. Small peptide GRP78 antagonists, K5(3-89 Active Zone)frag SEQ ID NO:1 and Kr1(1-91 Active Zone) frag SEQ ID NO:19, bind in the pM range to GRP78.

It is known that K5(3-89 Active Zone)frag SEQ ID NO:1 exhibits a novel multi-stage mechanism of action in vivo: (1) the antiangiogenic activity of K5(3-89 Active Zone)frag SEQ ID NO:1 induces apoptosis in activated tumor ECs and then (2) the consequent hypoxia causes tumor cells to present secreted GRP78. GRP78 then complexed with K5(3-89 Active Zone)frag SEQ ID NO:1 induces tumor cell apoptosis through an incompletely defined mechanism. In vivo studies have already demonstrated that K5(3-89 Active Zone)frag SEQ ID NO:1 exhibits potent antitumor effects in multiple preclinical tumor models such as the in 6-month monkey studies dosed with K5(3-89 Active Zone)frag SEQ ID NO:1 showed a 20× projected efficacious dose, and which resulted in no adverse physiologically effects. The problem was and is that K5(3-89 Active Zone)frag SEQ ID NO:1 alone displays a relatively short 12-minute pharmacokinetic half-life in monkeys. We have developed a novel modified ROR1 kringle domain Kr1(1-91 Active Zone)frag SEQ ID NO:19 that displays a 20-fold tighter binding affinity for GRP78 as that of K5(3-89 Active Zone)frag SEQ ID NO:1 alone (FIG. 19A). This increase in binding affinity translates into a 50-fold increase in potency against endothelial cell (EC) migration and competition binding to GRP78 over K5(3-89 Active Zone)frag SEQ ID NO:1 (FIGS. 7, 19B) in which bFGF was used to stimulate endothelial cell (EC) migration. Kringles were added to the bottom chambers and fluorescently labeled ECs were added to the top chamber and let migrated for 24 hrs in which fluorescence of the bottom well was measured. In addition to migration inhibition, these novel GRP78 antagonists can break the immune tolerance of immature dendritic cells by blocking GRP78 binding resulting in reduced B7H1(PD-L1), B7H3, B7H4, and IL-10 expression in vitro.

ROR1 is a surface receptor for GRP78 on glioma cells, activated endothelial cells and is highly expressed on dendritic cells (FIG. 1). We have discovered that soluble GRP78 binds to ROR1 on dendritic, glioma, and endothelial cells by using GRP78 pull down experiments, in which we identified ROR1 as a GRP78 surface receptor on D54 glioma and endothelial cells. The immunoprecipitation of ROR1 using GRP78 was found to be completely blocked with K5(3-89 Active Zone)frag SEQ ID NO:1 but not by C-terminal GRP78 antibodies or unfolded K5(3-89 Active Zone)frag SEQ ID NO: 1. What is interesting about this finding is that like K5(3-89 Active Zone)frag SEQ ID NO:1, ROR1 and ROR2 contains a similar kringle domain.

Soluble GRP78 binds to myeloid derived dendritic cells resulting in the upregulated expression of IL-10, PD-L1, B7H4, B7H3 and the downregulated expression of maturity marker CD86 leading to a tolerogenic phenotype that is stable with LPS stimulation. Consequently surface GRP78 binding on tumor cells leads to chemo-resistance and proliferation. Both Kr1(1-91 Active Zone)frag SEQ ID NO:19 and K5(3-89 Active Zone)frag SEQ ID NO: 1 can block the tolerogenic phenotype of DCs induced by GRP78. Immature dendritic cells were differentiated from isolated CD14+ myeloid cells with the addition of GM-CSF and IL-4 for 7 days. GRP78 (10 µg/ml) was added to the cells to produce a tolerogenic phenotype showing up regulation of PD-L1, B7H4, B7H3, IL-10 and down regulation of CD86. Therefore our GRP78 antagonists can potently block the activity of GRP78 on dendritic cells. In a dose dependent inhibition, both K5(3-89 Active Zone)frag SEQ ID NO:1 and Kr1(1-91 Active Zone)frag SEQ ID NO:19 showed potent activity with Kr1(3-91 Active Zone)frag-Fc SEQ ID NO:20 showing pM inhibition of GRP78's up regulation of PD-L1, B7H4, B7H3, IL-10 and increased expression of the maturity marker CD86 on dendritic cells.

Figure 8:
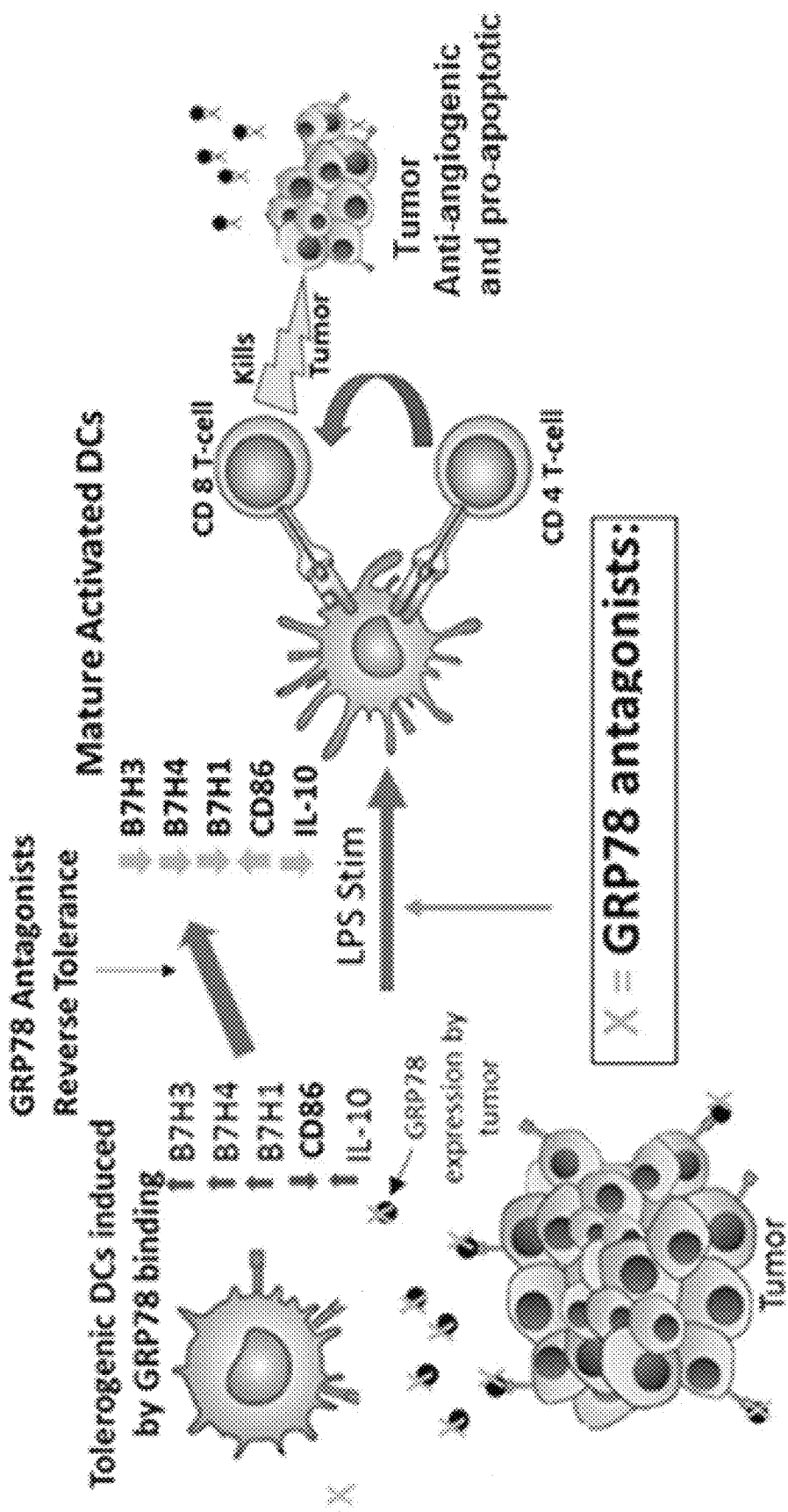
FIG. 8 depicts a stylized mechanism of GRP78 antagonist (green x's) on reversing DCs tolerogenic phenotype leading to T-cell activation and tumor killing.

FIG. 8 depicts our proposed stylized mechanism of action of GRP78 antagonist in which binding of GRP78 to ROR1 on DCs is substantially reduced or curtailed. As a consequence the GRP78 antagonist reverses the tolerogentic DCs which then allows the unencumbered DC to interact with T-cells via the LPS stimulation which in turns results in pro apoptotic action of the tumor.

These peptide GRP78 antagonists, K5(3-89 Active Zone) frag SEQ ID NO:1, Kr1(1-91 Active Zone)frag SEQ ID NO:19, K5(3-89 Active Zone)frag-Fc SEQ ID NO:2, and Kr1(3-91 Active Zone)frag-Fc SEQ ID NO:20 can reverse this tolerogenic and resistant phenotype. Our data demonstrates that GRP78 binds to the kringle domain of ROR1 leading to ROR1 signaling through several different non-canonical pathways. This ROR1 signaling in dendritic cells induces a tolerogenic phenotype and a resistant phenotype in tumor cells.

Furthermore it is known that Wnt5a is a second ligand that binds to the frizzled domain of ROR1, which leads to increased migration and proliferation of leukemia cells. Our data shows that by blocking the GRP78 binding to ROR1, Wnt5a binding does not lead to activation of ROR1.

Our data shows reversal of tolerogenic phenotype of dendritic cells and reverses resistance to induce glioma cell apoptosis with our GRP78 antagonists. We believe that GRP78 binds to ROR1 and initiates the subsequent binding of other ROR1 ligands and associated peptides as shown in the stylized mechanism in FIG. 8. We believe the binding to GRP78 to the kringle domain or ROR1 leads to an LRP protein binding and Wnt5a binding which initiates homo or heterodimerization ROR1 with several different tyrosine kinases. Finally, the complex binding and dimerization results in signaling through b-Catenin, PI-3K, MyD88, or NF-kB depending on its dimerization partner.

Figure 9A:
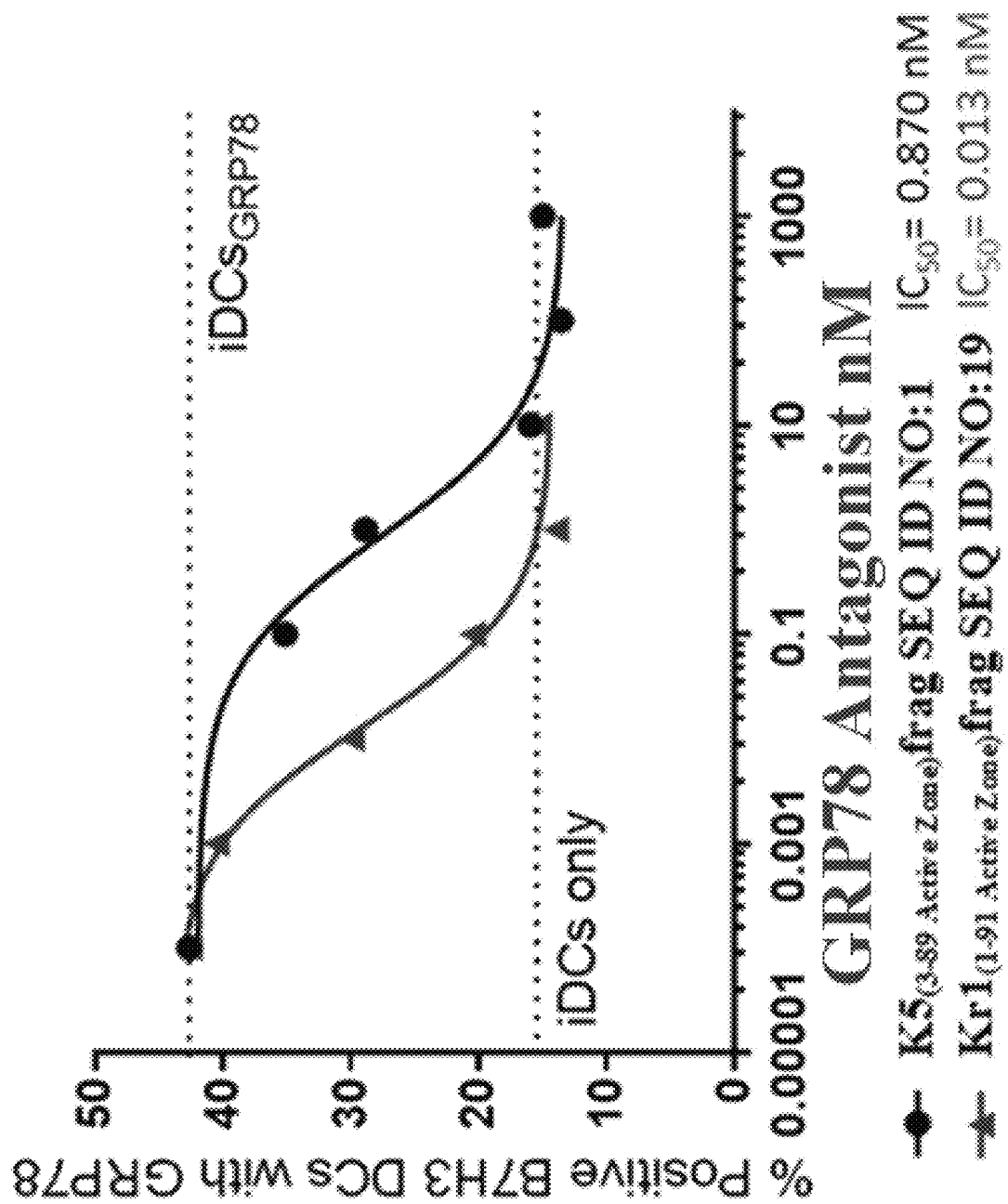
FIG. 9A depicts decreasing concentrations of B7H3 on DCs, by flow cytometry analysis, as a function of increasing amounts of the GRP78 antagonists i.e., (black -●-) K5(3-89 Active Zone)frag SEQ ID NO:1 and (red -■-) Kr1(1-91 Active Zone)frag SEQ ID NO:19, showing that (red -■-) Kr1(1-91 Active Zone)frag SEQ ID NO: 19 is more potent than (black -●-) K5(3-89 Active Zone)frag SEQ ID NO:1.
Figure 9B:
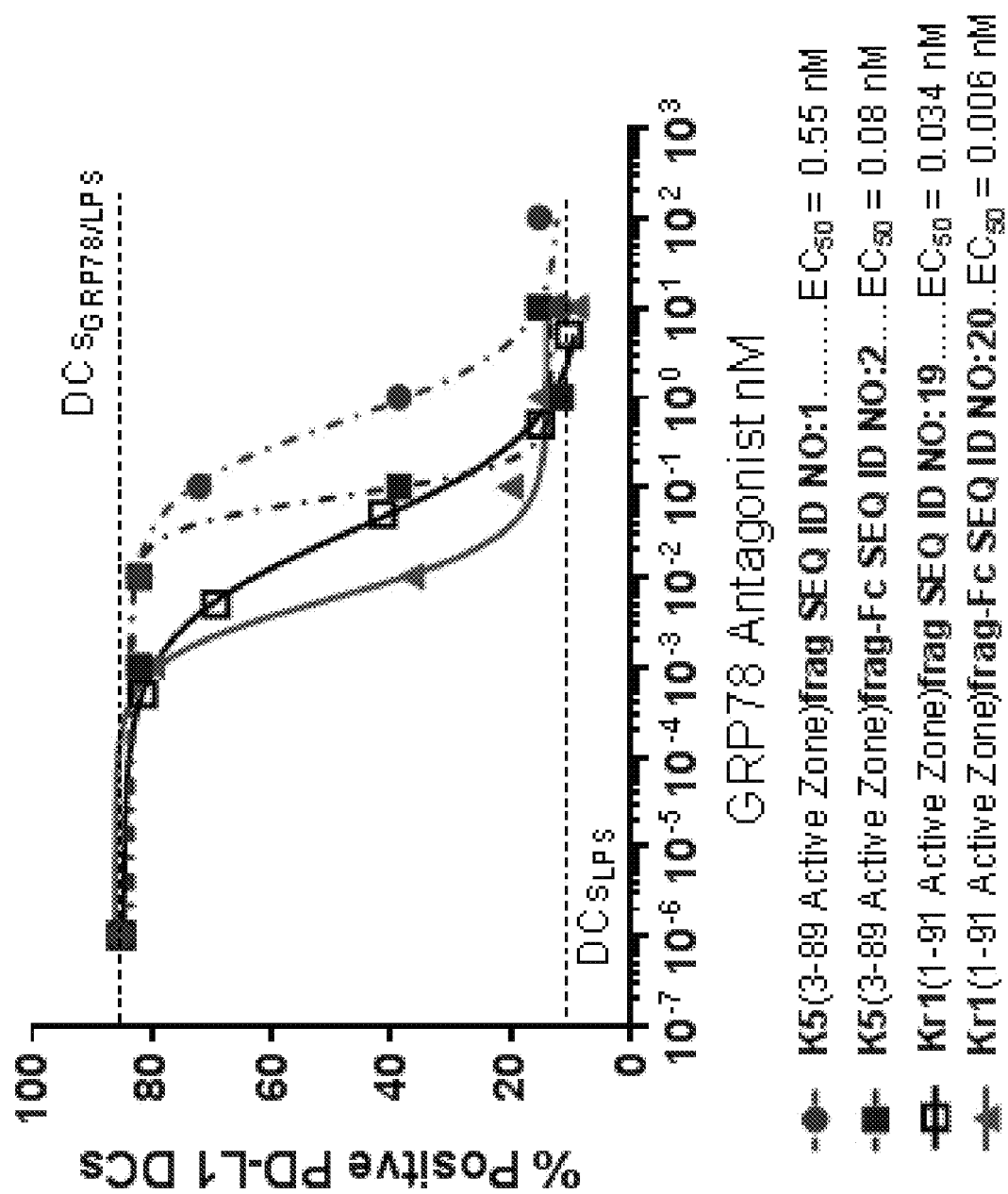
FIG. 9B depicts inhibition of PD-L1(B7H1) expression on GRP78/LPS treated DCs, by flow cytometry, as a function of increasing concentrations or GRP78 antagonists where (green -●-) K5(3-89 Active Zone)frag SEQ ID NO: 1; (blue -■-) K5(3-89 Active Zone)frag-Fc SEQ ID NO:2; (black -⊟-) Kr1(1-91 Active Zone)frag SEQ ID NO:19; and (red -▲-) Kr1(3-91 Active Zone)frag-Fc SEQ ID NO:20.
Figure 9C:
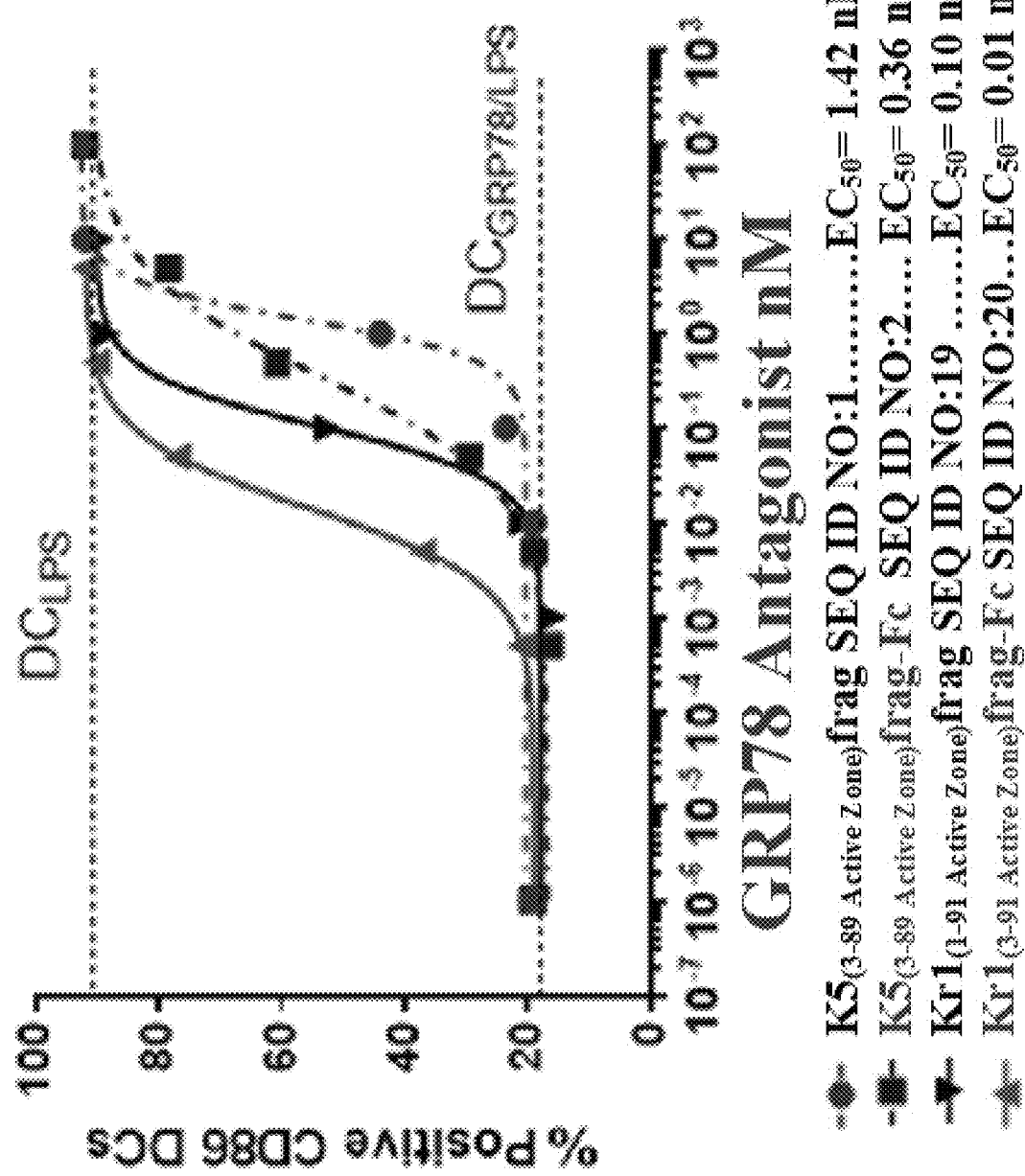
FIG. 9C depicts GRP78 antagonists augment the expression of maturity marker CD86 on DCs treated with GRP78 and LPS where (green -●-) K5(3-89 Active Zone)frag SEQ ID NO: 1; (blue -■-) K5(3-89 Active Zone)frag-Fc SEQ ID NO:2; (black -▼-) Kr1(1-91 Active Zone)frag SEQ ID NO:19; and (red -▲-) Kr1(3-91 Active Zone)frag-Fc SEQ ID NO:20.

FIG. 9A-9C illustrates increasing amounts of the GRP78 antagonists result in blocking GRP78 which reduces checkpoint protein expression on DCs. A tolerogenic dendritic cell phenotype is induced by soluble GRP78 binding. Myeloid CD14+ cells were co-stimulated for 7 days with IL-4, and GMCSF. On day 5 LPS along with or without GRP78 and GRP78 antagonists were added. On day 8, dendritic cells were fixed and stained for flow cytometry. The percent of B7H3, PD-L1, CD86 was measured by flowcytometry and compared to GRP78 untreated dendritic cells. FIG. 9A shows that inhibition of B7H3 expression on tolerogenic dendritic cells with increasing concentrations of GRP78 antagonists. It found that the antagonist Kr1(1-91 Active Zone)frag SEQ ID NO:19 is more potent by at least 65 times more than K5(3-89 Active Zone)frag SEQ ID NO:1 in blocking B7H3 when DCs are exposed to GRP78. FIG. 9B shows the inhibition of PD-L1(B7H1) expression on tolerogenic dendritic cells with increasing concentrations of K5(3-89 Active Zone)frag SEQ ID NO:1, Kr1(1-91 Active Zone) frag SEQ ID NO:19, K5(3-89 Active Zone)frag-Fc SEQ ID NO:2, and Kr1(3-91 Active Zone)frag-Fc SEQ ID NO:20. FIG. 9C shows increased expression of CD86 maturity marker on tolerogenic dendritic cells with increasing concentrations of K5(3-89 Active Zone)frag SEQ ID NO:1, Kr1(1-91 Active Zone)frag SEQ ID NO:19, K5(3-89 Active Zone)frag-Fc SEQ ID NO:2, and Kr1(3-91 Active Zone) frag-Fc SEQ ID NO:20.

Figure 10:
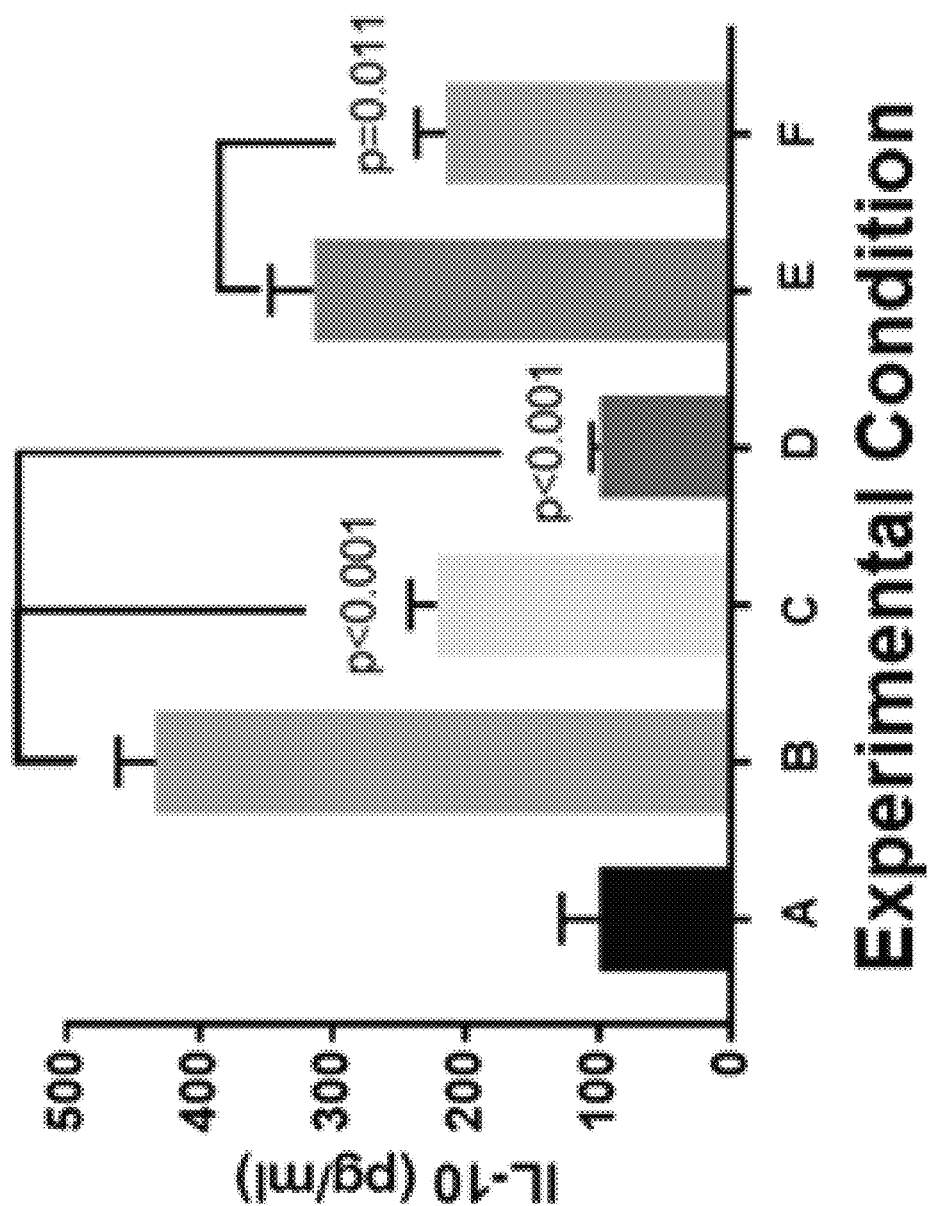
FIG. 10 is a bar chart showing different experimental conditions on DCs treated with K5(3-89 Active Zone)frag SEQ ID NO:1 and Kr1(1-91 Active Zone)frag SEQ ID NO:19 exposed to GRP78 influences IL-10 expression.

As shown in bar chart FIG. 10, elimination of IL-10 expression of tolerogenic dendritic cells by GRP78 antagonists, K5(3-89 Active Zone)frag SEQ ID NO:1 and Kr1(1-91 Active Zone)frag SEQ ID NO:19 under various experimental condition states of A, B, C, D, E, and F.

Experimental Condition state A corresponds to IDC being present in which LPS, GRP78, K5(3-89 Active Zone) frag SEQ ID NO:1, and Kr1(1-91 Active Zone)frag SEQ ID NO:19 are not present.

Experimental Condition state B corresponds to IDC and GRP78 being present in which LPS, K5(3-89 Active Zone)frag SEQ ID NO:1, and Kr1(1-91 Active Zone) frag SEQ ID NO:19 are not present.

Experimental Condition state C corresponds to IDC and GRP78 being present in which K5(3-89 Active Zone) frag SEQ ID NO:1 is present at 100 nM and LPS and Kr1(1-91 Active Zone)frag SEQ ID NO:19 are not present.

Experimental Condition state D corresponds to IDC and GRP78 being present in which Kr1(1-91 Active Zone) frag SEQ ID NO:19 is present at 100 nM and that LDS and K5(3-89 Active Zone)frag SEQ ID NO:1 is not present.

Experimental Condition state E corresponds to GRP78 and LPS are both present in which K5(3-89 Active Zone)frag SEQ ID NO:1 and Kr1(1-91 Active Zone) frag SEQ ID NO:19 are not present.

Experimental Condition state F corresponds to IDC, LPS, GRP78 and being present K5(3-89 Active Zone)frag SEQ ID NO:1 at 100 nm in which Kr1(1-91 Active Zone)frag SEQ ID NO:19 is not present.

It can be concluded that either K5(3-89 Active Zone)frag SEQ ID NO:1 or Kr1(1-91 Active Zone)frag SEQ ID NO: 19 reverses non-inflammatory, immature tolerogenic phenotype DCs induced by GRP78 binding.

Figure 11:
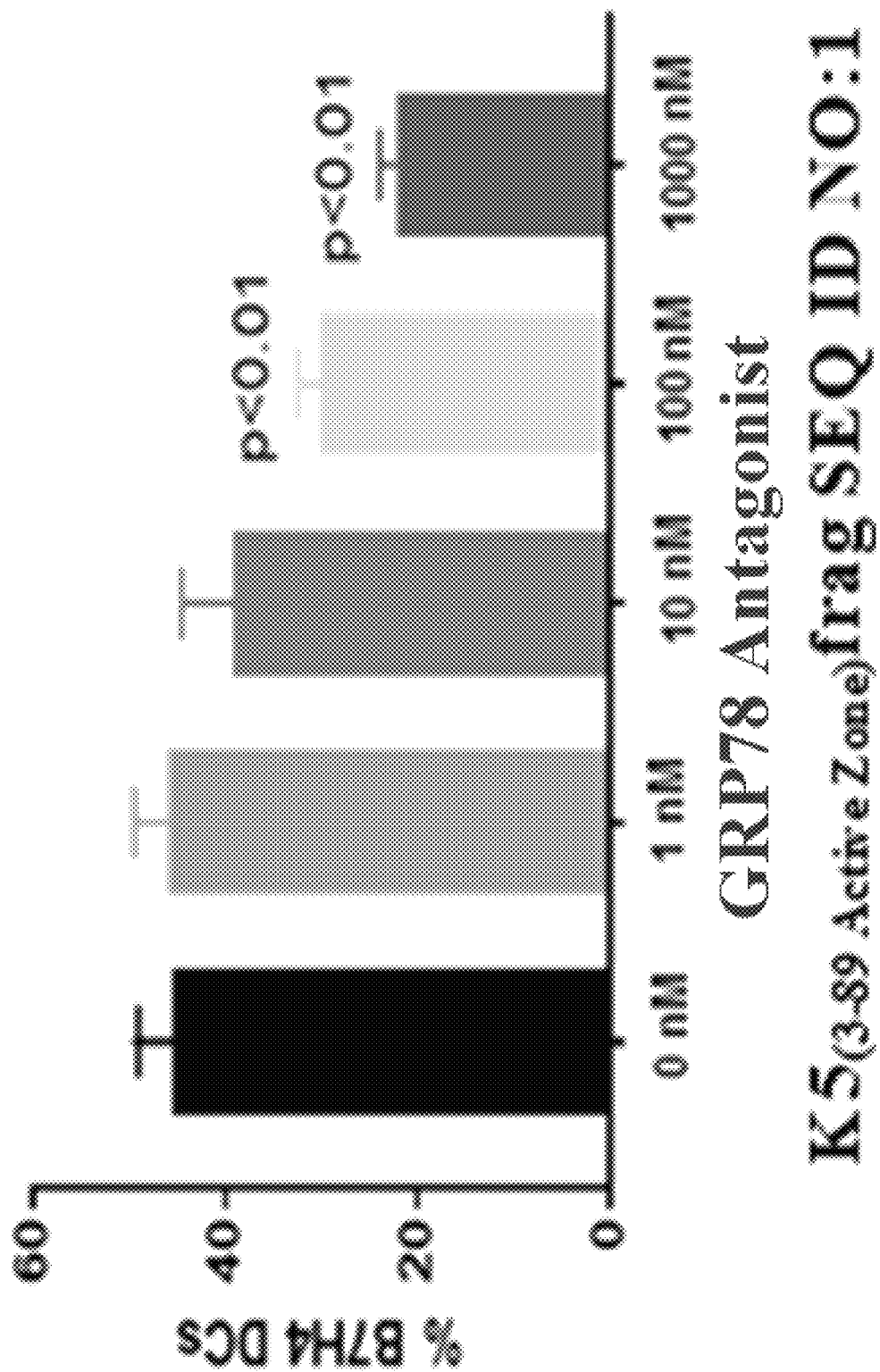
FIG. 11 is a bar chart showing increasing K5 concentrations affecting the percentage of B7H4 DCs showing that K5(3-89 Active Zone)frag SEQ ID NO:1 exposed to the GRP78 treated DCs results in decreased percentages of the expressed B7H4+ marker.

FIG. 11 illustrates increasing amounts of K5(3-89 Active Zone)frag SEQ ID NO:1 exposed to the GRP78 treated DC result in decreased percentages of the B7H4+ marker expressed.

Figure 12:
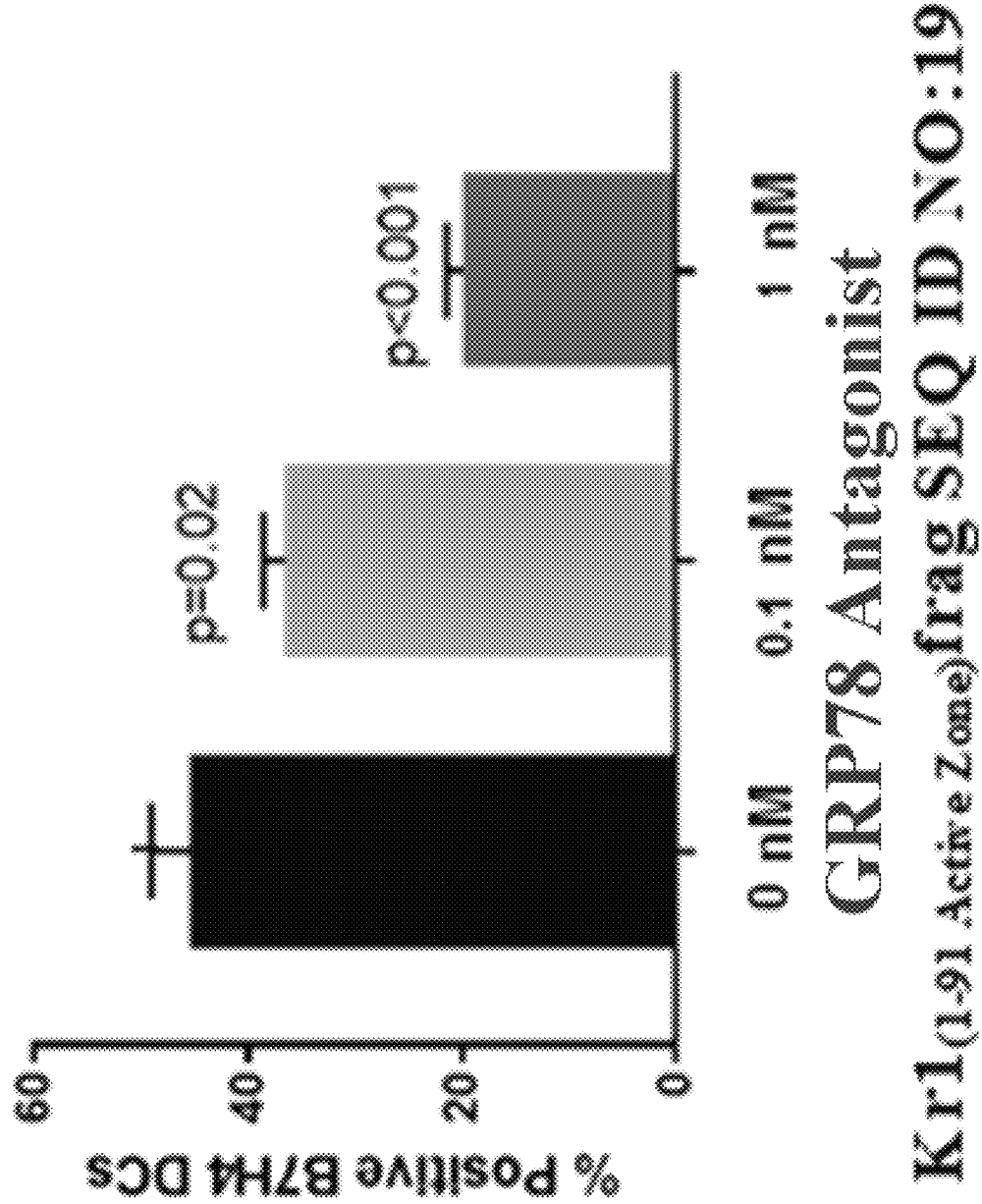
FIG. 12 is a bar chart showing that increasing concentrations of Kr1(1-91 Active Zone)frag SEQ ID NO: 19 exposed to the GRP78 treated DC result in decreasing percentages of the B7H4+ marker released by DC treated with GRP78.

FIG. 12 illustrates increasing concentrations of Kr1(1-91 Active Zone)frag SEQ ID NO:19 exposed to the GRP78 treated DCs result in decreasing percentages of the B7H4+ marker expressed by DCs treated with GRP78.

Figure 13:
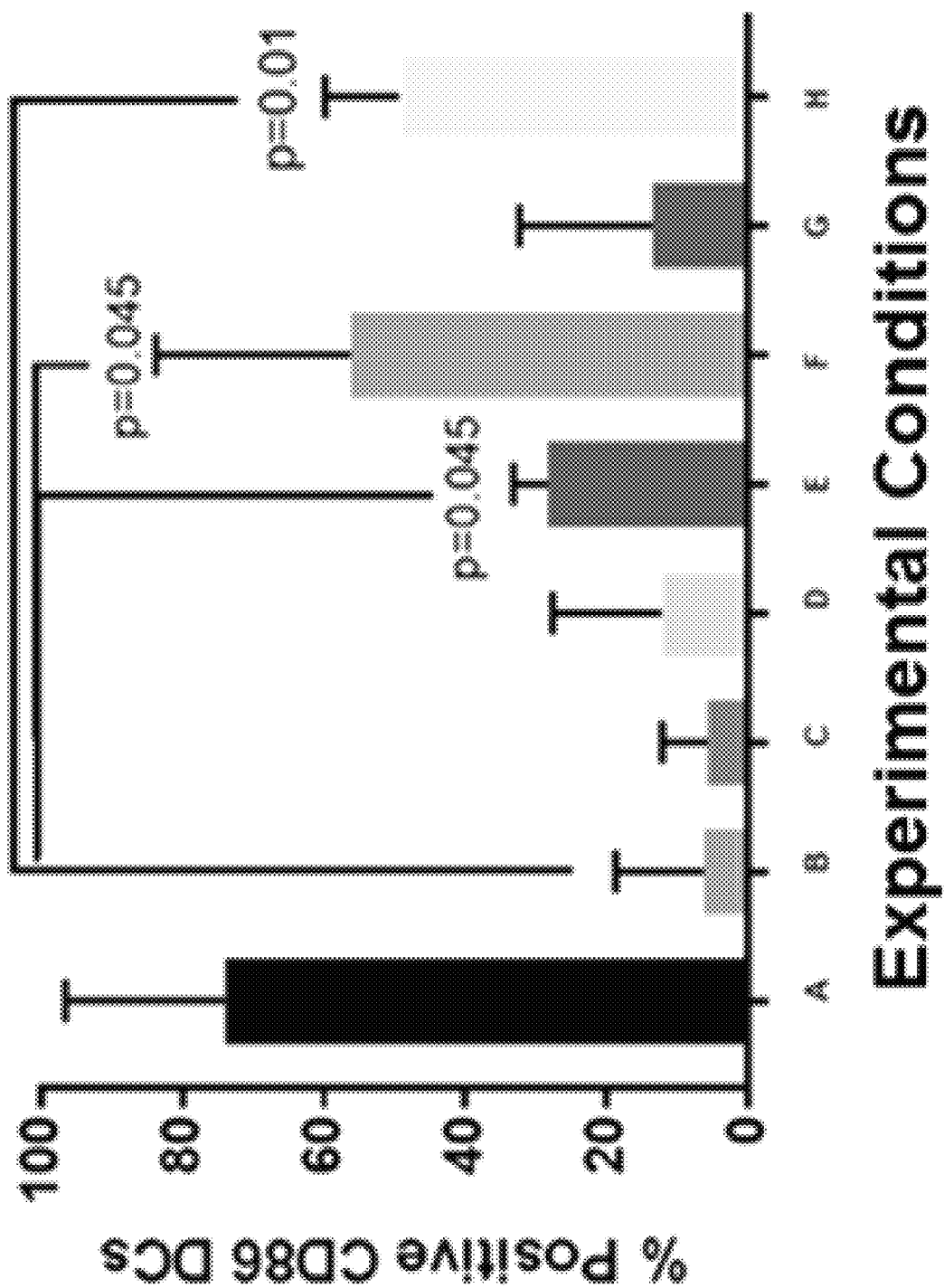
FIG. 13 is a bar chart showing different experimental treatment conditions on DCs exposed to GRP78/LPS with either K5(3-89 Active Zone)frag SEQ ID NO:1 or Kr1(1-91 Active Zone)frag SEQ ID NO:19 results in increases in the maturity marker CD86.

As shown in FIG. 13 treating DCs exposed to GRP78/LPS with either K5 or Kr1(1-91 Active Zone)frag SEQ ID NO: 19 results in increases in the maturity marker CD86. These changes in CD86 expression are shown at various experimental conditions.

Experimental Condition state A corresponds to IDC being present in which LPS, GRP78, K5(3-89 Active Zone) frag SEQ ID NO:1, and Kr1(1-91 Active Zone)frag SEQ ID NO:19 are not present.

Experimental Condition state B corresponds to IDC and LPS and being present in which GRP78, K5(3-89 Active Zone)frag SEQ ID NO:1, and Kr1(1-91 Active Zone)frag SEQ ID NO:19 are not present.

Experimental Condition state C corresponds to IDC, LPS, and GRP78 are present and K5(3-89 Active Zone)frag SEQ ID NO:1 is also present at a concentration of 1 nM; and Kr1(1-91 Active Zone)frag SEQ ID NO: 19 is not present.

Experimental Condition state D corresponds to IDC, LPS, and GRP78 are present and K5(3-89 Active Zone)frag SEQ ID NO:1 is also present at a concentration of 10 nM and that Kr1(1-91 Active Zone)frag SEQ ID NO: 19 is not present.

Experimental Condition state E corresponds to IDC, LPS, and GRP78 are present and K5(3-89 Active Zone)frag SEQ ID NO:1 is also present at a concentration of 100 nM and that Kr1(1-91 Active Zone)frag SEQ ID NO: 19 is not present.

Experimental Condition state F corresponds to IDC, LPS, and GRP78 are present and K5(3-89 Active Zone)frag SEQ ID NO:1 is also present at a concentration of 1000 nM and that Kr1(1-91 Active Zone)frag SEQ ID NO: 19 is not present.

Experimental Condition state G corresponds to IDC, LPS, and GRP78 are present and Kr1(1-91 Active Zone)frag SEQ ID NO: 19 is also present at a concentration of 0.1 nM and that K5(3-89 Active Zone)frag SEQ ID NO:1 is not present.

Experimental Condition state H corresponds to IDC, LPS, GRP78 being present in which Kr1(1-91 Active Zone) frag SEQ ID NO:19 is present at 1 nM and that K5(3-89 Active Zone)frag SEQ ID NO:1 is not present.

It can be concluded that GRP78 binding to DCs induces an immature (decreased expression) CD86-toleragenic phenotype that is resistant to LPDS stimulation. It can also be concluded that treatment with either K5(3-89 Active Zone) frag SEQ ID NO:1 or Kr1(1-91 Active Zone)frag SEQ ID NO:19 to DCs exposed to GRP78 completely reverses this phenotype by increased CD86 expression.

Figure 14:
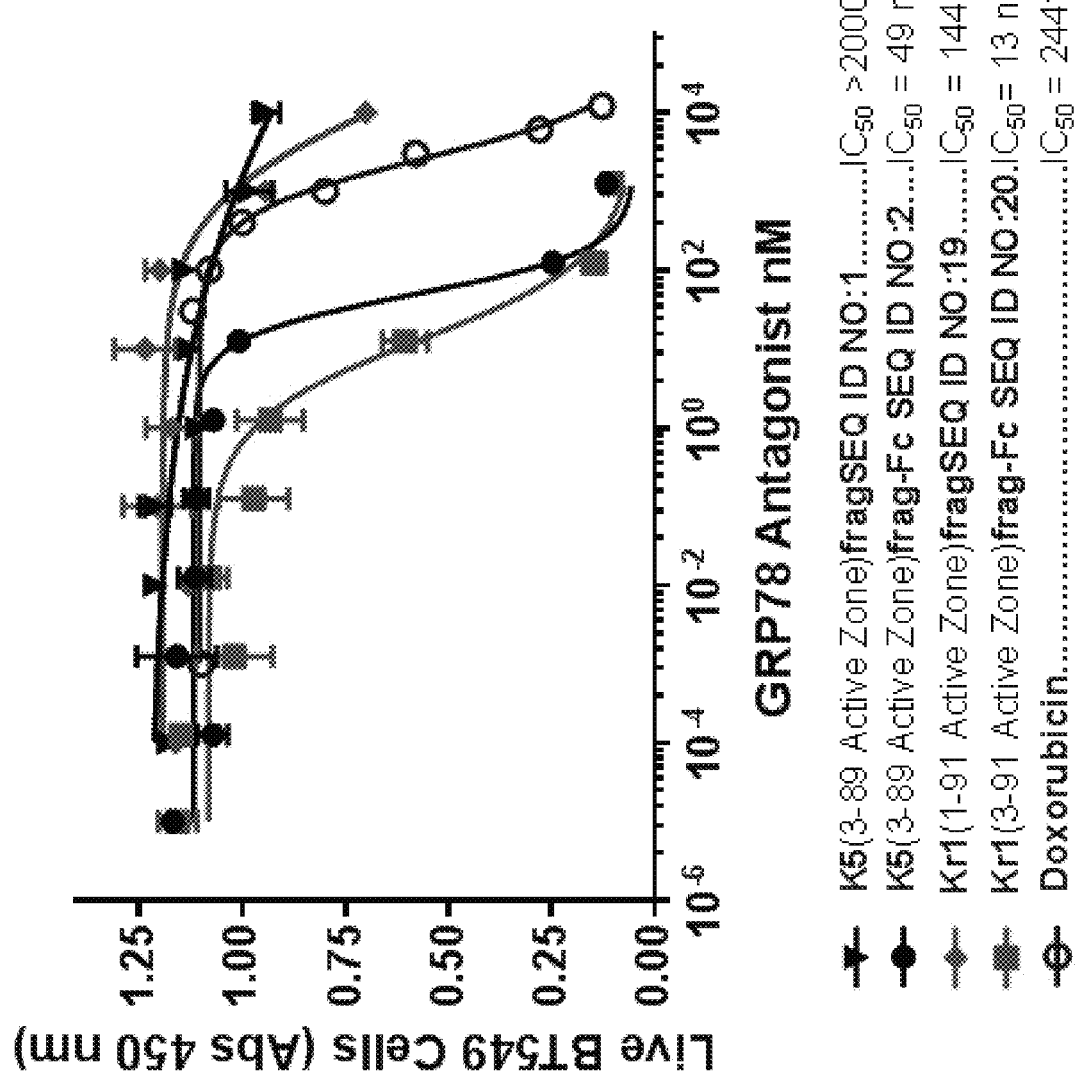
FIG. 14 inhibition of BT549 breast cancer cell proliferation with GRP antagonist (black -▼-) K5(3-89 Active Zone) frag SEQ ID NO: 1; (blue -●-) K5(3-89 Active Zone)frag-Fc SEQ ID NO:2; (red -◆-) Kr1(1-91 Active Zone)frag SEQ ID NO:19; (red -■-) Kr1(3-91 Active Zone)frag-Fc SEQ ID NO:20; and (blue -◈-) Doxorubicin.

FIG. 14 illustrates how a GRP78 antagonist inhibits the proliferation of BT549 human breast cancer cells. The inhibition effect of GRP78 antagonist on metastatic triple-negative, chemo-resistant BT549 cells was assessed using a proliferation assay. 5,000 cells per well were added to each well of a 96-well microplate with full media and incubated overnight. Then GRP78 (10 ug/ml) and various concentrations of K5(3-89 Active Zone)frag SEQ ID NO: 1, K5(3-89 Active Zone)frag-Fc SEQ ID NO:2, Kr1(1-91 Active Zone) frag SEQ ID NO:19, Kr1(3-91 Active Zone)frag-Fc SEQ ID NO:20 were also added and incubated at 8% CO2 for 5 days. Relative cell numbers in each well of a 96-well microplate after incubation were determined by using WST-8 proliferation assay (Cell Counting Kit-8, Sigma, MO). The half maximal inhibitory concentration of Kr1(3-91 Active Zone) frag-Fc SEQ ID NO:20 of inhibiting the growth of mouse breast cancer cells, 4T1 was found to be at $IC_{50}$=7 nM. The half maximal inhibitory concentration of K5(3-89 Active Zone)frag SEQ ID NO:1 of inhibiting the growth of the chemo-resistant human breast cancer cells (BT549) was found to be at IC$_{50}$>20000 nM. The half maximal inhibitory concentration of K5(3-89 Active Zone)frag-Fc SEQ ID NO:2 of inhibiting the growth of the chemo-resistant human breast cancer cells (BT549) was found to be at IC$_{50}$=49 nM. The half maximal inhibitory concentration of Kr1(1-91 Active Zone)frag SEQ ID NO: 19 of inhibiting the growth of the chemo-resistant human breast cancer cells (BT549) was found to be at IC$_{50}$=14400 nM. The half maximal inhibitory concentration of Kr1(3-91 Active Zone)frag-Fc SEQ ID NO:20 of inhibiting the growth of the chemo-resistant human breast cancer cells (BT549) was found to be at IC$_{50}$=13 nM. The half maximal inhibitory concentration of Doxorubicin of inhibiting the growth of the chemo-resistant human breast cancer cells (BT549) was found to be at IC$_{50}$=2441 nM. The results are graphically presented in FIG. 14 as absorbance for live cells and also summarized in Table 1. In all cases the GRP78 antagonists were found to potently block the proliferation of BT549 metastatic breast cancer cells more potently than standard of care Doxorubicin.

Figure 15:
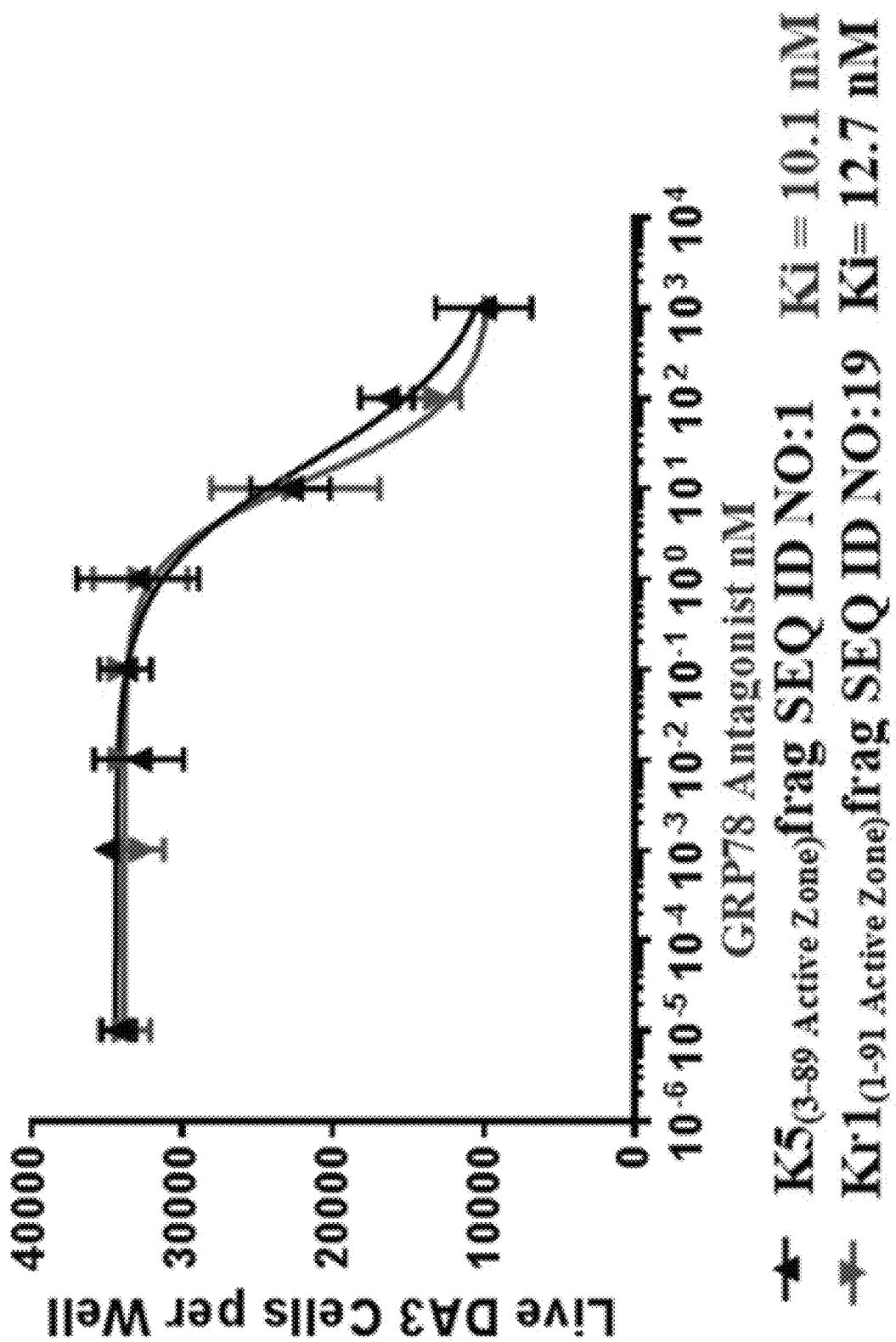
FIG. 15 inhibition of Mouse DA3 breast cancer proliferation with GRP antagonist (black -▲-) K5(3-89 Active Zone)frag SEQ ID NO:1 and (red -▼-) Kr1(1-91 Active Zone)frag SEQ ID NO:19.

FIG. 15 illustrates the inhibition of live Mouse DA3 breast cancer proliferation with GRP antagonist K5(3-89 Active Zone)frag SEQ ID NO:1 and Kr1(1-91 Active Zone) frag SEQ ID NO:19 in which 5000 cells per well were added to 96 well plates with GRP78 antagonist. The cells were grown for 5 days and the numbers of live cells analyzed by a WST-1 proliferation assay.

Figure 16:
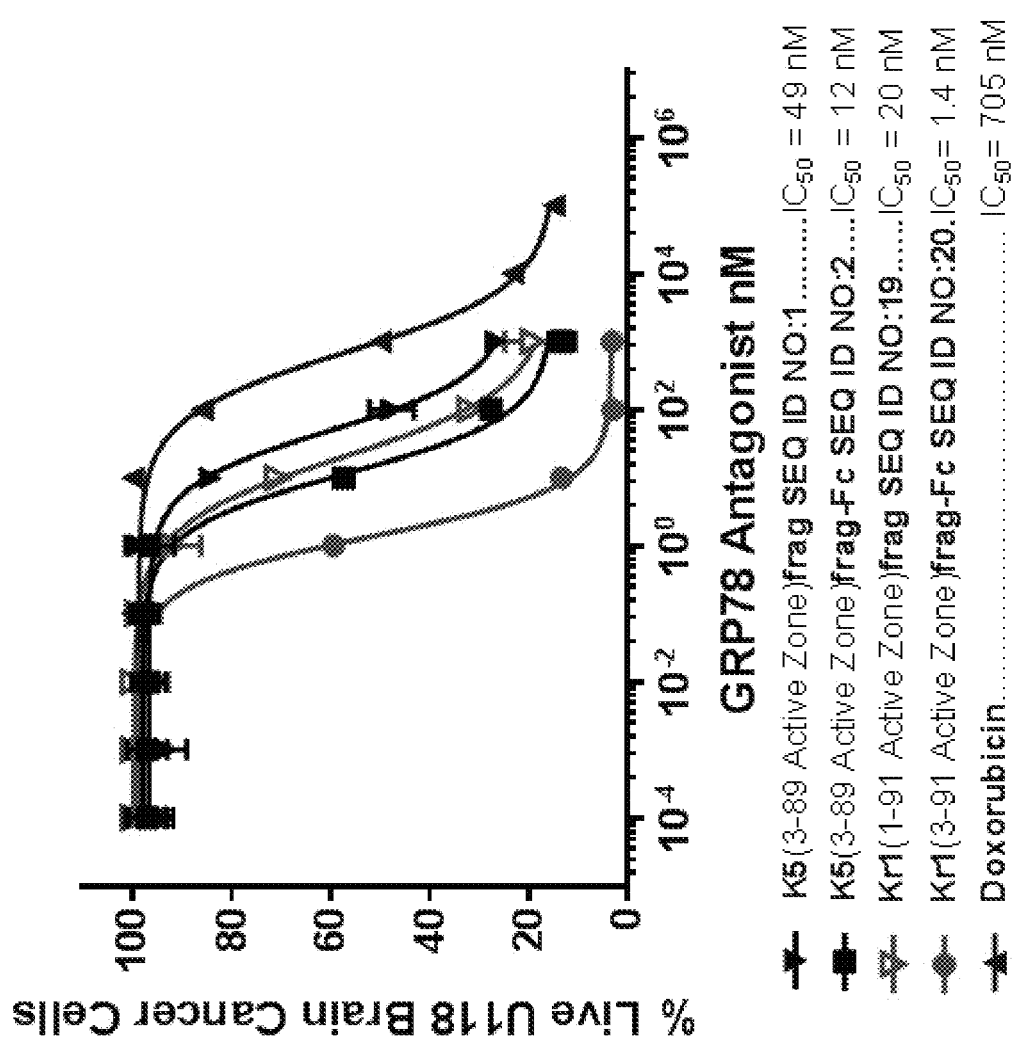
FIG. 16 inhibition of U118 glioma cell line proliferation with GRP antagonist (black -▼-) K5(3-89 Active Zone)frag SEQ ID NO: 1; (black -■-) K5(3-89 Active Zone)frag-Fc SEQ ID NO:2; (red -◈-) Kr1(1-91 Active Zone)frag SEQ ID NO:19; (red -●-) Kr1(3-91 Active Zone)frag-Fc SEQ ID NO:20; and (blue -▲-) Doxorubicin.

FIG. 16 illustrates how a GRP78 antagonist inhibits the proliferation of U-118 MG glioblastoma cell proliferation. The effect of GRP78 antagonist on glioma stage IV, chemo-resistant U-118 MG cells was assessed using a proliferation assay. 5,000 cells per well were added to each well of a 96-well microplate with full media and incubated overnight. Then GRP78 (10 ug/ml) and various concentrations of K5(3-89 Active Zone)frag SEQ ID NO:1, K5(3-89 Active Zone)frag-Fc SEQ ID NO:2, Kr1(1-91 Active Zone)frag SEQ ID NO:19, Kr1(3-91 Active Zone)frag-Fc SEQ ID NO:20 were also added and incubated at 8% CO2 for 5 days. Relative cell numbers in each well of a 96-well microplate after incubation were determined by using WST-8 proliferation assay (CCK-8, Sigma, MO). The half maximal inhibitory concentration of K5(3-89 Active Zone)frag SEQ ID NO:1 of inhibiting the growth of glioma stage IV, chemo-resistant (U-118 MG) cells was found to be at IC$_{50}$=49 nM. The half maximal inhibitory concentration of K5(3-89 Active Zone)frag-Fc SEQ ID NO:2 of inhibiting the growth of glioma stage IV, chemo-resistant (U-118 MG) cells was found to be at IC$_{50}$=12 nM. The half maximal inhibitory concentration of Kr1(1-91 Active Zone)frag SEQ ID NO: 19 of inhibiting the growth of glioma stage IV, chemo-resistant (U-118 MG) cells was found to be at IC$_{50}$=20 nM. The half maximal inhibitory concentration of Kr1(3-91 Active Zone) frag-Fc SEQ ID NO:20 of inhibiting the growth of glioma stage IV, chemo-resistant (U-118 MG) cells was found to be at IC$_{50}$=1.4 nM. The half maximal inhibitory concentration of Doxorubicin of inhibiting the growth of glioma stage IV, chemo-resistant (U-118 MG) cells was found to be at IC$_{50}$=705 nM. Results are graphically presented as the percent of control cell (full media) proliferation in FIG. 16 and summarized in Table 1 in which it is clear that the all of the tested GRP78 antagonist significantly block proliferation of glioblastoma cells better than the cytotoxic drug, Doxorubicin.

Figure 20:
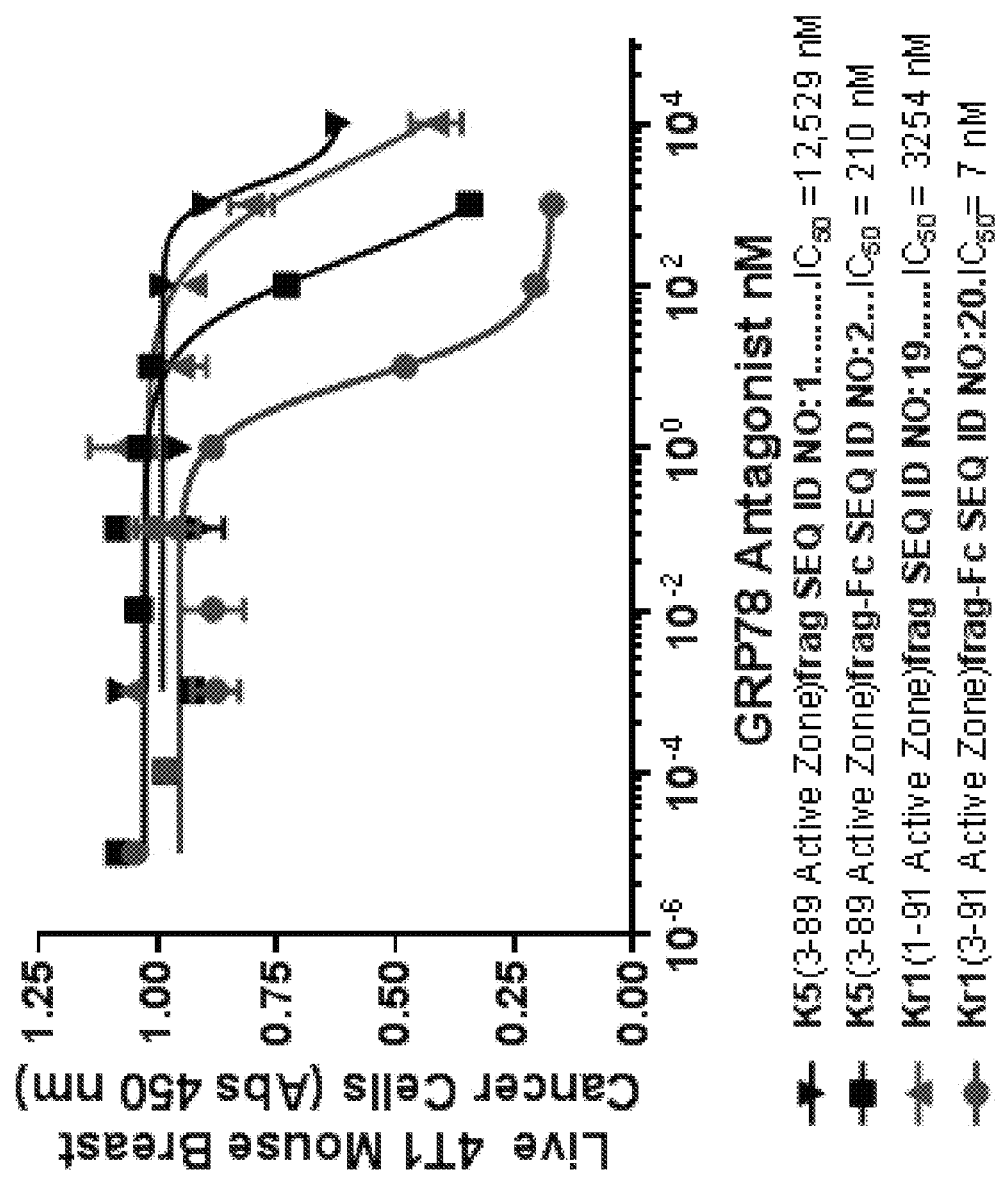
FIG. 20 inhibition of mouse breast cancer cells (4T1) with GRP antagonists (black -▼-) K5(3-89 Active Zone)frag SEQ ID NO: 1; (black -■-) K5(3-89 Active Zone)frag-Fc SEQ ID NO:2; (red -▲-) Kr1(1-91 Active Zone)frag SEQ ID NO:19; and (red -●-) Kr1(3-91 Active Zone)frag-Fc SEQ ID NO:20.

FIG. 20 illustrates how GRP78 antagonist, Kr1-Fc, K5-Fc, Kr1 and K5 inhibit 4T1 Mouse Breast Cancer Cell proliferation. The effect of GRP78 antagonist on mouse breast cancer cells, 4T1, was assessed using a proliferation assay. 5,000 cells per well were added to each well of a 96-well microplate with full media and incubated overnight. Then GRP78 (10 ug/ml) and various concentrations of K5(3-89 Active Zone)frag SEQ ID NO:1, K5(3-89 Active Zone)frag-Fc SEQ ID NO:2, Kr1(1-91 Active Zone)frag SEQ ID NO:19, Kr1(3-91 Active Zone)frag-Fc SEQ ID NO:20 were also added and incubated at 8% CO2 for 5 days. Relative cell numbers in each well of a 96-well microplate after incubation were determined by using WST-8 proliferation assay (CCK-8, Sigma, MO). The half maximal inhibitory concentration of K5(3-89 Active Zone)frag SEQ ID NO:1 of inhibiting the growth of mouse breast cancer cells, 4T1 was found to be at IC$_{50}$=12,529 nM. The half maximal inhibitory concentration of K5(3-89 Active Zone)frag-Fc SEQ ID NO:2 of inhibiting the growth of mouse breast cancer cells, 4T1 was found to be at IC$_{50}$=210 nM. The half maximal inhibitory concentration of Kr1(1-91 Active Zone) frag SEQ ID NO:19 of inhibiting the growth of mouse breast cancer cells, 4T1 was found to be at IC$_{50}$=3254 nM. The half maximal inhibitory concentration of Kr1(3-91 Active Zone) frag-Fc SEQ ID NO:20 of inhibiting the growth of mouse breast cancer cells, 4T1 was found to be at IC$_{50}$=7 nM. The half maximal inhibitory concentration of Doxorubicin of inhibiting the growth of mouse breast cancer cells, 4T1 was found to be at IC$_{50}$=7 nM. Results are graphically presented in FIG. 20 as the absorbance of live cells in the wells with an average of 3 replicates and summarized in Table 1.

Figure 21:
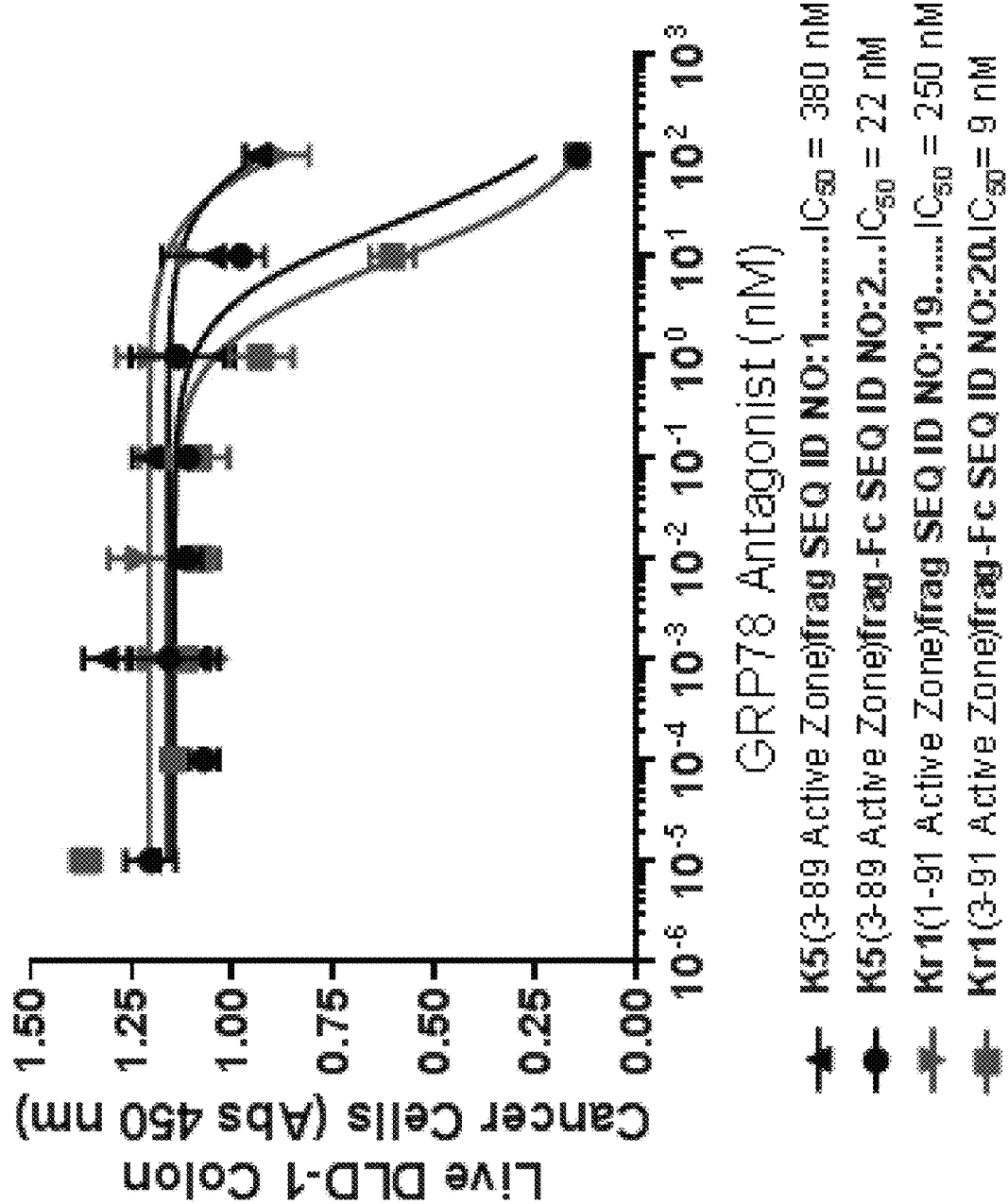
FIG. 21 inhibition of chemo-resistant colon cancer cells (DLD-1) with GRP antagonists (black -▲-) K5(3-89 Active Zone)frag SEQ ID NO: 1; (black -●-) K5(3-89 Active Zone)frag-Fc SEQ ID NO:2; (red -▼-) Kr1(1-91 Active Zone)frag SEQ ID NO:19; and (red -■-) Kr1(3-91 Active Zone)frag-Fc SEQ ID NO:20.

FIG. 21 illustrates how GRP78 antagonist, Kr1-Fc, K5-Fc, Kr1 and K5 inhibit DLD-1 colon cancer cell proliferation. The effect of GRP78 antagonist on stage IV, chemo-resistant colon cancer cells, DLD-1, was assessed using a proliferation assay. 3,000 cells per well were added to each well of a 96-well microplate with full media and incubated overnight. Then GRP78 (10 ug/ml) and various concentrations of K5(3-89 Active Zone)frag SEQ ID NO: 1, K5(3-89 Active Zone)frag-Fc SEQ ID NO:2, Kr1(1-91 Active Zone) frag SEQ ID NO:19, Kr1(3-91 Active Zone)frag-Fc SEQ ID NO:20 were also added and incubated at 8% CO2 for 5 days. Relative cell numbers in each well of a 96-well microplate after incubation were determined by using WST-8 proliferation assay (CCK-8, Sigma, MO). The half maximal inhibitory concentration of K5(3-89 Active Zone)frag SEQ ID NO:1 of inhibiting the growth of chemo-resistant colon cancer cells (DLD-1) was found to be at IC$_{50}$=350 nM. The half maximal inhibitory concentration of K5(3-89 Active Zone)frag-Fc SEQ ID NO:2 of inhibiting the growth of chemo-resistant colon cancer cells (DLD-1) was found to be at IC$_{50}$=22 nM. The half maximal inhibitory concentration of Kr1(1-91 Active Zone)frag SEQ ID NO:19 of inhibiting the growth of chemo-resistant colon cancer cells (DLD-1) was found to be at IC$_{50}$=250 nM. The half maximal inhibitory concentration of Kr1(3-91 Active Zone)frag-Fc SEQ ID NO:20 of inhibiting the growth of chemo-resistant colon cancer cells (DLD-1) was found to be at IC$_{50}$=9 nM. The half maximal inhibitory concentration of Doxorubicin of inhibiting the growth of chemo-resistant colon cancer cells (DLD-1) was found to be at IC$_{50}$=7 nM. Results are presented in FIG. 21 as the absorbance of live cells per well averaged from triplicate wells and summarized in Table 1.

TABLE 1

Proliferation Inhibition (5 day) IC$_{50}$, nM

| Inhibitor | Breast Cancer BT549 | Brain Cancer U118 | Mouse Breast Cancer 4T1 | Mouse Breast Cancer DA3 | Colon Cancer DLD-1 |
|---|---|---|---|---|---|
| K5(3-89 Active Zone)frag SEQ ID NO: 1 | >20000 | 49 | 12529 | 10 | 380 |
| Kr1(1-91 Active Zone)frag SEQ ID NO: 19 | 14400 | 20 | 3254 | 13 | 250 |
| K5(3-89 Active Zone)frag-Fc SEQ ID NO: 2 | | 49 | 12 | 210 | NT* | 22 |
| Kr1(3-91 Active Zone)frag-Fc SEQ ID NO: 20 | | 13 | 1.4 | 7 | NT* | 9 |

*NT = Not Tested

Taking into account these definitions, observations and results, the present invention concerns modification of various kringle type peptide fragments to enhance their biological potency and/or to extend their functional half-life times by conjugating these fragments onto various protein carriers found in blood. One carrier of choice (but not limited to) for this invention is conjugating these kringle fragments onto immunoglobulin (Ig) prior to introducing these conjugates into the patient. Another carrier of choice is to derivatize these kringle peptide fragments with linker groups such that these modified fragments can subsequently conjugate with blood protein carriers when introduced into the patient. These fragments include plasminogen kringle 5 fragments, the first receptor tyrosine kinase-like orphan receptor (ROR1) fragments, and the second receptor tyrosine kinase-like orphan receptor (ROR2) fragments.

As used herein, the term "K5(3-89 Active Zone)frag" peptide SEQ ID NO:1 is understood to be a region of mammalian plasminogen that has a specific three-dimensional folding shape brought about by three disulfide bonds of the mammalian plasminogen molecule. It is important to note that the total length of the particular kringle 5 peptide may vary depending upon the way the kringle 5 peptide is enzymatically cleaved from the plasminogen. It is also understood that the sequence of the kringle 5 peptide may also vary slightly depending upon the species from which the plasminogen is obtained. One of the particular amino acid sequences of the kringle 5 peptide region of the present invention is this K5(3-89 Active Zone)frag SEQ ID NO:1.

As used herein, the term "Kr1(1-91 Active Zone)frag" peptide fragment SEQ ID NO:19 is understood to be a specific three-dimensional folding shape region in the first receptor tyrosine kinase-like orphan receptor (ROR1) that also has three disulfide bonds similar to that of the kringle region in mammalian plasminogen. It is important to note that the total length of the particular ROR1 kringle peptide portion may vary depending upon the way the ROR1 kringle peptide is enzymatically cleaved from the first receptor tyrosine kinase-like orphan receptor. It is also understood that the sequence of the ROR1 kringle peptide may also vary slightly depending upon the species from which the first receptor tyrosine kinase-like orphan receptor is obtained. One preferred particular amino acid sequence of the ROR1 kringle peptide region is Kr1(1-91 Active Zone)frag SEQ ID NO:19.

As used herein, the term "Kr2(1-85 Active Zone)frag" peptide fragment SEQ ID NO:33 is understood to be a specific three-dimensional folding shape region in the second receptor tyrosine kinase-like orphan receptor (ROR2) that also has three disulfide bonds similar to that of the kringle region in mammalian plasminogen. It is important to note that the total length of the particular ROR2 kringle peptide portion may vary depending upon the way the ROR2 kringle peptide portion is enzymatically cleaved from the second receptor tyrosine kinase-like orphan receptor. It is also understood that the sequence of the ROR2 kringle peptide may also vary slightly depending upon the species from which the second receptor tyrosine kinase-like orphan receptor is obtained. One particular amino acid sequence of the ROR2 kringle peptide region disclosed is Kr2(1-85 Active Zone)frag" SEQ ID NO:33.

1. Kringle Fragments Conjugated with Immunoglobulin (Fusion Conjugates)

Some preferred kringle 5 plasminogen fragments (i.e., K5-frag-Fc fusion complexes) that are directedly conjugated to immunoglobulin include but not limited to the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

As used herein, the term "K5(3-89 Active Zone)frag-Fc" fusion peptide complex corresponds to the 3-89 amino acid sequence of the K5(1-91 Active Zone)frag peptide (SEQ ID NO: 189) and which this 3-89 amino acid sequence portion of the K5(1-91 Active Zone)frag peptide (SEQ ID NO:189) peptide is bound to immunoglobulin via a peptide bond. This K5(3-89 Active Zone)frag-Fc fusion complex is described in detail in SEQ ID NO:2.

As used herein, the term "K5(57-81 Active Zone)frag-Fc" fusion peptide complex correspond to the 57-81 amino acid sequence of the K5(1-91 Active Zone)frag peptide (SEQ ID NO: 189) and which this 57-81 amino acid sequence portion of the K5(1-91 Active Zone)frag peptide (SEQ ID NO: 189) peptide is bound to immunoglobulin via a peptide bond. This K5(57-81 Active Zone)frag-Fc fusion peptide complex is described in detail in SEQ ID NO:3.

As used herein, the term "K5(57-81 Active Zone w Ala sub Cys)frag-Fc" fusion peptide complex corresponds to the 57-81 amino acid sequence of the K5(1-91 Active Zone)frag peptide (SEQ ID NO:189) in which the two cysteine residues at the 69$^{th}$ and 81$^{st}$ amino acid positions are substituted with alanine and which this substituted 57-81 amino acid sequence portion of the K5(1-91 Active Zone)frag peptide (SEQ ID NO: 189) peptide is bound to immunoglobulin via a peptide bond. This K5(57-81 Active Zone w Ala sub Cys)frag-Fc fusion peptide complex is described in detail in SEQ ID NO:4.

As used herein, the term "K5(57-81 Active Zone w Val sub Cys)frag-Fc" fusion peptide complex corresponds to the 57-81 amino acid sequence of the K5(1-91 Active Zone)frag peptide (SEQ ID NO:189) in which the two cysteine residues at the 69$^{th}$ and 81$^{st}$ amino acid positions are substituted with valine and which this substituted 57-81 amino acid sequence portion of the K5(1-91 Active Zone)frag peptide (SEQ ID NO: 189) is bound to immunoglobulin via a peptide bond. This K5(57-81 Active Zone w Val sub Cys) frag-Fc fusion peptide complex is described in detail in SEQ ID NO:5.

As used herein, the term "K5(57-81 Active Zone w Ile sub Cys)frag-Fc" fusion peptide complex corresponds to the 57-81 amino acid sequence of the K5(1-91 Active Zone)frag peptide (SEQ ID NO:189) in which the two cysteine residues at the 69$^{th}$ and 81$^{st}$ amino acid positions are substituted with isoleucine and which this substituted 57-81 amino acid sequence portion of the K5(1-91 Active Zone)frag peptide (SEQ ID NO: 189) is bound to immunoglobulin via a peptide bond. This K5(57-81 Active Zone w Ile sub Cys)frag-Fc fusion peptide complex is described in detail in SEQ ID NO:6.

As used herein, the term "K5$_{(57\text{-}81\ Active\ Zone\ w\ Leu\ sub\ Cys)}$frag-Fc" fusion peptide complex corresponds to the 57-81 amino acid sequence of the K5(1-91 Active Zone)frag peptide (SEQ ID NO: 189) in which the two cysteine residues at the 69$^{th}$ and 81$^{st}$ amino acid positions are substituted with leucine and which this substituted 57-81 amino acid sequence portion of the K5(1-91 Active Zone)frag peptide (SEQ ID NO: 189) is bound to immunoglobulin via a peptide bond. This K5$_{(57\text{-}81\ Active\ Zone\ w\ Ile\ sub\ Cys)}$frag-Fc fusion peptide complex is described in detail in SEQ ID NO:7.

As used herein, the term "K5(70-89 Active Zone)frag-Fc" fusion peptide complex corresponds to the 70-89 amino acid sequence of the K5(1-91 Active Zone)frag peptide (SEQ ID NO: 189) and which this 70-89 amino acid sequence portion of the K5(1-91 Active Zone)frag (SEQ ID NO: 189) peptide is bound to immunoglobulin via a peptide bond. This "K5(70-89 Active Zone)frag-Fc" fusion peptide complex is described in detail in SEQ ID NO:8.

As used herein, the term "K5(70-89 Active Zone w Ala sub Cys)frag-Fc" fusion peptide complex corresponds to the 70-89 amino acid sequence of the K5(1-91 Active Zone)frag peptide (SEQ ID NO:189) in which the two cysteine residues at the 81$^{st}$ and 86' amino acid positions are substituted with alanine and which this substituted 70-89 amino acid sequence portion of the K5(1-91 Active Zone)frag peptide (SEQ ID NO: 189) is bound to immunoglobulin via a peptide bond. This "K5(70-89 Active Zone w Ala sub Cys)frag-Fc" peptide complex is described in detail in SEQ ID NO:9.

As used herein, the term "K5(70-89 Active Zone w Val sub Cys)frag-Fc" fusion peptide complex corresponds to the 70-89 amino acid sequence of the K5(1-91 Active Zone)frag peptide (SEQ ID NO:189) in which the two cysteine residues at the 81$^{st}$ and 86' amino acid positions are substituted with valine and which this substituted 70-89 amino acid sequence portion of the K5(1-91 Active Zone)frag peptide (SEQ ID NO: 189) is bound to immunoglobulin via a peptide bond. This K5(70-89 Active Zone w Val sub Cys)frag-Fc peptide complex is described in detail in SEQ ID NO: 10.

As used herein, the term "K5(70-89 Active Zone w Ile sub Cys)frag-Fc" fusion peptide complex corresponds to the 70-89 amino acid sequence of the K5(1-91 Active Zone)frag peptide (SEQ ID NO:189) in which the two cysteine residues at the 81$^{st}$ and 86$^{th}$ amino acid positions are substituted with isoleucine and which this substituted 70-89 amino acid sequence portion of the K5(1-91 Active Zone)frag peptide (SEQ ID NO: 189) is bound to immunoglobulin via a peptide bond. This K5(70-89 Active Zone w Ile sub Cys)frag-Fc peptide complex is described in detail in SEQ ID NO: 11.

As used herein, the term "K5(70-89 Active Zone w Leu sub Cys)frag-Fc" fusion peptide complex corresponds to the 70-89 amino acid sequence of the K5(1-91 Active Zone)frag peptide (SEQ ID NO:189) in which the two cysteine residues at the 81$^{st}$ and 86$^{th}$ amino acid positions are substituted with leucine and which this substituted 70-89 amino acid sequence portion of the K5(1-91 Active Zone)frag peptide (SEQ ID NO: 189) is bound to immunoglobulin via a peptide bond. This term K5(70-89 Active Zone w Leu sub Cys)frag-Fc peptide complex is described in detail in SEQ ID NO:12.

As used herein, the term "K5(74-89 Active Zone)frag-Fc" fusion peptide complex refers corresponds to the 74-89 amino acid sequence of the K5(1-91 Active Zone)frag peptide (SEQ ID NO:189) and which this 74-89 amino acid sequence portion of the K5(1-91 Active Zone)frag peptide (SEQ ID NO: 189) is bound to immunoglobulin via a peptide bond. This K5(74-89 Active Zone)frag-Fc fusion peptide complex is described in detail in SEQ ID NO:13.

As used herein, the term "K5(74-89 Active Zone w Ala sub Cys)frag-Fc" fusion peptide complex corresponds to the 74-89 amino acid sequence of the K5(1-91 Active Zone)frag peptide (SEQ ID NO:189) in which the two cysteine residues at the 81$^{st}$ and 86$^{th}$ amino acid positions are substituted with alanine and which this substituted 74-89 amino acid sequence portion of the K5(1-91 Active Zone)frag peptide (SEQ ID NO: 189) is bound to immunoglobulin via a peptide bond. This K5(74-89 Active Zone w Ala sub Cys)frag-Fc fusion peptide complex is described in detail in SEQ ID NO: 14.

As used herein, the term "K5(74-89 Active Zone w Val sub Cys)frag-Fc" fusion peptide complex corresponds to the 74-89 amino acid sequence of the K5(1-91 Active Zone)frag peptide (SEQ ID NO:189) in which the two cysteine residues at the 81$^{st}$ and 86$^{th}$ amino acid positions are substituted with valine and which this substituted 74-89 amino acid sequence portion of the K5(1-91 Active Zone)frag peptide (SEQ ID NO: 189) is bound to immunoglobulin via a peptide bond. This K5(74-89 Active Zone w Val sub Cys)frag-Fc fusion peptide complex is described in detail in SEQ ID NO:15.

As used herein, the term "K5(74-89 Active Zone w Ile sub Cys)frag-Fc" fusion peptide complex corresponds to the 74-89 amino acid sequence of the K5(1-91 Active Zone)frag peptide (SEQ ID NO:189) in which the two cysteine residues at the 81$^{st}$ and 86$^{th}$ amino acid positions are substituted with isoleucine and which this substituted 74-89 amino acid sequence portion of the K5(1-91 Active Zone)frag peptide (SEQ ID NO: 189) is bound to immunoglobulin via a peptide bond. This term K5(74-89 Active Zone w Ile sub Cys)frag-Fc fusion peptide complex is described in detail in SEQ ID NO:16.

As used herein, the term "K5(74-89 Active Zone w Leu sub Cys)frag-Fc" fusion peptide complex corresponds to the 74-89 amino acid sequence of the K5(1-91 Active Zone)frag peptide (SEQ ID NO:189) in which the two cysteine residues at the 81$^{st}$ and 86$^{th}$ amino acid positions are substituted with leucine and which this substituted 74-89 amino acid sequence portion of the K5(1-91 Active Zone)frag peptide (SEQ ID NO: 189) is bound to immunoglobulin via a peptide bond. This K5(74-89 Active Zone w Leu sub Cys)frag-Fc fusion peptide complex is described in detail in SEQ ID NO: 17.

As used herein, the term "K5(74-80 Active Zone)frag-Fc" fusion peptide complex corresponds to the 74-80 amino acid sequence of the K5(1-91 Active Zone)frag peptide (SEQ ID NO: 189) and which this 74-80 amino acid sequence portion of the K5(1-91 Active Zone)frag peptide (SEQ ID NO:189) is bound to immunoglobulin via a peptide bond. This K5(74-80 Active Zone)frag-Fc fusion peptide complex is described in detail in SEQ ID NO:18.

Some preferred ROR1 kringle fragments from the first receptor tyrosine kinase-like orphan receptor (ROR1) conjugated to immunoglobulin (i.e., the Kr1-frag-Fc fusion peptide complexes) include but not limited to the peptide sequences selected from the group consisting of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, and SEQ ID NO:32.

As used herein, the term "Kr1(3-91 Active Zone)frag-Fc" fusion peptide complex corresponds to the 3-91 amino acid sequence of the Kr1(1-91 Active Zone)frag SEQ ID NO: 19 and which this 3-91 amino acid sequence portion of the Kr1(1-91 Active Zone)frag SEQ ID NO: 19 is bound to immunoglobulin via a peptide bond. This Kr1(3-91 Active Zone)frag-Fc fusion peptide complex is described in detail in SEQ ID NO:20.

As used herein, the term "Kr1(58-91 Active Zone)frag-Fc" fusion peptide complex correspond to the 58-91 amino acid sequence of the Kr1(1-91 Active Zone)frag SEQ ID NO: 19 and which this 58-91 amino acid sequence portion of the Kr1(1-91 Active Zone)frag SEQ ID NO: 19 is bound to immunoglobulin via a peptide bond. This Kr1(58-91 Active Zone)frag-Fc fusion peptide complex is described in detail in SEQ ID NO:21.

As used herein, the term "Kr1(58-91 Active Zone w Ala sub Cys)frag-Fc" fusion peptide complex corresponds to the 58-91 amino acid sequence of the Kr1(1-91 Active Zone) frag SEQ ID NO: 19 in which three cysteine residues at the $69^{th}$, the $81^{st}$ and the $86^{th}$ amino acid positions are substituted with alanine and which this substituted 58-91 amino acid sequence portion of the Kr1(1-91 Active Zone)frag SEQ ID NO:19 is bound to immunoglobulin via a peptide bond. This Kr1(58-91 Active Zone w Ala sub Cys)frag-Fc fusion peptide complex is described in detail in SEQ ID NO:22.

As used herein, the term "Kr1(58-91 Active Zone w Val sub Cys)frag-Fc" fusion peptide complex corresponds to the 58-91 amino acid sequence of the Kr1(1-91 Active Zone) frag SEQ ID NO:19 in which three cysteine residues at the $69^{th}$, the $81^{st}$ and the $86^{th}$ amino acid positions are substituted with valine and which this substituted 58-91 amino acid sequence portion of the Kr1(1-91 Active Zone)frag SEQ ID NO:19 is bound to immunoglobulin via a peptide bond. This Kr1(58-91 Active Zone w Val sub Cys)frag-Fc fusion peptide complex is described in detail in SEQ ID NO:23.

As used herein, the term "Kr1(58-91 Active Zone w Ile sub Cys)frag-Fc" fusion peptide complex corresponds to the 58-91 amino acid sequence of the Kr1(1-91 Active Zone) frag SEQ ID NO: 19 in which three cysteine residues at the $69^{th}$, the $81^{st}$ and the $86^{th}$ amino acid positions are substituted with isoleucine and which this substituted 58-91 amino acid sequence portion of the Kr1(1-91 Active Zone)frag SEQ ID NO:19 is bound to immunoglobulin via a peptide bond. This Kr1(58-91 Active Zone w Ile sub Cys)frag-Fc fusion peptide complex is described in detail in SEQ ID NO:24.

As used herein, the term "Kr1(58-91 Active Zone w Leu sub Cys)frag-Fc" fusion peptide complex corresponds to the 58-91 amino acid sequence of the Kr1(1-91 Active Zone) frag SEQ ID NO:19 in which three cysteine residues at the $69^{th}$, the $81^{st}$ and the $86^{th}$ amino acid positions are substituted with leucine and which this substituted 58-91 amino acid sequence portion of the Kr1(1-91 Active Zone)frag SEQ ID NO:19 peptide is bound to immunoglobulin via a peptide bond. This Kr1(58-91 Active Zone w Leu sub Cys)frag-Fc fusion peptide complex is described in detail in SEQ ID NO:25.

As used herein, the term "Kr1(58-80 Active Zone)frag-Fc" fusion peptide complex correspond to the 58-80 amino acid sequence of the Kr1(1-91 Active Zone)frag SEQ ID NO: 19 in which this 58-80 amino acid sequence portion of the Kr1(1-91 Active Zone)frag SEQ ID NO: 19 peptide and which this 58-80 amino acid sequence portion of the Kr1 (1-91 Active Zone)frag SEQ ID NO: 19 bound to immunoglobulin via a peptide bond. This Kr1(58-80 Active Zone) frag-Fc fusion peptide complex is described in detail in SEQ ID NO:26.

As used herein, the term "Kr1(58-80 Active Zone w Ala sub Cys)frag-Fc" fusion peptide complex corresponds to the 58-80 amino acid sequence of the Kr1(1-91 Active Zone) frag SEQ ID NO:19 in which the cysteine residue at the $69^{th}$ amino acid position is substituted with alanine and this substituted 58-80 amino acid sequence portion of the Kr1 (1-91 Active Zone)frag SEQ ID NO:19 peptide is bound to immunoglobulin via a peptide bond. This Kr1(58-80 Active Zone w Ala sub Cys)frag-Fc fusion peptide complex is described in detail in SEQ ID NO:27.

As used herein, the term "Kr1(58-80 Active Zone w Val sub Cys)frag-Fc" fusion peptide complex corresponds to the 58-80 amino acid sequence of the Kr1(1-91 Active Zone) frag SEQ ID NO:19 in which the cysteine residue at the $69^{th}$ amino acid position is substituted with valine and this substituted 58-80 amino acid sequence portion of the Kr1 (1-91 Active Zone)frag SEQ ID NO: 19 peptide is bound to immunoglobulin via a peptide bond. This Kr1(58-80 Active Zone w Val sub Cys)frag-Fc fusion peptide complex is described in detail in SEQ ID NO:28.

As used herein, the term "Kr1(58-80 Active Zone w Ile sub Cys)frag-Fc" fusion peptide complex corresponds to the 58-80 amino acid sequence of the Kr1(1-91 Active Zone) frag SEQ ID NO: 19 which the cysteine residue at the $69^{th}$ amino acid position is substituted with isoleucine and this substituted 58-80 amino acid sequence portion of the Kr1 (1-91 Active Zone)frag SEQ ID NO: 19 peptide is bound to immunoglobulin via a peptide bond. This Kr1(58-80 Active Zone w Ile sub Cys)frag-Fc fusion peptide complex is described in detail in SEQ ID NO:29.

As used herein, the term "Kr1(58-80 Active Zone w Leu sub Cys)frag-Fc" fusion peptide complex corresponds to the 58-80 amino acid sequence of the Kr1(1-91 Active Zone) frag SEQ ID NO: 19 in which the cysteine residue at the $69^{th}$ amino acid position is substituted with leucine and this substituted 58-80 amino acid sequence portion of the Kr1 (1-91 Active Zone)frag SEQ ID NO:19 peptide is bound to immunoglobulin via a peptide bond. This Kr1(58-80 Active Zone w Leu sub Cys)frag-Fc fusion peptide complex is described in detail in SEQ ID NO:30.

As used herein, the term "Kr1(70-80 Active Zone)frag-Fc" refers to the fusion protein that correspond to the 70-80 amino acid sequence of the Kr1(1-91 Active Zone)frag SEQ ID NO: 19 in which this 70-80 amino acid sequence portion of the Kr1(1-91 Active Zone)frag SEQ ID NO:19 is bound to immunoglobulin via a peptide bond. This Kr1(70-80 Active Zone)frag-Fc fusion peptide complex is described in detail in SEQ ID NO:31.

As used herein, the term "Kr1(73-80 Active Zone)frag-Fc" refers to the fusion protein that correspond to the 73-80 amino acid sequence of the Kr1(1-91 Active Zone)frag SEQ ID NO: 19 and which this 73-80 amino acid sequence portion of the Kr1(1-91 Active Zone)frag SEQ ID NO:19 peptide is bound to immunoglobulin via a peptide bond. This Kr1(73-80 Active Zone)frag-Fc fusion peptide complex is described in detail in SEQ ID NO:32.

Some preferred ROR2 kringle fragments from the second receptor tyrosine kinase-like orphan receptor (ROR2) conjugated to immunoglobulin (i.e., the Kr2-frag-Fc fusion peptide complexes) include but not limited to the peptide sequences selected from the group consisting of SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

As used herein, the term "Kr2(1-85 Active Zone)frag-Fc" fusion peptide complex corresponds to the 1-85 amino acid sequence of the of the Kr2(1-85 Active Zone)frag" SEQ ID NO:33 peptide bound to immunoglobulin via a peptide bond. This Kr2(1-85 Active Zone)frag-Fc fusion peptide complex is described in detail in SEQ ID NO:34.

As used herein, the term "Kr2(56-85 Active Zone)frag-Fc" fusion peptide complex corresponds to the 56-85 amino acid sequence of the Kr2(1-85 Active Zone)frag" SEQ ID NO:33 and which this 56-85 amino acid sequence portion of the Kr2(1-85 Active Zone)frag" SEQ ID NO:33 peptide is bound to immunoglobulin via a peptide bond. This Kr2(56-85 Active Zone)frag-Fc fusion peptide complex is described in detail in SEQ ID NO:35.

As used herein, the term "Kr2(56-85 Active Zone w Ala sub Cys)frag-Fc" fusion peptide complex corresponds to the 56-85 amino acid sequence of the Kr2(1-85 Active Zone) frag" SEQ ID NO:33 in which three cysteine residues at the $67^{th}$, the $79^{th}$ and the $84^{th}$ amino acid positions are substituted with alanine and which this substituted 56-85 amino acid sequence portion of the Kr2(1-85 Active Zone)frag" SEQ ID NO:33 peptide is bound to immunoglobulin via a peptide bond. This Kr2(56-85 Active Zone w Ala sub Cys)frag-Fc fusion peptide complex is described in detail in SEQ ID NO:36.

As used herein, the term "Kr2(56-85 Active Zone w Val sub Cys)frag-Fc" fusion peptide complex corresponds to the 56-85 amino acid sequence of the Kr2(1-85 Active Zone) frag" SEQ ID NO:33 in which three cysteine residues at the $67^{th}$, the $79^{th}$ and the $84^{th}$ amino acid positions are substituted with valine and which this substituted 56-85 amino acid sequence portion of the Kr2(1-85 Active Zone)frag" SEQ ID NO:33 peptide is bound to immunoglobulin via a peptide bond. This Kr2(56-85 Active Zone w Val sub Cys)frag-Fc fusion peptide complex is described in detail in SEQ ID NO:37.

As used herein, the term "Kr2(56-85 Active Zone w Ile sub Cys)frag-Fc" fusion peptide complex corresponds to the 56-85 amino acid sequence of the Kr2(1-85 Active Zone) frag" SEQ ID NO:33 in which three cysteine residues at the $67^{th}$, the $79^{th}$ and the $84^{th}$ amino acid positions are substituted with isoleucine and which this substituted 56-85 amino acid sequence portion of the Kr2(1-85 Active Zone)frag" SEQ ID NO:33 peptide is bound to immunoglobulin via a peptide bond. This Kr2(56-85 Active Zone w Ile sub Cys) frag-Fc fusion peptide complex is described in detail in SEQ ID NO:38.

As used herein, the term "Kr2(56-85 Active Zone w Leu sub Cys)frag-Fc" fusion peptide complex corresponds to the 56-85 amino acid sequence of the Kr2(1-85 Active Zone) frag" SEQ ID NO:33 in which three cysteine residues at the $67^{th}$, the $79^{th}$ and the $84^{th}$ amino acid positions are substituted with leucine and which this substituted 56-85 amino acid sequence portion of the Kr2(1-85 Active Zone)frag" SEQ ID NO:33 peptide is bound to immunoglobulin via a peptide bond. This Kr2(56-85 Active Zone w Leu sub Cys)frag-Fc fusion peptide complex is described in detail in SEQ ID NO:39.

As used herein, the term "Kr2(68-85 Active Zone)frag-Fc" fusion peptide complex corresponds to the 68-85 amino acid sequence of the Kr2(1-85 Active Zone)frag" SEQ ID NO:33 and which this 68-85 amino acid sequence portion of the Kr2(1-85 Active Zone)frag" SEQ ID NO:33 peptide is bound to immunoglobulin via a peptide bond. This Kr2(68-85 Active Zone)frag-Fc fusion peptide complex is described in detail in SEQ ID NO:40.

As used herein, the term "Kr2(68-85 Active Zone w Ala sub Cys)frag-Fc" fusion peptide complex corresponds to the 68-85 amino acid sequence of the Kr2(1-85 Active Zone) frag" SEQ ID NO:33 in which the cysteine residue at the $79^{th}$ and $84^{th}$ amino acid position is substituted with alanine and which this substituted 68-85 amino acid sequence portion of the Kr2(1-85 Active Zone)frag" SEQ ID NO:33 peptide is bound to immunoglobulin via a peptide bond. This Kr2(68-85 Active Zone w Ala sub Cys)frag-Fc fusion peptide complex is described in detail in SEQ ID NO:41.

As used herein, the term "Kr2(68-85 Active Zone w Val sub Cys)frag-Fc" fusion peptide complex corresponds to the 68-85 amino acid sequence of the Kr2(1-85 Active Zone) frag" SEQ ID NO:33 in which the cysteine residue at the $79^{th}$ and $84^{th}$ amino acid position is substituted with valine and which this substituted 68-85 amino acid sequence portion of the Kr2(1-85 Active Zone)frag" SEQ ID NO:33 peptide is bound to immunoglobulin via a peptide bond. This Kr2(68-85 Active Zone w Val sub Cys)frag-Fc fusion peptide complex is described in detail in SEQ ID NO:42.

As used herein, the term "Kr2(68-85 Active Zone w Ile sub Cys)frag-Fc" fusion peptide complex corresponds to the 68-85 amino acid sequence of the Kr2(1-85 Active Zone) frag" SEQ ID NO:33 in which the cysteine residue at the $79^{th}$ and $84^{th}$ amino acid position is substituted with isoleucine and which this substituted 68-85 amino acid sequence portion of the Kr2(1-85 Active Zone)frag" SEQ ID NO:33 peptide is bound to immunoglobulin via a peptide bond. This Kr2(68-85 Active Zone w Ile sub Cys)frag-Fc fusion peptide complex is described in detail in SEQ ID NO:43.

As used herein, the term "Kr2(68-85 Active Zone w Leu sub Cys)frag-Fc" fusion peptide complex corresponds to the 68-85 amino acid sequence of the Kr2(1-85 Active Zone) frag" SEQ ID NO:33 in which the cysteine residue at the $79^{th}$ and $84^{th}$ amino acid position is substituted with leucine and which this substituted 68-85 amino acid sequence portion of the Kr2(1-85 Active Zone)frag" SEQ ID NO:33 peptide is bound to immunoglobulin via a peptide bond. This Kr2(68-85 Active Zone w Leu sub Cys)frag-Fc fusion peptide complex is described in detail in SEQ ID NO:44.

As used herein, the term "Kr2(68-79 Active Zone)frag-Fc" fusion peptide complex corresponds to the 68-79 amino acid sequence of the Kr2(1-85 Active Zone)frag" SEQ ID NO:33 and which this 68-79 amino acid sequence portion of the Kr2(1-85 Active Zone)frag" SEQ ID NO:33 peptide is bound to immunoglobulin via a peptide bond. This Kr2(68-79 Active Zone)frag-Fc fusion peptide complex is described in detail in SEQ ID NO:45.

Kr1 Fragment Peptides

Some of the preferred modified active zone peptide fragments of Kr1 herein abbreviated as Kr1-frag peptides include but not limited to the peptide sequences selected from the group consisting of SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61.

As used herein, the term "Kr1(1-93 Active Zone)frag" peptide fragment refers to the 1-93 amino acid sequence fragment of the corresponding Kr1(1-93 Active Zone)frag peptide described in SEQ ID NO: 19.

As used herein, one of the Kr1-frag peptides is "Kr1(58-81 Active Zone w Ala sub Cys and w Lys sub Cys)frag" peptide that corresponds to the 58-81 amino acid sequence of the Kr1(1-91 Active Zone)frag SEQ ID NO: 19 where the cysteine residue at the $69^{th}$ amino acid position of the corresponding Kr1(1-91 Active Zone)frag SEQ ID NO:19 is substituted with alanine and in which the cysteine residue at the $81^{st}$ amino acid position of the corresponding Kr1(1-91 Active Zone)frag SEQ ID NO:19 is substituted with lysine. This Kr1(58-81 Active Zone w Ala sub Cys and w Lys sub Cys)frag peptide is described in SEQ ID NO:46.

As used herein, another Kr1-frag peptide is the "Kr1(58-81 Active Zone w Val sub Cys and w Lys sub Cys)frag" peptide that corresponds to the 58-81 amino acid sequence of the Kr1(1-91 Active Zone)frag SEQ ID NO: 19 where the cysteine residue at the $69^{th}$ amino acid position of the corresponding Kr1(1-91 Active Zone)frag SEQ ID NO:19 is substituted with valine and in which the cysteine residue at the $81^{st}$ amino acid position of the corresponding Kr1(1-91 Active Zone)frag SEQ ID NO:19 is substituted with lysine. This Kr1(58-81 Active Zone w Val sub Cys and w Lys sub Cys)frag peptide is described in SEQ ID NO:47.

As used herein, yet another Kr1-frag peptide is the "Kr1(58-81 Active Zone w Ile sub Cys and w Lys sub Cys)frag" peptide that corresponds to the 58-81 amino acid sequence of the Kr1(1-91 Active Zone)frag SEQ ID NO: 19 where the cysteine residue at the $69^{th}$ amino acid position of the corresponding Kr1(1-91 Active Zone)frag SEQ ID NO:19 is substituted with isoleucine and in which the cysteine residue at the $81^{st}$ amino acid position of the corresponding Kr1(1-91 Active Zone)frag SEQ ID NO:19 is substituted with lysine. This Kr1(58-81 Active Zone w Ile sub Cys and w Lys sub Cys)frag peptide is described in SEQ ID NO:48.

As used herein, another Kr1-frag peptide is the "Kr1(58-81 Active Zone w Leu sub Cys and w Lys sub Cys)frag" peptide that corresponds to the 58-81 amino acid sequence of the Kr1(1-91 Active Zone)frag SEQ ID NO: 19 where the cysteine residue at the $69^{th}$ amino acid position of the corresponding Kr1(1-91 Active Zone)frag SEQ ID NO:19 is substituted with leucine and in which the cysteine residue at the $81^{st}$ amino acid position of the corresponding Kr1(1-91 Active Zone)frag SEQ ID NO:19 is substituted with lysine. This Kr1(58-81 Active Zone w Leu sub Cys and w Lys sub Cys)frag peptide is described in detail in SEQ ID NO:49.

As used herein, another Kr1-frag peptide is the "Kr1(58-80 Active Zone w Ala sub Cys)frag" peptide that corresponds refers to the 58-80 amino acid sequence of the Kr1(1-91 Active Zone)frag SEQ ID NO: 19 where cysteine residue at the $69^{th}$ amino acid position of Kr1(1-91 Active Zone)frag SEQ ID NO:19 is substituted with alanine. This Kr1(58-80 Active Zone w Ala sub Cys)frag is described in SEQ ID NO:50.

As used herein, another Kr1-frag peptide is the "Kr1(58-80 Active Zone w Val sub Cys)frag" peptide that corresponds refers to the 58-80 amino acid sequence of the Kr1(1-91 Active Zone)frag SEQ ID NO: 19 where the cysteine residue at the $69^{th}$ amino acid position of Kr1(1-91 Active Zone)frag SEQ ID NO:19 is substituted with valine. This Kr1(58-80 Active Zone w Val sub Cys)frag peptide is described in detail in SEQ ID NO:51.

As used herein, another Kr1-frag peptide is the "Kr1(58-80 Active Zone w Ile sub Cys)frag" peptide corresponds that refers to the 58-80 amino acid sequence of the Kr1(1-91 Active Zone)frag SEQ ID NO:19 where the cysteine residue at the $69^{th}$ amino acid position of Kr1(1-91 Active Zone)frag SEQ ID NO: 19 is substituted with isoleucine. This Kr1(58-80 Active Zone w Ile sub Cys)frag peptide is described in SEQ ID NO:52.

As used herein, another Kr1-frag peptide is the "Kr1(58-80 Active Zone w Leu sub Cys)frag" peptide that corresponds refers to the 58-80 amino acid sequence of the Kr1(1-91 Active Zone)frag SEQ ID NO: 19 where the cysteine residue at the $69^{th}$ amino acid position of Kr1(1-91 Active Zone)frag SEQ ID NO:19 is substituted with leucine. This Kr1(58-80 Active Zone w Leu sub Cys)frag peptide is described in SEQ ID NO:53.

As used herein, another Kr1-frag peptide is the "Kr1(58-69 Active Zone w Lys sub Cys)frag" peptide that corresponds to the 58-69 amino acid sequence fragment of the corresponding Kr1(1-91 Active Zone)frag SEQ ID NO: 19 where the cysteine residue at the $69^{th}$ amino acid position of Kr1(1-91 Active Zone)frag SEQ ID NO:19 is substituted with lysine. This Kr1(58-69 Active Zone w Lys sub Cys)frag is peptide described in SEQ ID NO:54.

As used herein, another Kr1-frag peptide is the "Kr1(58-68 Active Zone)frag" peptide fragment that corresponds to the 58-68 amino acid sequence fragment of the Kr1(1-91 Active Zone)frag SEQ ID NO:19. This Kr1(58-68 Active Zone)frag peptide is described in detail in SEQ ID NO:55.

As used herein, another Kr1-frag peptide is the "Kr1(70-81 Active Zone w Lys sub Cys)frag" peptide that corresponds to the 70-81 amino acid sequence fragment of the corresponding Kr1(1-91 Active Zone)frag SEQ ID NO:19 where the cysteine residue at the $81^{St}$ amino acid position of Kr1(1-91 Active Zone)frag SEQ ID NO:19 is substituted with lysine. This Kr1(70-81 Active Zone w Lys sub Cys)frag peptide which is described in detail in SEQ ID NO:56.

As used herein, another Kr1-frag peptide is the "Kr1(70-80 Active Zone)frag" peptide fragment that corresponds to the 70-80 amino acid sequence fragment of Kr1(1-91 Active Zone)frag SEQ ID NO:19. This Kr1(70-80 Active Zone)frag peptide is described in detail in SEQ ID NO:57.

As used herein, another Kr1-frag peptide is the "Kr1(71-80 Active Zone)frag" peptide fragment that corresponds to the 71-80 amino acid sequence fragment of Kr1(1-91 Active Zone)frag SEQ ID NO:19. This Kr1(71-80 Active Zone)frag peptide is described in detail in SEQ ID NO:58.

As used herein, another Kr1-frag peptide is the peptide fragment that corresponds to the 72-80 amino acid sequence fragment of Kr1(1-91 Active Zone)frag SEQ ID NO: 19. This peptide fragment is described in detail in SEQ ID NO:59.

As used herein, another Kr1-frag peptide is the "Kr1(73-80 Active Zone)frag" peptide fragment that corresponds to the 73-80 amino acid sequence fragment of the corresponding Kr1(1-91 Active Zone)frag SEQ ID NO:19. This Kr1(73-80 Active Zone)frag peptide is described in detail in SEQ ID NO:60.

As used herein, another Kr1-frag peptide is the "Kr1(73-79 Active Zone)frag" peptide fragment that corresponds to the 73-79 amino acid sequence fragment of Kr1(1-91 Active Zone)frag SEQ ID NO:19. This Kr1(73-79 Active Zone)frag peptide is described in detail in SEQ ID NO:61.

Modified ROR1 Kringle Fragment (Mod-Kr1-Frag) Peptides

Modified ROR1 kringle fragment (abbreviated as mod-Kr1-frag) peptides to various reactive linking groups are believed to realize considerably longer in vivo bioactive half-lifes as compared to the non-modified ROR1 kringle fragment (abbreviated as Kr1-frag) peptides. It is believed that some of these linking groups that attached to the various ROR1 kringle fragment peptides may result in forming stable conjugates with blood peptides and tissues when introduced in vivo into the patient. Some preferred modified ROR1 kringle fragments peptides include but not limited to acetyl groups linked to the α-N terminus of the Kr1-frag peptides, MPA linking groups attached to the α-N terminus of the Kr1-frag peptides, MPA-AEEA linking groups attached to the α-N terminus of the Kr1-frag peptides, and MPA linking groups attached to the N-epsilon to the α-C terminus of lysine of the Kr1-frag peptides.

Preferred NAc modified Kr1 fragment peptides include but not limited to the peptide sequences selected from the group consisting of: SEQ ID NO:78; SEQ ID NO:79; SEQ ID NO:80; SEQ ID NO:81; SEQ ID NO:90; SEQ ID NO:91; SEQ ID NO:92; SEQ ID NO:93; SEQ ID NO:94; SEQ ID NO:95; SEQ ID NO:96; SEQ ID NO:97; SEQ ID NO:106; SEQ ID NO:109; SEQ ID NO:110; SEQ ID NO:113; SEQ ID NO:116; SEQ ID NO:117; SEQ ID NO:120; SEQ ID NO:123; SEQ ID NO:126; SEQ ID NO:129; and SEQ ID NO:186.

Preferred MPA-Kr1 α-N terminus modified peptide fragments include but not limited to the peptide sequences selected from the group consisting of: SEQ ID NO:82; SEQ ID NO:83; SEQ ID NO:84; SEQ ID NO:85; SEQ ID NO:98; SEQ ID NO:99; SEQ ID NO:100; SEQ ID NO:101; SEQ ID NO:107; SEQ ID NO:111; SEQ ID NO:114; SEQ ID NO:118; SEQ ID NO:121; SEQ ID NO:124; SEQ ID NO:127; SEQ ID NO:130; and SEQ ID NO:187.

Preferred MPA-AEEA-Kr1 α-N terminus modified peptide fragments include but not limited to the peptide sequences selected from the group consisting of: SEQ ID NO:86; SEQ ID NO:87; SEQ ID NO:88; SEQ ID NO:89; SEQ ID NO:102; SEQ ID NO:103; SEQ ID NO:104; SEQ ID NO:105; SEQ ID NO:108; SEQ ID NO:112; SEQ ID NO:115; SEQ ID NO:119; SEQ ID NO:122; SEQ ID NO:125; SEQ ID NO:128; SEQ ID NO:131; and SEQ ID NO:188.

Preferred N-epsilon MPA-Kr1 α-C terminus N modified peptide fragments include but not limited to the peptide sequences selected from the group consisting of: SEQ ID NO:90; SEQ ID NO:91; SEQ ID NO:92; SEQ ID NO:93; SEQ ID NO:109; and SEQ ID NO:116.

ROR2 Kringle Fragment Peptides

Preferred ROR2 kringle fragment (K2-frag) peptides of the invention include but not limited to the peptide sequences selected from the group consisting of: SEQ ID NO:62; SEQ ID NO:63; SEQ ID NO:64; SEQ ID NO:65; SEQ ID NO:66; SEQ ID NO:67; SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; and SEQ ID NO:77.

As used herein, the term "Kr2(6-84 Active Zone)frag" peptide refers to the 6-84 amino acid sequence fragment of the corresponding Kr2(1-85 Active Zone)frag" SEQ ID NO:33. This Kr2(6-84 Active Zone)frag peptide is described in detail in SEQ ID NO:62.

As used herein, the term "Kr2(56-79 Active Zone w Ala sub Cys and w Lys sub Cys)frag" peptide refers to the 56-79 amino acid sequence fragment of the Kr2(1-85 Active Zone)frag" SEQ ID NO:33 where the cysteine residue at the 67$^{th}$ amino acid of the Kr2(1-85 Active Zone)frag" SEQ ID NO:33 has been substituted with alanine and where the cysteine residue at the 79' amino acid position of the Kr2(1-85 Active Zone)frag" SEQ ID NO:33 peptide has been substituted with lysine. This Kr2(56-79 Active Zone w Ala sub Cys and w Lys sub Cys)frag peptide is described in SEQ ID NO:63.

As used herein, the term "Kr2(56-79 Active Zone w Val sub Cys and w Lys sub Cys)frag" peptide refers to the 56-79 amino acid sequence fragment of the Kr2(1-85 Active Zone)frag" SEQ ID NO:33 where the cysteine residue at the 67$^{th}$ amino acid of the Kr2(1-85 Active Zone)frag" SEQ ID NO:33 has been substituted with valine and where the cysteine residue at the 79$^{th}$ amino acid position of the Kr2(1-85 Active Zone)frag" SEQ ID NO:33 peptide has been substituted with lysine. This Kr2(56-79 Active Zone w Val sub Cys and w Lys sub Cys)frag peptide is described in SEQ ID NO:64.

As used herein, the term "Kr2(56-79 Active Zone w Ile sub Cys and w Lys sub Cys)frag" peptide refers to the 56-79 amino acid sequence fragment of the Kr2(1-85 Active Zone)frag" SEQ ID NO:33 where the cysteine residue at the 67$^{th}$ amino acid of the Kr2(1-85 Active Zone)frag" SEQ ID NO:33 has been substituted with isoleucine and where the cysteine residue at the 79" amino acid position of Kr2(1-85 Active Zone)frag" SEQ ID NO:33 peptide has been substituted with lysine. This Kr2(56-79 Active Zone w Ile sub Cys and w Lys sub Cys)frag peptide is described in SEQ ID NO:65.

As used herein, the term "Kr2(56-79 Active Zone w Leu sub Cys and w Lys sub Cys)frag" peptide refers to the 56-79 amino acid sequence fragment of the Kr2(1-85 Active Zone)frag" SEQ ID NO:33 where the cysteine residue at the 67$^{th}$ amino acid of the Kr2(1-85 Active Zone)frag" SEQ ID NO:33 has been substituted with leucine and where the cysteine residue at the 79' amino acid position of the Kr2 (1-85 Active Zone)frag peptide has been substituted with lysine. This Kr2(56-79 Active Zone w Leu sub Cys and w Lys sub Cys)frag peptide is described in SEQ ID NO:66.

As used herein, the term "Kr2(56-78 Active Zone w Ala sub Cys)frag" peptide refers to the 56-78 amino acid sequence fragment of the Kr2(1-85 Active Zone)frag" SEQ ID NO:33 in which the cysteine residue at the 67$^{th}$ amino acid of the Kr2(1-85 Active Zone)frag" SEQ ID NO:33 has been substituted with alanine. This Kr2(56-78 Active Zone w Ala sub Cys)frag peptide is described in SEQ ID NO:67.

As used herein, the term "Kr2(56-78 Active Zone w Val sub Cys)frag" peptide refers to the 56-78 amino acid sequence fragment of the Kr2(1-85 Active Zone)frag" SEQ ID NO:33 in which the cysteine residue at the 67$^{th}$ amino acid of the Kr2(1-85 Active Zone)frag" SEQ ID NO:33 has been substituted with valine. This Kr2(56-78 Active Zone w Val sub Cys)fragpeptide is described in SEQ ID NO:68.

As used herein, the term "Kr2(56-78 Active Zone w Ile sub Cys)frag" peptide refers to the 56-78 amino acid sequence fragment of the Kr2(1-85 Active Zone)frag" SEQ ID NO:33 in which the cysteine residue at the 67$^{th}$ amino acid of the Kr2(1-85 Active Zone)frag" SEQ ID NO:33 has been substituted with isoleucine. This Kr2(56-78 Active Zone w Ile sub Cys)frag peptide is described in SEQ ID NO:69.

As used herein, the term "Kr2(56-78 Active Zone w Leu sub Cys)frag" peptide refers to the 56-78 amino acid sequence fragment of the Kr2(1-85 Active Zone)frag" SEQ ID NO:33 in which the cysteine residue at the 67$^{th}$ amino acid of the Kr2(1-85 Active Zone)frag" SEQ ID NO:33 has been substituted with leucine. This Kr2(56-78 Active Zone w Leu sub Cys)frag peptide is described in SEQ ID NO:70.

As used herein, the term "Kr2(56-67 Active Zone w Lys sub Cys)frag" peptide refers to the 56-67 amino acid sequence fragment of the Kr2(1-85 Active Zone)frag" SEQ ID NO:33 in which the cysteine residue at the 67$^{th}$ amino acid of the Kr2(1-85 Active Zone)frag" SEQ ID NO:33 has been substituted with lysine. This Kr2(56-67 Active Zone w Lys sub Cys)frag peptide is described in SEQ ID NO:71.

As used herein, the term "Kr2(56-66 Active Zone)frag" peptide fragment refers to the 56-66 amino acid sequence fragment of the Kr2(1-85 Active Zone)frag" SEQ ID NO:33. This Kr2(56-66 Active Zone)frag peptide fragment is described in detail in SEQ ID NO:72.

As used herein, the term "Kr2(68-79 Active Zone w Lys sub Cys)frag" peptide refers to the 68-79 amino acid sequence fragment of the Kr2(1-85 Active Zone)frag" SEQ ID NO:33 in which the cysteine residue at the 79$^{th}$ amino acid of the Kr2(1-85 Active Zone)frag" SEQ ID NO:33 has been substituted with lysine. This Kr2(68-79 Active Zone w Lys sub Cys)frag peptide is described in SEQ ID NO:73.

As used herein, the term "Kr2(68-78 Active Zone)frag" peptide fragment refers to the 68-78 amino acid sequence fragment of the Kr2(1-85 Active Zone)frag" SEQ ID NO:33. This Kr2(68-78 Active Zone)frag peptide is described in detail in SEQ ID NO:74.

As used herein, the term "Kr2(69-78 Active Zone)frag" peptide fragment refers to the 69-78 amino acid sequence fragment of the Kr2(1-85 Active Zone)frag" SEQ ID NO:33. This Kr2(69-78 Active Zone)frag peptide is described in detail in SEQ ID NO:75.

As used herein, the term "Kr2(70-78 Active Zone)frag" peptide fragment refers to the 70-78 amino acid sequence fragment of the Kr2(1-85 Active Zone)frag" SEQ ID NO:33. This Kr2(70-78 Active Zone)frag peptide is described in detail in SEQ ID NO:76.

As used herein, the term "Kr2(70-77 Active Zone)frag" peptide fragment refers to the 70-77 amino acid sequence fragment of the Kr2(1-85 Active Zone)frag" SEQ ID NO:33. This Kr2(70-77 Active Zone)frag peptide is described in detail in SEQ ID NO:77.

Modified ROR2 Kringle Fragment (Mod-Kr2-Frag) Peptides

Modified ROR2 kringle fragment (abbreviated as mod-Kr2-frag) peptides to various reactive linking groups are believed to realize considerably longer in vivo bioactive half-lifes as compared to the non-modified ROR2 kringle fragment (abbreviated as Kr2-frag) peptides. It is believed that some of these linking groups that attached to the various ROR2 kringle fragment peptides may result in forming stable conjugates with blood peptides and tissues when introduced in vivo into the patient. Some preferred modified ROR2 kringle fragments peptides include but not limited to acetyl groups linked to the α-N terminus of the Kr2-frag peptides, MPA linking groups attached to the α-N terminus of the Kr2-frag peptides, MPA-AEEA linking groups attached to the α-N terminus of the Kr2-frag peptides, and MPA linking groups attached to the N-epsilon to the α-C terminus of lysine of the Kr2-frag peptides.

Preferred NAc Kr2 α-N terminus modified peptide fragments include but not limited to the peptide sequences selected from the group consisting of: SEQ ID NO:132; SEQ ID NO:135; SEQ ID NO:136; SEQ ID NO:137; SEQ ID NO:138; SEQ ID NO:147; SEQ ID NO:148; SEQ ID NO:149; SEQ ID NO:150; SEQ ID NO:151; SEQ ID NO:152; SEQ ID NO:153; SEQ ID NO:154; SEQ ID NO:163; SEQ ID NO:166; SEQ ID NO:167; SEQ ID NO:170; SEQ ID NO:174; SEQ ID NO:177; SEQ ID NO:180; and SEQ ID NO:183.

Preferred MPA-Kr2 α-N terminus modified peptide fragments of the invention include but not limited to the peptide sequences selected from the group consisting of: SEQ ID NO:133; SEQ ID NO:139; SEQ ID NO:140; SEQ ID NO:141; SEQ ID NO:142; SEQ ID NO:155; SEQ ID NO:156; SEQ ID NO:157; SEQ ID NO:158; SEQ ID NO:164; SEQ ID NO:168; SEQ ID NO:171; SEQ ID NO:175; SEQ ID NO:178; SEQ ID NO:181; and SEQ ID NO:184.

Preferred MPA-AEEA-Kr1 α-N terminus modified peptide fragments of the invention include but not limited to the peptide sequences selected from the group consisting of: SEQ ID NO:134; SEQ ID NO:143; SEQ ID NO:144; SEQ ID NO:145; SEQ ID NO:146; SEQ ID NO:159; SEQ ID NO:160; SEQ ID NO:161; SEQ ID NO:162; SEQ ID NO:165; SEQ ID NO:169; SEQ ID NO:172; SEQ ID NO:176; SEQ ID NO:179; SEQ ID NO:182; and SEQ ID NO:185.

Preferred N-epsilon MPA-Kr2 α-C terminus N modified peptide fragments of the invention include but not limited to the peptide sequences selected from the group consisting of: SEQ ID NO: 147; SEQ ID NO:166; and SEQ ID NO:173.

Thus, it is to be understood that the present invention is contemplated to encompass any kringle peptide fragments, any modified kringle peptide fragments, and any kringle fragment fusion peptides which have antiangiogenic activity and includes the entire class of kringle fragment peptides and fusion peptides described herein and homologues or analogues of those fragments and peptides. Additionally, the invention is not dependent on the manner in which the kringle peptide fragment or fusion protein is produced, e.g., by (1) proteolytic cleavage of an isolated mammalian plasminogen or ROR, (2) by expression of a recombinant molecule having a polynucleotide which encodes the amino acid sequence of a kringle 5 peptide fragment or fusion protein and (3) solid phase synthetic techniques known to those of ordinary skill in the art.

Kringle peptide fragments (e.g., the ROR1 or ROR2 peptide fragments), and/or the kringle fusion peptides (e.g., the kringle 5 plasminogen, the ROR1 kringle or the ROR2 kringle fusions peptides) may also be made by any number of well known synthesis procedures. A preferred synthesis protocol is that which employs solid phase chemistry known to those of ordinary skill in the art. For example, the kringle peptide fragments or kringle fusion peptides may be synthesized by solid phase chemistry techniques following the well known procedures using an Applied Biosystem synthesizer. Alternately multiple fragments may be separately synthesized and then later linked together to form the larger fragments or final fusion protein. These synthetic peptide fragments or fusion peptides can also be made with amino acid substitutions at specific locations to evaluate for anti-angiogenesis activity in vitro and in vivo. For classical solution synthesis these methods comprise the sequential addition of one or more amino acids or suitably protected amino acids to a growing peptide chain. Usually, either the amino or carboxyl group of the first amino acid is protected by a suitable protecting group. The protected or modified amino acids are then either attached to an solid phase support or used in solution by adding the next amino acid in the sequence having the complimentary (amino or carboxyl) group which is suitably protected for forming the amide linkages. Afterwards the protecting groups are then removed from this growing amino acid residue and then the next sequential and suitably protected amino acid is added, and so forth. Upon completion of sequentially linked together all the amino acids in the proper sequence, any remaining protecting groups (and any solid support) may then be removed to free up the final desired polypeptide. It is also possible to add more than one amino acid at a time to a growing peptide chain, for example, by coupling together a protected tripeptide with a properly protected dipeptide to form, after deprotection, a pentapeptide.

In preparing compounds of the present invention a particularly preferred method involves solid phase peptide synthesis in which the α-N-terminal of the amino acid is protected by an acid or base sensitive group. Desirable chemical properties of any of the protection groups is that they are relatively stable to the conditions of peptide linkage formation while being readily removable without destroying the growing peptide chain and/or destroying the racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and analogous derivatives. A most preferred protection group is the 9-fluorenyl-methyloxycarbonyl (Fmoc) protection group for use in the synthesis of kringle fusion peptides and/or kringle peptide fragments. Preferred side chain protection groups for protecting side chain amino groups in lysine and arginine are 2,2,5,7,8-pentamethylchroman-6-sulfonyl (pmc), nitro, p-toluenesulfonyl, 4-methoxybenzene-sulfonyl, benzyloxycarbonyl (Cbz), t-butyloxycarbonyl (Boc), and adamantyloxycarbonyl. Preferred side chain protection groups for protecting side chain amino groups for tyrosine include benzyl, o-bromobenzyloxy-carbonyl, 2,6-dichlorobenzyl, isopropyl, t-butyl (t-Bu), cyclohexyl, cyclopenyl and acetyl (Ac) groups. Preferred side chain protection groups for protecting side chain amino groups for serine include t-butyl, benzyl and tetrahydropyranyl groups. Preferred side chain protection groups for protecting side chain amino groups for histidine include trityl, benzyl, Cbz, p-toluenesulfonyl and 2,4-dinitrophenyl groups. Preferred side chain protection groups for protecting side chain amino groups for tryptophan include, formyl groups. Preferred side chain protection groups for protecting side chain amino groups for aspartic acid and glutamic acid include benzyl and t-butyl groups. Preferred side chain protection groups for protecting side chain amino groups for cysteine include triphenylmethyl (trityl) groups.

In the preferred solid phase peptide synthesis methodology, the α-C-terminal amino acid is attached to a solid phase support. Preferable properties of suitable solid phase supports are that these materials are inert to the reagents and inert to the reaction conditions of the stepwise condensation-deprotection reactions, as well as being insoluble in the media used. A preferred solid phase support for α-C-terminal carboxy peptides synthesis is 4-hydroxymethylphenoxymethyl-copoly(styrene-1% divinylbenzene). In particular, 4-(2',4'-dimethoxyphenyl-Fmoc-aminomethyl) phenoxyacetamidoethyl resin is a preferred solid support for synthesizing α-C-terminal amide peptides in which the α-C-terminal amino acid is coupled to the resin by N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP) or bis(2-oxo-3-oxazolidinyl)phosphine chloride (BOPCl), in which mediated coupling is performed for from about 1 to 24 hours at a temperature of between about 10° C. to 50° C. in a solvent such as dimethylformamide (DMF) or dichloromethane. When the solid phase support is 4-(2',4'-dimethoxyphenyl-Fmoc-aminomethyl)phenoxy-acetamidoethyl resin (available from Applied Biosystems, Foster City, Calif.), the Fmoc group is cleaved with a secondary amine, such as piperidine, prior to coupling with the α-C-terminal amino acid as described above. The preferred method for coupling to the deprotected 4-(2',4'-dimethoxyphenyl-Fmoc-aminomethyl) phenoxy-acetamidoethyl resin is using about one equivalent of O-benzotriazol-1-yl-N,N,N',N'-tetramethyluroniumhexafluorophosphate (HBTU) and about one equivalent 1-hydroxybenzotriazole (HOBT) in DMF. The coupling of successive protected amino acids is preferred to be performed using an automatic polypeptide synthesizer. As noted above one preferred embodiment is protecting the α-N-terminal in the amino acids of the growing peptide chain with Fmoc. Also as noted above, removal of the Fmoc protection group from the α-N-terminal side of the growing peptide is accomplished with a secondary amine, preferably piperidine. It is preferable that about a three-fold excess of each protected amino acid is added to the growing polypeptide sequence in which the coupling is preferably carried out in DMF. The coupling agent is preferably one equivalence of O-benzotriazol-1-yl-N,N,N',N'-tetramethyluroniumhexafluorophosphate (HBTU) and one equivalence of 1-hydroxybenzotriazole (HOBT). At the completion of the solid phase polypeptide synthesis, the polypeptide is removed from the resin and deprotected, either in successively or in a single operational step. Removal of the polypeptide and deprotection can be accomplished in a single operation by treating the resin-bound polypeptide with a cleavage reagent that comprises of thioanisole; water; 1,2 ethanedithiol (EDT); and trifluoroacetic acid (TFA). In cases in which the α-C-terminal of the polypeptide is an alkylamide, the polypeptide can be cleaved from the solid state resin by aminolysis with an alkylamine. Alternatively, the polypeptide can be removed by transesterification, e.g. with methanol, followed by aminolysis or by direct transamidation. The protected polypeptide may be purified at this point or taken to the next step directly. The removal of the side chain protecting groups performed using the cleavage cocktail as described above. The fully deprotected polypeptide is preferably purified and isolated any number of chromatographic separations which can include: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing. Solid phase synthesis of some representative kringle peptide fragments and kringle fusion peptides is illustrated in the below Examples.

Depending on how the particular synthesized kringle fusion protein may exist with or without the aforementioned disulfide bonds of the kringle region forming a tertiary structure which differs from the tertiary structure found in the corresponding naturally occurring native kringle region. Kringle peptide fragments produced by enzymatic cleavage of Glu-, Lys- or miniplasminogen with elastase and/or pepsin (enzymes which cleave at sites removed from the cysteine linkages) are believed to exhibit the native tertiary kringle protein structure. Kringle peptide fragments prepared by solid phase peptide synthesis may or may not contain corresponding cystyl amino acyl residues. Alternately kringle peptide fragments prepared by expression may contain disulfide bonds at different positions than those found in native corresponding kringle peptide fragments produced by enzymatic cleavage.

It is understood that any of these kringle fusion peptides (i.e., immunoglobulin derivatives coupled to the kringle 5 plasminogen fragments, to the ROR1 kringle fragments and to the ROR2 kringle fragments peptides), the kringle fragment peptides (the ROR1 or ROR2 kringle fragment peptides) and the modified kringle fragment peptides (mod-Kr1-frag and mod-Kr2-frag) of this invention, including but not limited to those specified in the examples, possess anti-angiogenic activity. As such it is believed that these compounds of the invention are useful in the treatment of both primary and metastatic solid tumors and carcinomas of the brain; bile ducts; bladder; breast; colon; endocrine glands including thyroid, adrenal, and pituitary; esophagus; female genital tract including cervix, uterus, ovaries, choriocarcinoma and gestational trophoblastic disease; gallbladder; hypopharynx; liver; lung; lymphomas including both Hodgkin's and non-Hodgkin's lymphomas; male genital tract including prostate, seminal vesicles, testes and germ cell tumors; oropharynx; pancreas; rectum; skin including hemangiomas, melanomas, sarcomas arising from bone or soft tissues and Kaposi's sarcoma; small intestine; solid tumors arising from hematopoietic malignancies such as leukemias and including chloromas, plasmacytomas, plaques and tumors of mycosis fungoides and cutaneous T-cell lymphoma/leukemia; stomach; tumors of the brain, nerves, eyes, and meninges including astrocytomas, glioblastomas, gliomas, neuromas, neuroblastomas, retinoblastomas, Schwannomas and meningiomas; urinary tract including kidney; and urothelium.

It is understood that any of these kringle fusion peptides, the kringle fragment peptides, and the modified kringle fragment peptides disclosed in the present invention may also be useful for the inhibition or prevention of metastases from the tumors described above either when used alone or when used in combination with radiotherapy and/or other chemotherapeutic treatments conventionally administered to patients for treating angiogenic diseases.

For example, when used in the treatment of solid tumors, compounds of the present invention may be administered with chemotherapeutic agents such as alpha inteferon, angioinhibins, CM-101, COMP (cyclophosphamide, vincristine, methotrexate and prednisone), cyclophosphamide, doxorubicin, etoposide/mechlorethamine, LM-609, mBACOD (methortrexate, bleomycin, doxorubicin, cyclophosphamide, vincristine and dexamethasone), pentosan polysulfate, platelet factor 4, prednisone and procarbazine, PRO-MACE/MOPP (prednisone, methotrexate (w/leucovin rescue), taxol, Techgalan, thalidomide, SP-PG, SU-101, TNP-470, vincristine, vinblastine, angiostatin, and the like.

Other chemotherapeutic agents include alkylating agents such as antitumor antibiotics that can include actinomycin D; anthracyclines that can include doxorubicin, bleomycin, mitomycin C and methramycin; folic acid analogs that can include methotrexate; hormones and hormone antagonists including tamoxifen and cortiosteroids and miscellaneous agents including cisplatin and brequinar; nitrogen mustards that can include mechloethamine, melphan, chlorambucil, cyclophosphamide and ifosfamide; nitrosoureas that can include carmustine, lomustine, semustine and streptozocin; alkyl sulfonates including busulfan; purine analogs that can include 6-mercaptopurine and 6-thioguanine; pyrimidine analogues that can include 5-fluorouracil, cytosine arabinoside; and triazines that can include dacarbazine; ethyenimines including thiotepa and hexamethylmelamine. For example, a tumor may be treated conventionally with surgery, radiation or chemotherapy and followed by administration of any of the kringle fusion peptides, the kringle fragment peptides and the modified kringle fragment peptides of the present invention to extend the dormancy of micrometastases and to stabilize and at least inhibit the growth of any residual primary tumor. Any of the kringle fusion peptides, the kringle fragment peptides and the modified kringle fragment peptides of the present invention may be used in the form of pharmaceutically acceptable salts derived from inorganic or organic acids. Wherein "pharmaceutically acceptable salt" is meant those salts which are suitable for use in contact with humans and other animals without undue allergic response irritation, and toxicity, and the like and are commensurate with a reasonable benefit/risk ratio.

It is understood that any of these kringle fusion peptides, the kringle fragment peptides, and the modified kringle fragment peptides of the present invention may also include but not limited to pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may be designed to provide for rapid or slow release; immediate, delayed, timed, or sustained release; or a combination thereof.

Pharmaceutically acceptable salts may be prepared in situ during the final isolation and purification of the compounds of the present invention or separately by reacting a free base function with a suitable organic acid. Representative acid addition salts can include, but are not limited to acetate, adipate, alginate, aspartate, benzoate, benzenesulfonate, bicarbonate, bisulfate, butyrate, camphorate, camphor sufonate, citrate, digluconate, glycerophosphate, hemisulfate, heptanoate, hexanoate, fumarate, glutamate, hydrochloride, hydrobromide, hydroiodide, 2-hydroxyethansulfonate (isethionate), lactate, maleate, methanesulfonate, nicotiuate, 2-naphthalenesulfonate, oxalate, pamoate, pectinate, persulfate, 3-phenylpropionate, phosphate, picrate, pivalate, propionate, p-toluenesulfonate, succinate, tartrate, thiocyanate, and undecanoate. Pharmaceutically acceptable salts may include basic nitrogen-containing groups that are quaternized with agents such as lower alkyl halides which include methyl, ethyl, propyl, and butyl chlorides, bromides and iodides; arylalkyl halides like benzyl and phenethyl bromides; dialkyl sulfates like dimethyl, diethyl, dibutyl and diamyl sulfates; long chain halides such as decyl, lauryl, myristyl and stearyl chlorides, bromides and iodides; and others. Pharmaceutically acceptable salts may also include water or oil-soluble or dispersible products and colloidal products. Examples of acids which may be employed to form pharmaceutically acceptable acid addition salts include such inorganic acids, such as hydrochloric acid, and hydrobromic acid; phosphoric acid; and sulphuric acid, and organic acids as citric acid, oxalic acid, maleic acid, and succinic acid.

Pharmaceutically acceptable salts may also include basic addition salts prepared in situ during the final isolation and purification of any of these kringle fusion peptides, the kringle fragment peptides, and the modified kringle fragment peptides of the present invention by reacting a carboxylic acid-containing moiety with a suitable base such as the bicarbonate, carbonate or hydroxide of a pharmaceutically acceptable metal cation or with ammonia or with an organic primary, secondary or tertiary amine. Pharmaceutically acceptable salts may include, but are not limited to, cations based on alkali metals or alkaline earth metals such as aluminum, calcium, lithium, magnesium, potassium, sodium, and salts and the like and quaternary ammonia and amine cations that can include ammonium, methylamine, ethylamine, dimethylamine, diethylamine, trimethylamine, triethylamine, tetramethylammonium, tetraethylammonium, and the like. Other representative organic amines useful for the formation of base addition salts include diethanolamine, ethanolamine, ethylenediamine, piperidine, piperazine and the like. Preferred salts of the compounds of the invention include acetate, phosphate, and tris salts.

It is also understood that any of these kringle fusion peptides, the kringle fragment peptides, and the modified kringle fragment peptides of the present invention may be combined with pharmaceutically acceptable sustained-release matrices, such as biodegradable polymers, to form therapeutic compositions. As used herein a sustained-release matrix is understood to be a matrix made of materials, usually polymers, which are degradable by enzymatic or acid-base hydrolysis or by dissolution. Once inserted into the body, the sustained-release matrix is intended to be acted upon by enzymes and body fluids. A sustained-release matrix includes, but not limited to biocompatible materials such as polyanhydrides, polyglycolide (polymer of glycolic acid), poly(ortho)esters, polypeptides, polylactides (polylactic acid), polylactide co-glycolide (copolymers of lactic acid and glycolic acid), collagen, hyaluronic acid, liposomes, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable sustained-release matrix includes at least one of either polylactide, polyglycolide, or polylactide co-glycolide (co-polymers of lactic acid and glycolic acid).

It is also understood that any of these kringle fusion peptides, the kringle fragment peptides, and the modified kringle fragment peptides of the present invention may be combined with any number of pharmaceutically acceptable excipients or carriers to form any number of therapeutic compositions. It is understood herein that a pharmaceutically acceptable carrier or excipient refers to a non-toxic solid, semi-solid or liquid filler, diluent, encapsulating material or formulation auxiliary of any type. These therapeutic compositions may be administered bucally, intracisternally, intravaginally, intraperitoneally, parenterally, rectally, sublingually, or topically. It is understood herein that the term "parenteral," is meant to refer to modes of administration which include intramuscular, intraperitoneal, intrasternal, intravenous, subcutaneous and intraarticular injection, and infusion.

Pharmaceutical compositions for the use of parenteral injection can include, but not limited to, pharmaceutically acceptable sterile aqueous or nonaqueous solutions, dispersions, emulsions, or suspensions as well as sterile solid powders for us in reconstitution into sterile injectable solutions or dispersions prior to use. Suitable aqueous and nonaqueous carriers, diluents, solvents and/or vehicles may include water, ethanol, polyols (such as glycerol, polyethylene glycol, propylene glycol, and the like), carboxymethylcellulose and, vegetable oils (e.g., safflower, sunflower or olive oils) and organic esters such as ethyl oleate. Coating or surfactants materials such as lecithin may also be incorporated to ensure that proper fluidity is maintained, for example, maintaining of the required particle size in the case of dispersions. These compositions may also contain additional component agents such as dispersing agents, emulsifying agents, preservatives, wetting agents, antibacterial and antifungal agents such as chlorobutanol, paraben, phenol sorbic acid and the like. Isotonic agents such as sugars, sodium chloride and the like may also be added.

To extend or to prolong the absorption of any of these kringle fusion peptides, the kringle fragment peptides, and the modified kringle fragment peptides of the present invention can be formatted in the injectable pharmaceutical forms that may be brought about by the inclusion of agents, such as aluminum monostearate and gelatin, which delay absorption. Microencapsule matrices of biodegradable polymers containing any of these kringle fusion peptides, the kringle fragment peptides, and the modified kringle fragment peptides of the present invention can be made into injectable depot forms from materials such as polylactide-polyglycolide, poly(orthoesters) and poly(anhydrides). These injectable depot forms can be designed to specifically control the rate of drug release. Depot injectable formulations entrapping the drug can also be configured as time release units for insertion into body tissues.

Topical application includes application to the surface of the body, such as to the skin, eyes, mucosa and lips, which can be in or on any part of the body, including but not limited to the epidermis, any other dermis, or any other body tissue. Topical administration or application is understood to be the direct contact of the pharmaceutical preparation according to the invention with tissue, such as skin or membrane, particularly the cornea, or oral, vaginal or anorectal mucosa. Thus topical application refers to application of the active ingredient to the tissue of an accessible body surface, such as, for example, the skin (the outer integument or covering) and the mucosa surfaces such as eyes, mouth (such as the lips, tongue, gums, cheeks, sublingual and roof of the mouth), larynx, esophagus, bronchus, trachea, nasal passages, vagina and rectum/anus.

It is understood that one skilled in the art of administering active ingredient dosages of any of these kringle fusion peptides, the kringle fragment peptides, and the modified kringle fragment peptides of the present invention can vary from patient to patient. Determining an optimal dosage often times involves the balancing of the level of therapeutic benefit against any risk or deleterious side effects. The selected dosage level will also depend on factors including, but not limited to, the activity of the active ingredient, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The dosage of the active ingredient and route of administration will ultimately be at the discretion of the physician, veterinarian, or clinician, although generally the dosage will be selected to achieve local concentrations at the site of action which achieve the desired effect without causing substantial harmful or deleterious side-effects.

The route of administration can be performed in a single (i.e., bolus), continuous or intermittent dosage protocol (e.g., in divided doses at appropriate intervals) throughout the course of treatment. Methods of determining the most effective dosage protocol and dosage of administration are well known to those of skilled in the art (e.g., the treating physician, veterinarian, or clinician) and will vary with the formulation used for therapy, the purpose of the therapy, the target cell(s) being treated, and the subject being treated. In general, a suitable dosage of the active compound is in the range of about 100 ng to about 300 mg (more typically about 1 µg to about 10 mg) per kilogram body weight of the subject per day. Where the active ingredient is a salt, an ester, an amide, a prodrug, or the like, the amount administered is calculated on the basis of the parent compound and so the actual weight to be used is increased proportionately.

A therapeutically effective amount of one of the compounds of the present invention may be employed in pure form or, where such forms exist, in pharmaceutically acceptable salt form and with or without a pharmaceutically acceptable excipient. A "therapeutically effective amount" of the compounds of the present invention is understood to mean a sufficient amount of the compound to treat an angiogenic disease (for example, to limit tumor growth or to slow or inhibit or block tumor metastasis) at a reasonable benefit/risk ratio applicable to the treatment. It will be understood, however, that the total daily usage of the compounds and compositions of the present invention will be decided by the attending physician, veterinarian, or clinician within the scope of sound medical judgment. The specific therapeutically effective dosage level for any particular patient will depend upon a number of diverse factors which include, but not limited to, the disorder being treated and the severity of the disorder; the activity of the specific compound employed; the specific composition employed; the patient's age, body weight, general health, sex, and diet; the administration time; the route of administration; the rate of bio-elimination of the specific compound; the duration of the treatment; any other drugs used in combination or coincidental with the specific compound employed. A typical administration protocol is understood to start at dosages at levels lower than those required to achieve the desired therapeutic effect and to subsequently increase the dosage gradually until the desired effect is achieved. The total daily dose of any of these kringle fusion peptides, the kringle fragment peptides, and the modified kringle fragment peptides of the present invention can be administered locally or systemically to a human or other mammal host in single or divided doses may be in amounts, for example, from 100 ng to about 300 mg (more typically about 1 µg to about 10 mg)/body weight daily and more usually 1 to 300 mg/kg body weight. The effective daily dosage may be subdivided into multiple dosages for purposes of administration. Consequently, single dosage compositions may contain submultiples thereof that constitute the daily dose.

It is understood that various other agents which can be combined with the compound of the present invention for the inhibition, treatment or prophylaxis of angiogenic diseases are not limited to those listed above, but include, in principle, any agents useful for the treatment or prophylaxis of angiogenic diseases.

It is understood that any of these kringle fusion peptides, the kringle fragment peptides, and the modified kringle fragment peptides of the present invention can be expressed in mammalian cells, yeast, bacteria, or other cells under the control of appropriate promoters. Cell-free translation systems can also be employed to produce such peptides using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, (Cold Spring Harbor, N.Y., 1989), which is hereby incorporated by reference. The constructs in host cells can be used in a conventional manner to produce the gene product encoded by the recombinant sequence. Alternatively, any of these kringle fusion peptides, the kringle fragment peptides, and the modified kringle fragment peptides of the present invention can be synthetically produced by any number of conventional peptide synthesizers.

It is also understood that any of these kringle fusion peptides, the kringle fragment peptides, and the modified kringle fragment peptides of the present invention may also be produced and used in a variety of applications such as (1) as agonists and antagonists active at the various kringle binding sites, (2) as antigens in the development of specific antisera, (3) as peptides for use in diagnostic kits and (4) as peptides linked to or used in combination with cytotoxic agents for targeted killing of cells that bind the various kringle peptide fragments. The amino acid sequences of these peptide fragments may be selected on the basis of their respective position on the exterior regions of the molecule which are accessible for binding to antisera or the inhibitory potency of the peptide fragments toward processes arising from or exacerbated by angiogenesis. In addition, these peptide kringle fragment sequences may be compared to known sequences using protein sequence databases such as GenBank, Brookhaven Protein, SWISS-PROT, and PIR to determine potential sequence homologies. This information facilitates elimination of sequences that exhibit a high degree of sequence homology to other molecules and thereby enhances the potential for high specificity in the development of antisera, agonists and antagonists to these various kringles.

Any of these kringle fusion peptides, the kringle fragment peptides, and the modified kringle fragment peptides of the present invention may also be used as a way to isolate corresponding receptors by using immobilization of the kringle fusion protein or kringle peptide fragments on a solid support in, for example, an affinity column through which cultured endothelial cells or membrane extracts are passed. Isolation and purification of these kringle receptors may then be followed by amino acid sequencing to specifically identify and isolate polynucleotides which encode these kringle receptors. It is envisioned that such polynucleotides may then be cloned into a suitable expression vector and transfected into tumor cells. Expression of these kringle receptors by the transfected tumor cells could enhance the responsiveness of these cells to endogenous or exogenous kringle peptide fragments and thereby inhibit, reverse or decrease the rate of metastatic growth. Furthermore, it is envisioned that recombinant expression of these receptors could allow greater amounts of receptors to be produced, such that sufficient quantities can be produced for use in high throughput screening assays to identify smaller antagonists which mimic the action of kringle.

Systematic substitution of amino acids of any of these kringle fusion peptides, the kringle fragment peptides, and the modified kringle fragment peptides of the present invention within these respective synthesized peptides may yield high affinity agonists and antagonists to these kringle receptors that enhance or diminish binding to its receptor. Such agonists may be used to suppress the growth of micrometastases and as a result may be used to limit the spread of cancer. In cases of inadequate vascularization, antagonists to any of these kringle fusion peptides, the kringle fragment peptides, and the modified kringle fragment peptides of the present invention may be applied to block the inhibitory effects of any of these kringle fusion peptides, the kringle fragment peptides, and the modified kringle fragment peptides of the present invention to promote angiogenesis. As a result this type of treatment may realize therapeutic effects in promoting wound healing such as in diabetics.

Any of these kringle fusion peptides, the kringle fragment peptides, and the modified kringle fragment peptides of the present invention can also be used as antigens to generate polyclonal or monoclonal antibodies that are specific for the various kringle inhibitors. Antibodies could be used in detecting kringle peptide fragments in bodily fluids or in tissue for diagnosing or determining the prognostic relevance of the various kringle peptide fragments.

Kits for measurement of kringle fusion peptides or kringle peptide fragments of the present invention are also contemplated as part of the present invention. Antisera that possess the highest titer and specificity and can be used to detect fusion peptides or kringle peptide fragments of the present invention in extracts of plasma, saliva, urine, tissues and cell culture media may be used to develop kit assays that are capable of rapid, reliable, sensitive and specific measurement and localization of the various kringle peptide fragments. These assay kits can include: competitive and non-competitive assays, bioluminescence and chemilumenescence assays, fluorometric assays, immunoradiometric assays, sandwich assays, radioimmunoassays, dot blots, ELISAs, microtiter plates, immunocytochemistry and antibody-coated strips or dipsticks kits for rapid monitoring of urine, saliva, or blood. For each kit the range, specificity, reproducibility, sensitivity, precision, and reliability of the kit assay can be optimized by those skilled in the art.

Binding Example 1

ROR1 is a Surface Receptor for GRP78 on Glioma Cells

Since the mechanism of action is inconclusive for soluble, surface bound GRP78, we decided to identify the surface receptor for GRP78 on glioma (D54) cells. Using GRP78 (StressMarq) labeled with Biotin (Sigma, Mix-n-Match), pull down experiments were performed. 2×10(6) D54 glioma cells were grown in a T25 cm flask with full DMEM media overnight. The next day the media was removed and the cells were washed with ice cold PBS. To the attached cells ice cold octyl-lysis buffer (Pierce detergent cell lysis kit) was added and the cells were scrapped off and incubated in a tube with gentle agitation at 4 C for 60 minute. The microcentrifuge tube was centrifuged at 12,000×g for 20 minutes. The supernatant was gently removed and placed on ice. The supernatant was precleared with a biotin-agarose binding step. Finally, 10 µg/ml GRP78-Biotin was added to the precleared D54 cell supernatant and incubated at 4° C. overnight. The GRP78 bound peptides were bound to neutravidin-agarose with a 60 minute incubation at room temperature. The bound peptides were separated with a filtered spin column. The column was washed twice with cold PBS. Finally, the GRP78 bound peptides were released with pH 3 glycine buffer. Polyacrylamide gel electrophoresis was performed on the released fractions and mass spectrometry analysis of the gel protein bands was also performed. This showed that identified ROR1 acts as a GRP78 surface receptor on D54 glioma cells. The immunoprecipitation of ROR1 using GRP78-Biotin also showed that ROR1 binding to GRP78 can be completely blocked with a GRP78 antagonist, K5(3-89 Active Zone)frag SEQ ID NO: 1, but not by a C-terminal GRP78 antibody or unfolded K5 (FIG. 5).

Binding Example 2

GRP78 Binds to ROR1 on Dendritic Cells (DCs)

To determine whether ROR1 is expressed on dendritic cells CD14+ cells were isolated from human PBMCs and cultured in 10 ng/ml GM-CSF, and 10 ng/ml IL-4 for 7 days to produce immature DCs. The immature DCs were stained for ROR1 expression and analyzed by flow cytometry analysis (FIG. 6). As can clearly be seen, immature dendritic cells express ROR1. We also used GRP78-biotin binding to lysed dendritic cells (protocol listed in Example 1) and precipitation with neutravidin-agarose and Western blot analysis with an ROR1 antibody. From the Western Blot, ROR1(100 kDa) was pulled down with the GRP78-biotin-streptavidin-agarose experiments. We believe this is the first data showing that ROR1 is present on dendritic cells and that GRP78 binds to surface ROR1. It is known that the receptor for GRP78 on dendritic cells is CD14. Our data does not dispute this finding because we believe that there is a complex of peptides with ROR1 and GRP78 (FIG. 1) on cell surfaces. In fact, we used about 8 different solubilizing detergents from RIPA buffer to Peirce's surface protein isolation kits to an octyl-detergent to obtain a strong protein signal with GRP78 pulldowns. The only lysis agent that could bring down a unique strong signal protein band (ROR1) along with some other protein bands of much weaker signals (that were seen in the other lysis agents) was the Octyl-detergent lysis agent. ROR1 is a very hydrophobic protein and this result could help explain why we are the first to show that ROR1 is a surface GRP78 binding protein.

Binding Example 3

GRP78 and ROR1 Bind Together on the Cell Surface of Glioma U87 Cells

Figure 17:
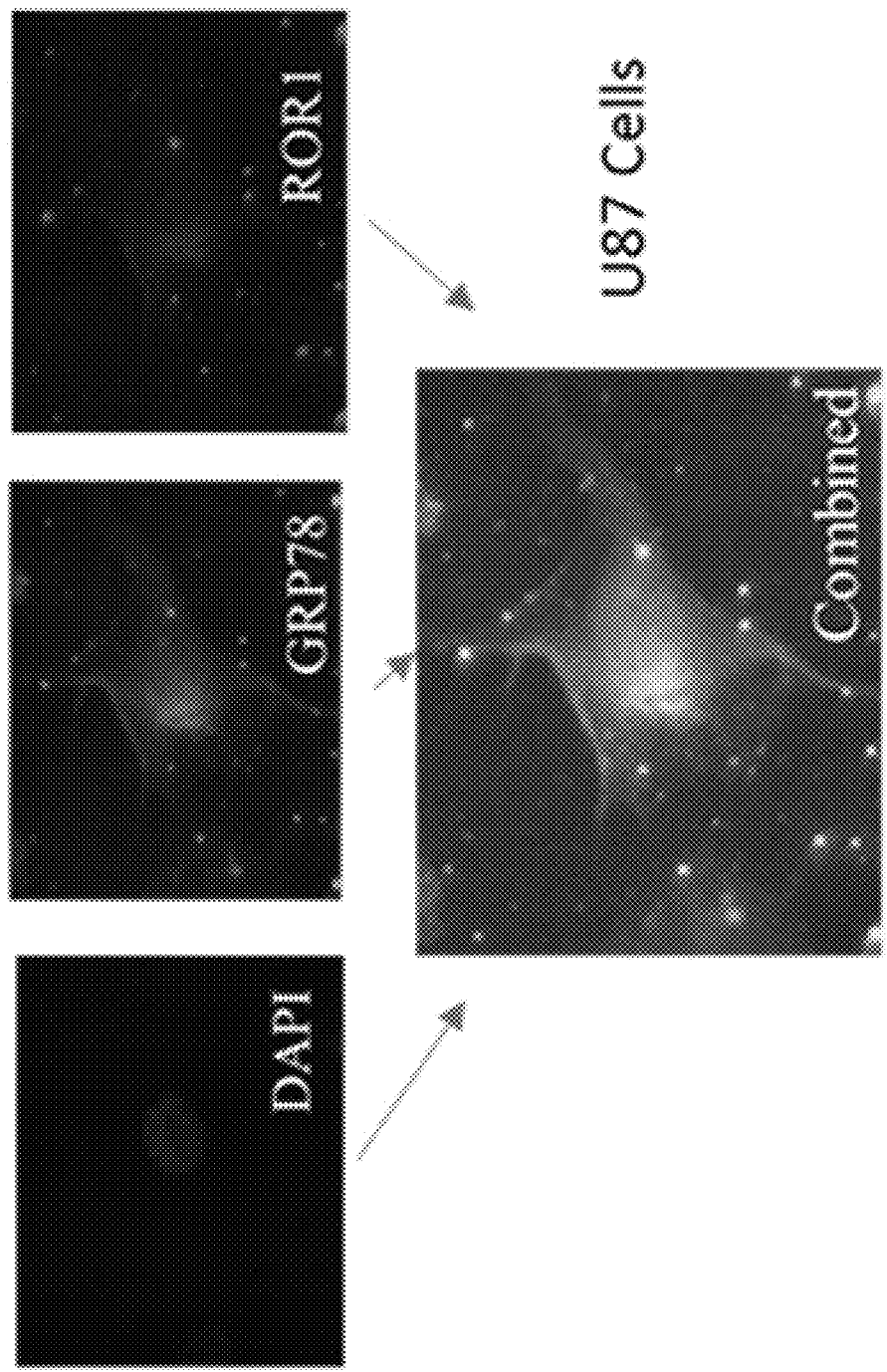
FIG. 17 U87 glioma cells fixed with BD Cytofix and then stained with an anti-GRP78-FITC (Abcam) and anti-ROR1-FireRed (Biolegend) antibodies that show GRP78 (stained with Green) and anti-ROR1 (Red) bind on the cell surface and to each other (yellow) showing that GRP78 is also present on the surface of these tumor cells in that one of the surface binding peptides for GRP78 is an orphan tyrosine kinase, ROR1.

To understand if ROR1 and GRP78 bind on cell surfaces and not just in cell surface lysates, 10,000 U87 glioma cells per ml were plated on a 4 well tissue coated coverslips overnight at 37° C., 8% $CO_2$. After attachment, GRP78 was added to the cells for 2 hours at 4° C. The cells were fixed with BD Cytofix but not permeabilized due to internal GRP78 protein. U87 glioma cells were then stained for 1 hour at room temperature with an anti-GRP78-FITC (Abcam) and anti-ROR1-FireRed (Biolegend) antibodies that show GRP78 (Green) and ROR1 (Red) bind on the cell surface and to each other (yellow) (FIG. 17). We have previously shown that GRP78 is not only an endoplasmic reticulum resident protein but is also present on the surface of many tumor cells. This shows that one of the surface binding peptides for GRP78 is an orphan tyrosine kinase, ROR1. Because of our experience with K5(3-89 Active Zone)frag SEQ ID NO:1 and GRP78 binding, we next wanted to define if GRP78 binds to the kringle domain on ROR1. To do this we decided to express the kringle domain of ROR1 independently, i.e., Kr1(1-91 Active Zone)frag SEQ ID NO:19.

Binding Example 4

Figure 18A:
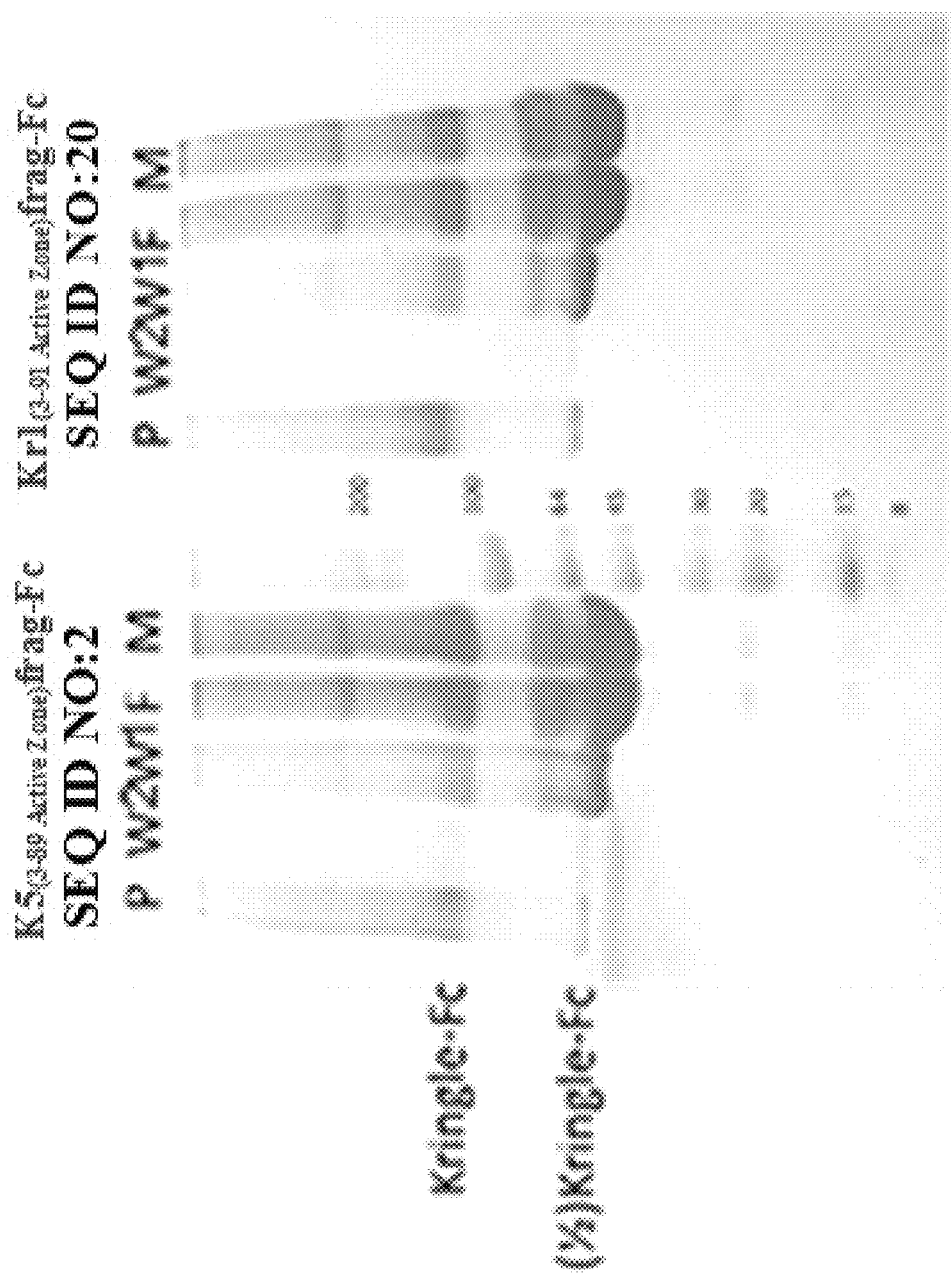
FIG. 18A is PAGE electrophoresis of HEK 293 expressed kringle peptides purified over a Protein Aagarose column or a benzamidine-agarose column separated with 4-20% Tru-PAGE gels, M=media, F=flow through, W1=Wash 1, W2=Wash 2, P=purified eluted protein K5(3-89 Active Zone)frag-Fc SEQ ID NO:2 and Kr1(3-91 Active Zone)frag-Fc SEQ ID NO:20.
Figure 18B:
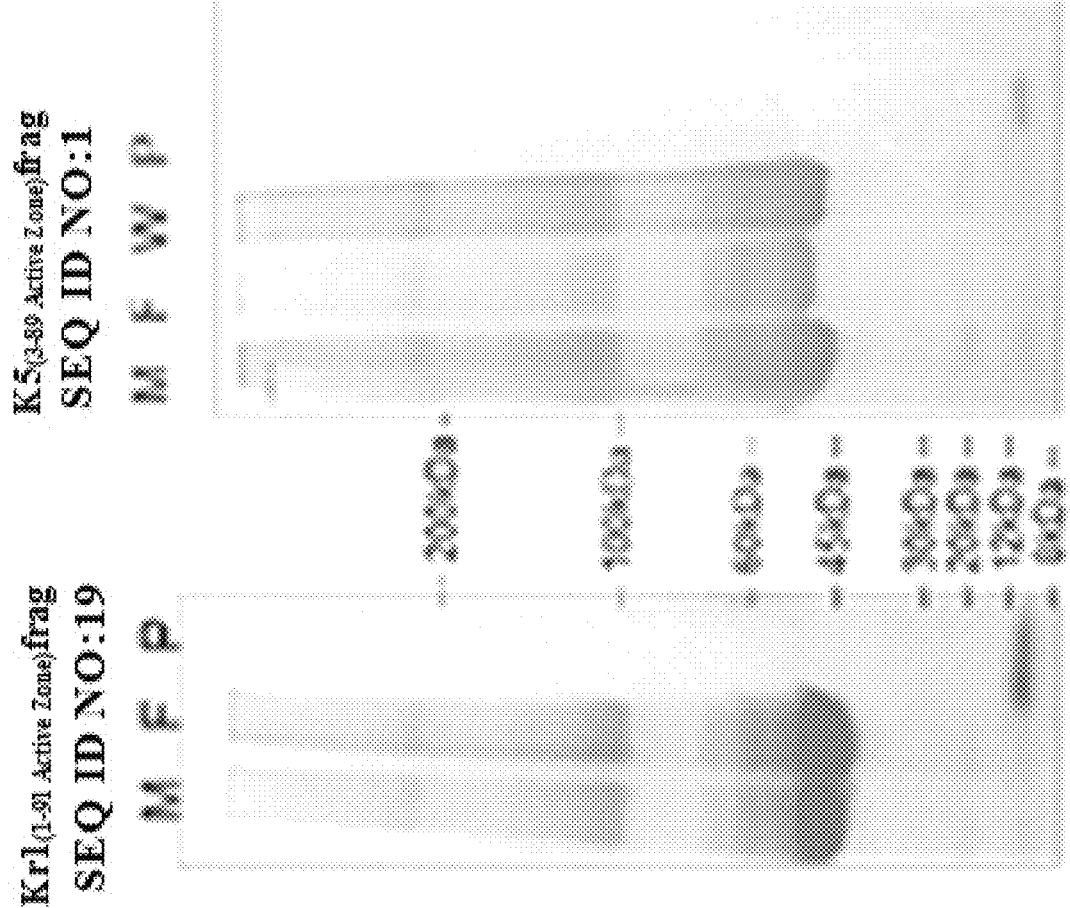
FIG. 18B is PAGE electrophoresis of HEK 293 expressed kringle peptides purified over a Protein Aagarose column or a benzamidine-agarose column with 4-10% TruPAGE gels with Kr1(1-91 Active Zone)frag SEQ ID NO: 19 and K5(3-89 Active Zone)frag SEQ ID NO:1 purified, M=media, F=flow through, W=wash, P=purified eluted protein Kr1(1-91 Active Zone)frag SEQ ID NO:19.

ROR1 Kringle Domain, K5 Kringle Domain and the Kringle-Fusion Peptides of Each can be Expressed in 293T Cells To further define this mechanism of action for GRP78 and ROR1 binding, we expressed and purified human K5 (i.e., K5(3-89 Active Zone)frag SEQ ID NO:1), the ROR1 kringle (i.e., Kr1(1-91 Active Zone)frag SEQ ID NO: 19) and the corresponding fusion peptides, (i.e., K5(3-89 Active Zone) frag-Fc SEQ ID NO:2 and Kr1(3-91 Active Zone)frag-Fc SEQ ID NO:20) of each in 293T cells (FIGS. 18A-18C). K5(3-89 Active Zone)frag SEQ ID NO:1 (amino acids 477-563 HPg), Kr1(1-91 Active Zone)frag SEQ ID NO: 19 (amino acids 308-400 ROR1), K5(3-89 Active Zone)frag-Fc SEQ ID NO:2 (Ig amino acids 100-330) and Kr1(3-91

Active Zone)frag-Fc SEQ ID NO:20 (Ig amino acids 102-330) were synthesized at GenScript in a pUC 3.1 vector. The two Kringle domains were expressed as respective fusion proteins for possible improvement of half-life for in vivo studies. We have previously determined the half-life of K5(3-89 Active Zone)frag SEQ ID NO:1 to be about 20 min in mice and about 1.5 hours in monkeys. Each DNA (1 μg/ml) was transiently transfected in attached T75 flasks containing 80% confluent 293T cells using PEI (3:1 PEI:DNA). After 24 hours, 1:1 amount of new media was added to the flasks and allowed to grow for 5 days at 37 C and 8% $CO_2$. The media was collected and spun at 1500×g for 10 min. K5(3-89 Active Zone)frag SEQ ID NO:1 and Kr1(1-91 Active Zone)frag SEQ ID NO: 19 were purified from spent media over a para-amino-benzamidine agarose column. The bound kringles were eluted with 300 nM p-amino benzamidine. The fusion peptide compounds, i.e., K5(3-89 Active Zone)frag-Fc SEQ ID NO:2 and Kr1(3-91 Active Zone)frag-Fc SEQ ID NO:20, were purified over a Protein A-agarose column and eluted with 150 mM glycine buffer at pH 3.0. Both sets of purified peptides were dialyzed against PBS. As can be seen from the PAGE protein gels, the purified K5(3-89 Active Zone)frag SEQ ID NO:1 and Kr1(1-91 Active Zone)frag SEQ ID NO:19 showed >90% purity from the protein gels (FIG. 18B). The fusion peptides, i.e., K5(3-89 Active Zone)frag-Fc SEQ ID NO:2 and Kr1(3-91 Active Zone)frag-Fc SEQ ID NO:20, showed two bands purified on PAGE gels (FIG. 18A). The major top band at about 1 20 kDa (85%) is the dual (i.e., a dimerized) kringle complete fusion compound domain (FIG. 18C). The minor bottom band is the half fusion protein that did not dimerize by disulfide linking.

Binding Example 5

Kr1, K5, Kr1-Fc and K5-Fc Bind Tightly to GRP78

Figure 19B:
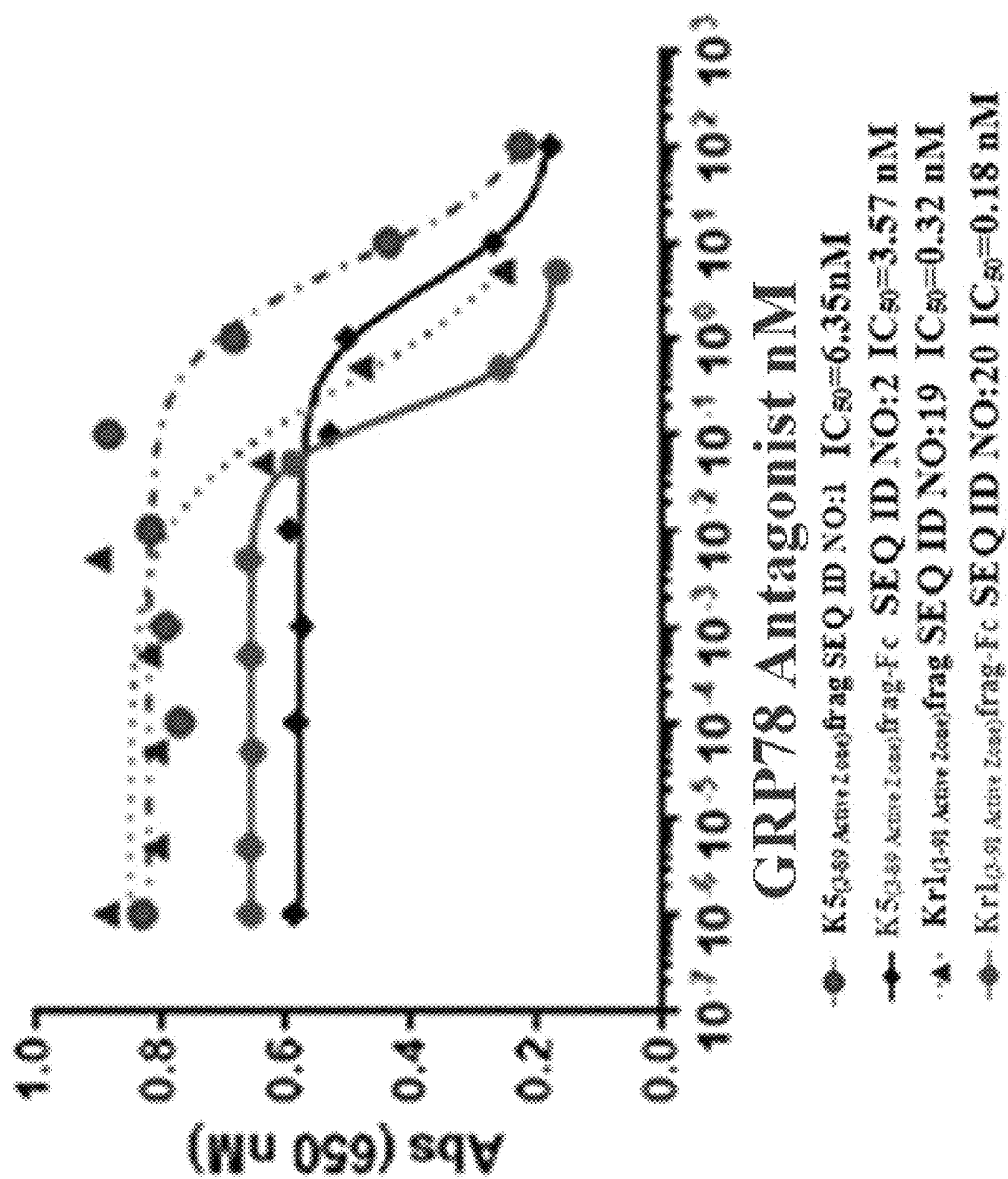
FIG. 19B show results of GRP78 antagonists competition binding to GRP78 in which GRP78 was coated on a 96 well plate and a fixed concentration (2 nM) of K5(3-89 Active Zone)frag SEQ ID NO:1-biotin was added. The data shows competition binding assays were performed with the fusion and other kringle domains wherein (green -●-) K5(3-89 Active Zone)frag SEQ ID NO:1; (black -●-) K5(3-89 Active Zone)frag-Fc SEQ ID NO:2; (blue -▲-) Kr1(1-91 Active Zone)frag SEQ ID NO:19; and (red -●-) Kr1(3-91 Active Zone)frag-Fc SEQ ID NO:20.

Comparison of GRP78 binding for the two kringle domains was performed by a GRP78 ELISA. GRP78 (StressMarq) (1 ug/ml@ 100 μl/well) was bound to a tissue culture coated 96 well plate overnight at 4° C. After washing 3× with PBS, the plates were blocked with superblock (Pierce) for 1 hour at room temperature. The block was removed and K5-biotin complex (i.e., K5(3-89 Active Zone) frag SEQ ID NO:1-biotin complex) and Kr1-biotin complex (i.e., Kr1(1-91 Active Zone)frag SEQ ID NO:19-biotin complex) were added to the plate at increasing concentrations (0.1 pM to 100 nM) at 4° C. for 2 hours. The plate was then washed 3× with PBS again and Neutra-avidin-HRP was added to the wells for 1 hour at room temperature. The wells were washed again with PBS and one step TMB (Pierce) was added to the wells with absorbance recorded after 30 minutes to measure kringle binding. We found that Kr1-biotin complex (i.e., Kr1(1-91 Active Zone)frag SEQ ID NO:19-biotin complex) (Kd=0.03 nM) bound to GRP78 20×s tighter than the K5-biotin complex (i.e., K5(3-89 Active Zone)frag SEQ ID NO:1-biotin complex) (Kd=0.6 nM) (FIG. 19A). We also wanted to test the binding affinity of the Fc fusion kringles K5-Fc (i.e., K5(3-89 Active Zone) frag-Fc SEQ ID NO:2) and Kr1-Fc (i.e., Kr1(3-91 Active Zone)frag-Fc SEQ ID NO:20) that have dual kringle binding domains on each of the corresponding dimerized fusion peptides (FIG. 18C). To analyze these peptides for binding to GRP78, we used a 96 well competition binding assay. The assay consisted of binding GRP78 to a tissue coated 96 well plate as listed above. 2 nM of the K5-biotin complex (i.e., K5(3-89 Active Zone)frag SEQ ID NO:1-biotin complex) was then added to the wells along with various concentrations (0.1 pM to 100 nM) of Kr1(1-91 Active Zone)frag SEQ ID NO:19, unlabeled K5(3-89 Active Zone)frag SEQ ID NO:1, Kr1(3-91 Active Zone)frag-Fc SEQ ID NO:20, and K5(3-89 Active Zone)frag-Fc SEQ ID NO:2 peptides and incubated at 4 C for 2 hours. After the plate was washed, Neutra-avidin-HRP was added and bound K5 was measured by adding HRP substrate, TMB, as listed above. The competition binding assay showed that all the GRP78 antagonists competed with K5-biotin complex (i.e., K5(3-89 Active Zone)frag SEQ ID NO:1-biotin complex) binding to GRP78 below 10 nM. The assay showed that the potency ranking for these GRP78 antagonists is Kr1(3-91 Active Zone)frag-Fc SEQ ID NO:20<Kr1(1-91 Active Zone)frag SEQ ID NO:19<K5(3-89 Active Zone)frag-Fc SEQ ID NO:2<K5(3-89 Active Zone)frag SEQ ID NO:1 (FIG. 19B).

Inhibition Example 1

Kr1 and K5 Potent Inhibition Endothelial Cell Migration

Although we could show potent binding to GRP78 for our peptide kringles and fusion peptides, we wanted to determine if these GRP78 binding peptides could antagonize the functional activity of GRP78 on endothelial cell migration, tumor cell growth, and the induced tolerogenic phenotype of dendritic cells. Since we have published that a correctly folded K5(3-89 Active Zone)frag SEQ ID NO:1 can inhibit endothelial cell migration, we decided to compare the newly expressed K5(3-89 Active Zone)frag SEQ ID NO:1 with the Kr1(1-91 Active Zone)frag SEQ ID NO:19 for function activity. For this assay, endothelial cell migration was determined by using 96-well plates with a cellulose membrane between the upper and the lower chambers (Neuroprobe). HMVECs (AllCells) were starved of growth factors overnight, labeled with fluorescent calcein AM (50-100 nmol/L), plated onto the top 96-cell migration chamber ($2.9 \times 10^4$ cells per well) and stimulated to migrate with VEGF (5 ng/mL) added to the bottom side of the chamber. After 24 hours, migrated cells were measured by fluorescence. To determine if the GRP78 antagonists could inhibit endothelial cell migration, the GRP78 antagonists were added in an increasing concentration dependent manner to the bottom chamber. Starved and fluorescently labeled HUMVECs were added to the top of a migration chamber. The bottom chamber contained the bFGF and the various kringle domains. The cells were let migration for 24 hours and the fluorescence of the bottom well was measured. After 24 hours, the top cells were wiped off the plate and the bottom wells were measured for fluorescently labeled cells that migrated. Functional inhibition activities of K5(3-89 Active Zone)frag SEQ ID NO:1 and Kr1(1-91 Active Zone)frag SEQ ID NO:19 were compared (FIG. 7). As expected from the binding data to GRP78, the Kr1(1-91 Active Zone)frag SEQ ID NO:19 was more potent (50×) for inhibition of endothelial cell migration than K5(3-89 Active Zone)frag SEQ ID NO: 1.

Inhibition Example 2

Kr1 and K5 Inhibit Tumor Cell Proliferation

To determine if the GRP78 antagonists could inhibit tumor cell proliferation directly, we tested Kr1(1-91 Active Zone)frag SEQ ID NO:19 and K5(3-89 Active Zone)frag SEQ ID NO:1 against a panel of tumor cells. For the proliferation assay, cells were plated in 96 well plates at approximately 3000 cells per well overnight. The media was removed and fresh media with 1% FBS containing 10 µg/ml GRP78 was added along with the GRP78 antagonists. The plates were incubated for 72 hours at 37 C in 8% $CO_2$. After 72 hours, cell number was determined with a WST-8 cell proliferation kit (Sigma). As can be seen from the Table 2 below, the GRP78 antagonists (i.e., K5(3-89 Active Zone)frag SEQ ID NO:1 and Kr1(1-91 Active Zone)frag SEQ ID NO: 19) exhibit a potent dose response inhibition of tumor cell proliferation. However, these GRP78 antagonists do not inhibit the normal human kidney 293 cell proliferation. The inhibition of tumor cell proliferation by Kr1(1-91 Active Zone)frag SEQ ID NO:19 is several fold more potent than K5(3-89 Active Zone)frag SEQ ID NO: 1. The only tumor cell line tested to not be inhibited by GRP78 antagonists was HT29, a colon carcinoma cell line. From our previous data above, we know U87 and D54 have ROR1 expressed on their cell surfaces.

were with GRP78 and positive controls are without GRP78 but with LPS. For the first time, we can show that GRP78 antagonists can potently block the tolerogenic activity of GRP78 on dendritic cells leading to an activated state (FIG. 8). In a dose dependent inhibition, GRP78 antagonists, (K5(3-89 Active Zone)frag SEQ ID NO:1, Kr1(1-91 Active Zone)frag SEQ ID NO:19, and K5(3-89 Active Zone)frag-Fc SEQ ID NO:2) exhibited potent nM activity and Kr1(3-91 Active Zone)frag-Fc SEQ ID NO:20 exhibited pM activity for reversing the tolerogenic phenotype of dendritic cells induced by GRP78. All of these antagonists decreased expression of PD-L1, B7H4, B7H3, and IL-10 from mature dendritic cells and increased expression of the maturity marker CD86 on dendritic cells (FIGS. 9A-9C).

We have discovered that soluble GRP78 binds to a cell surface orphan tyrosine kinase receptor called ROR1 on dendritic, glioma, and endothelial cells. We can also show that our novel GRP78 antagonists, K5(3-89 Active Zone) frag SEQ ID NO:1, ROR1, Kr1(1-91 Active Zone)frag SEQ

TABLE 2

INHIBITION OF TUMOR CELL PROLIFERATION BY GRP78 ANTAGONISTS

| Cell Line | Tumor type | % Proliferation Inhibition K5(3-89 Active Zone)frag SEQ ID NO: 1 | | | % Proliferation Inhibition Kr1(1-91 Active Zone)frag SEQ ID NO: 19 | | |
|---|---|---|---|---|---|---|---|
| | | 0.1 µg/ml | 1 µg/ml | 10 µg/ml | 0.1 µg/ml | 1 µg/ml | 10 µg/ml |
| D54 | Glioma | 0 ± 5 | 12 ± 6 | 56 ± 5 | 15 ± 3 | 52 ± 6 | 85 ± 3 |
| Calu 6 | Lung carcinoma | 7 ± 2 | 21 ± 3 | 30 ± 4 | 14 ± 2 | 31 ± 5 | 60 ± 5 |
| MDA231 | Breast carcinoma | 2 ± 4 | 13 ± 2 | 46 ± 6 | 33 ± 8 | 63 ± 12 | 86 ± 10 |
| U87 | Glioma | 0 ± 4 | 24 ± 5 | 64 ± 8 | 12 ± 7 | 45 ± 7 | 82 ± 8 |
| HT29 | Colon carcinoma | 0 ± 2 | 10 ± 8 | 0 ± 10 | 0 ± 8 | 10 ± 9 | 0 ± 5 |
| 293 Kidney fibroblasts | Normal cells | 0 ± 8 | 0 ± 10 | 0 ± 6 | 0 ± 5 | 0 ± 6 | 0 ± 7 |

Inhibition Example 3

GRP78 Antagonists can Block the Tolerogenic Phenotype of Dendritic Cells Induced by GRP78

To determine if GRP78 antagonists can block the tolerogenic phenotype of GRP78 treated dendritic cells, we differentiated immature dendritic cells. From 20 million human pooled PBMCs (AllCells), we isolated about 2.5 million CD14+ monocytes using positive selection with a pluribead CD14 kit (Pluriselect). 50,000 purified CD14+ monocytes were added to each well of a 96 well tissue plate and cultured with RPMI-1640 media (Sigma) containing 10% FBS and GM-CSF (500 ng/ml, Sigma) and IL-4 (500 ng/ml, Sigma) in the presence or absence of GRP78 (10 µg/ml, StressMarq) for 7 days with LPS (500 ng/ml, Sigma) added to some wells for the final 2 days to give mature dendritic cells (mDCs). From our multiple studies, we can isolate about 2.5 million CD14+ monocytes from 20 million PBMCs using positive selection with pluribeads (Pluriselect). GRP78 antagonists (K5(3-89 Active Zone)frag SEQ ID NO:1, Kr1(1-91 Active Zone)frag SEQ ID NO:19, K5(3-89 Active Zone)frag-Fc SEQ ID NO:2, and Kr1(3-91 Active Zone)frag-Fc SEQ ID NO:20) were added to the appropriate wells on day 2 at concentrations of 1 pM to 10 nM. On day 8, cells were fixed and aliquots stained at 4 C for various tolerogenic DC markers: PD-I(B7H1), B7H4, B7H1, CD86, CD14, ROR1. Stained cells were analyzed byflow cytometry analysis. All antibodies for the DC markers were PE labeled from BD PharMingen. The cytokine, IL-10 (ENZO Life Sciences), was assayed by ELISA (Sigma). Negative controls wells ID NO:19, K5(3-89 Active Zone)frag-Fc SEQ ID NO:2, and Kr1(3-91 Active Zone)frag-Fc SEQ ID NO:20 can reverse this tolerogenic dendritic cell and resistant tumor cell phenotype induced by GRP78. Our data demonstrates that GRP78 binds to the kringle domain of ROR1 leading to ROR1 signaling through several different non-canonical pathways. This ROR1 signaling in dendritic cells induces a tolerogenic phenotype and a resistant phenotype in tumor cells. We can now show for the first time that blocking the binding to GRP78 to ROR1 on dendritic cells, endothelial cells and tumor cells, leads to reduction of immune tolerance, endothelial cell migration and tumor cell proliferation. With these GRP78 antagonists, we hope to improve the outcome of patient with cancers that express GRP78 for immune evasion and tumor resistance.

General Solid Phase Synthesis of Kringle Peptide Fragments

Any of the kringle fusion compounds, the kringl fragments, and the modified kringle fragments can be synthesized using manual solid-phase synthesis or preferably using automatic synthesizers systems such as using Fmoc protected Rink Amide MBHA resin, Fmoc protected amino acids, O-benzotriazol-1-yl-N,N,N',N'-tetramethyl-uronium hexafluorophosphate (HBTU) in N,N-dimethylformamide (DMF) solution and activation with N-methyl morpholine (NMM), and piperidine deprotection of Fmoc groups (Step A). Selective deprotection of the Lys(Aloc) group can be accomplished (when necessary) by treating the peptide bound resin with Pd(PPh$_3$)$_4$ (usually about a three fold equivalents excess) in CHCl$_3$:NMM:HOAc (18:1:0.5) for an extended amount of time such as 2 hours (Step B). The peptide bound resin can then be repeatedly washed with neat chloroform (preferably up to at least six washes of $CHCl_3$), 20% HOAc in $CH_2Cl_2$ (preferably up to at least six separate washes), neat $CH_2Cl_2$ (preferably up to at least six separate washes), and finally with neat DMF (up to at least six separate washes). In some situations, the synthesis can then be re-automated for the addition of one of acetic acid, the addition of AEEA (aminoethoxyethoxyacetic acid) group, or the addition of a 3-maleimidopropionic acid (MPA) (Step C). Then the synthesized peptide product can be isolated by cleavage from the resin followed by product isolation using 85% TFA (trifluoroacetic acid)/5% TIS/5% thioanisole and 5% phenol, and then precipitated at reduced temperatures (preferably dry-ice) in diethyl ether (Step D). These products can then be further purified by using gradient elution on a HPLC phenyl-hexyl reverse phase column consisting of phenyl groups that are bound to silica surface using a 6-carbon chain (hexyl ligand). The gradient elution profile is preferably programmed to be about 30-55% B (0.045% TFA in water (A) and 0.045% TFA in $CH_3CN$ (B)) over 180 min using with a UV detector at 214 and 254 nm. The following examples will serve to further illustrate the preparation of the novel compounds of the invention:

Synthesis Example 1

SEQ ID NO: 46

Preparation of Kr1(58-81 Active Zone w Ala Sub Cys and w Lys Sub Cys) Frag Peptide Preparing the tide compound, Arg Asn Pro Gly Asn Gln Lys Glu Ala Pro Trp Ala Phe Thr Leu Asp Glu Asn Phe Lys Ser Asp Leu Lys (SEQ ID NO: 46) is preferably performed using an automated peptide synthesis that sequentially adds individual protected amino acids onto a solid phase resin such as a 4-(2',4'-Dimethoxyphenyl-Fmoc-aminomethyl)-phenoxyacetamido-methylbenzhydryl amine resin commonly referred to as a Rink Amide MBHA resin. This methodology comprises one or more amino acids or suitably protected amino acids sequentially added to a growing peptide chain bound to the resin. The carboxyl group of the first amino acid is protected by a suitable protecting group. The protected and/or modified amino acids are then attached to the solid phase support resin by adding the next amino acid in the sequence having the complimentary amino group which is suitably protected and which is under conditions suitable for forming the amide linkage. Afterwards the protecting group is then removed from this growing amino acid residue bound to the resin and then the next sequential and suitably protected amino acid is added, and so forth. Upon completion of sequentially linking together all the desired amino acids in the proper sequence, any remaining protecting groups (and any solid support) are then removed to free up the final desired polypeptide. In particular the resin is initially solvated with DMF for at least about 5 minutes. The Fmoc group is deblocked from the α-N-terminal of the resin-bound amino acid with using about 20% piperidine in DMF for about 15 minutes and then the resin is washed with DMF for about 5 minutes. Subsequently the α-C-terminal of the first amino acid (in this particular sequence which is protected Lysine, Fmoc-Lys (Boc)-OH) is then activated using HBTU (O-benzotriazol-1-yl-N,N,N',N'-tetramethyluronium hexafluorophosphate) and HOBT (1-hydroxybenzotriazole) in DMSO-NMP (N-methylpyrrolidone) and using a diisopropylethylamine in DMSO-NMP. The activated Fmoc-protected amino acid is then coupled to the resin-bound amino acid by exposure to DMF for at least about 30 minutes. Subsequently the resin is washed with DMF for at least about 5 minutes. The process of activating the next amino acid (Fmoc deblocked) in the sequence is followed by coupling the activated amino acid to the growing peptide chain bound to the resin. This process is repeated until all the desired amino acids are in the sequence as outlined below. Afterwards any remaining protecting groups (and any solid support) are then removed to free up the final desired polypeptide. Here the sequentially adding individual protected amino acids after the initial Lysine are as follows: Fmoc-Leu-OH, Fmoc-Asp(OtBu)-OH, Fmoc-Ser(tBu)-OH, Fmoc-Lys(Boc)-OH, Fmoc-Phe-OH, Fmoc-Asn(Trt)-OH, Fmoc-Glu(tBu)-OH, Fmoc-Asp (OtBu)-OH, Fmoc-Leu-OH, Fmoc-Thr(tBu)-OH, Fmoc-Phe-OH, Fmoc-Ala-OH, Fmoc-Trp(Boc)-OH, Fmoc-Pro-OH, Fmoc-Ala-OH, Fmoc-Glu(tBu)-OH, Fmoc-Lys(Boc)-OH, Fmoc-Gln(Trt)-OH, Fmoc-Asn(Trt)-OH, Fmoc-Gly-OH, Fmoc-Pro-OH, Fmoc-Asn(Trt)-OH, and Fmoc-Arg (Pbf)-OH. The resin bound polypeptide is then washed with THF for about 5 minutes to remove DMF and to shrink the resin. The resin is then dried with argon for 10 minutes and nitrogen for 10 minutes more to realize clean, resin-bound peptide. The polypeptide is cleaved from the resin with concomitant deprotection of amino acid side chains by stirring with cleavage reagent (thioanisole, water, ethanedithiol and trifluoroacetic acid). Removal of the polypeptide and deprotection can either be performed in a multistep operation or in a singular operation that treats the resin-bound polypeptide with a cleavage reagent. The Fmoc groups of the N-terminal of the resin-bound amino acid can be deblocked using 20% piperidine in DMF. Subsequent to removal of the polypeptide from the resin, the deblocked free polypeptide is then filtered and rinsed with trifluoroacetic acid. The filtrate is also washed and decanted in a series of cold diethyl ether washes to obtain the polypeptide. The polypeptide, i.e., Kr1(58-81 Active Zone w Ala sub Cys and w Lys sub Cys)frag peptide (SEQ ID NO: 46), can then be further purified by reverse phase HPLC.

Synthesis Example 2

SEQ ID NO: 50

Preparation of Kr1(58-80 Active Zone w Ala Sub Cys)Frag Peptide

The tide compound of Arg Asn Pro Gly Asn Gln Lys Glu Ala Pro Trp Ala Phe Thr Asp Glu Asn Phe Lys Ser Asp Leu (SEQ ID NO: 50) can be prepared using the synthetic sequence as outlined in synthesis example 1 using Fmoc-Leu-OH as the initial amino acid to be attached to the resin. The following amino acids were then sequentially added as follows: Fmoc-Asp(OtBu)-OH, Fmoc-Ser(tBu)-OH, Fmoc-Lys(Boc)-OH, Fmoc-Phe-OH, Fmoc-Asn(Trt)-OH, Fmoc-Glu(tBu)-OH, Fmoc-Asp(OtBu)-OH, Fmoc-Leu-OH, Fmoc-Thr(tBu)-OH, Fmoc-Phe-OH, Fmoc-Ala-OH, Fmoc-Trp(Boc)-OH, Fmoc-Pro-OH, Fmoc-Ala-OH, Fmoc-Glu (tBu)-OH, Fmoc-Lys(Boc)-OH, Fmoc-Gln(Trt)-OH, Fmoc-Asn(Trt)-OH, Fmoc-Gly-OH, Fmoc-Pro-OH, Fmoc-Asn (Trt)-OH, and Fmoc-Arg(Pbf)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 3

SEQ ID NO: 54

Preparation of Kr1(58-69 Active Zone w Lys Sub Cys)Frag Peptide

The tide compound of Arg Asn Pro Gly Asn Gln Lys Glu Ala Pro Trp Lys (SEQ ID NO: 54) can be prepared using the synthetic sequence described in synthesis example 1 and using Fmoc-Lys(Boc)-OH as the initial amino acid to be attached to the resin. The following amino acids were then sequentially added as follows: Fmoc-Trp(Boc)-OH, Fmoc-Pro-OH, Fmoc-Ala-OH, Fmoc-Glu(tBu)-OH, Fmoc-Lys(Boc)-OH, Fmoc-Gln(Trt)-OH, Fmoc-Asn(Trt)-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 4

SEQ ID NO: 55

Preparation of Kr1(58-68 Active Zone)Frag Peptide

The tide compound of Arg Asn Pro Gly Asn Gln Lys Glu Ala Pro Trp-NH$_2$ (SEQ ID NO: 55) can be prepared using the synthetic sequence described in synthesis example 1 and using Fmoc-Trp(Boc)-OH as the initial amino acid to be attached to the resin. The following amino acids were then sequentially added as follows: Fmoc-Pro-OH, Fmoc-Ala-OH, Fmoc-Glu(tBu)-OH, Fmoc-Lys(Boc)-OH, Fmoc-Gln(Trt)-OH, Fmoc-Asn(Trt)-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 5

SEQ ID NO: 56

Preparation of Kr1(70-81 Active Zone w Lys Sub Cys)Frag Peptide

The tide compound of Phe Thr Leu Asp Glu Asn Phe Lys Ser Asp Leu Lys (SEQ ID NO: 56) can be prepared using the synthetic sequence described in synthesis example 1 and using Fmoc-Lys(Boc)-OH as the initial amino acid to be attached to the resin. The following amino acids were then sequentially added as follows: Fmoc-Leu-OH, Fmoc-Asp(OtBu)-OH, Fmoc-Ser(tBu)-OH, Fmoc-Lys(Boc)-OH, Fmoc-Phe-OH, Fmoc-Asn(Trt)-OH, Fmoc-Glu(tBu)-OH, Fmoc-Asp(OtBu)-OH, Fmoc-Thr(tBu)-OH, and Fmoc-Phe-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 6

SEQ ID NO: 57

Preparation of Kr1(70-80 Active Zone)Frag Peptide

The tide compound of Phe Thr Leu Asp Glu Asn Phe Lys Ser Asp Leu (SEQ ID NO: 57) can be prepared using the synthetic sequence described in synthesis example 1 and using Fmoc-Leu-OH as the initial amino acid to be attached to the resin. The following amino acids were then sequentially added as follows: Fmoc-Asp(OtBu)-OH, Fmoc-Ser(tBu)-OH, Fmoc-Lys(Boc)-OH, Fmoc-Phe-OH, Fmoc-Asn(Trt)-OH, Fmoc-Glu(tBu)-OH, Fmoc-Asp(OtBu)-OH, Fmoc-Thr(tBu)-OH, and Fmoc-Phe-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 7

SEQ ID NO: 58

Preparation of Kr1(71-80 Active Zone)Frag Peptide

The tide compound of Thr Leu Asp Glu Asn Phe Lys Ser Asp Leu-NH$_2$ (SEQ ID NO: 58) can be prepared using the synthetic sequence described in synthesis example 1 and using Fmoc-Leu-OH as the initial amino acid to be attached to the resin. The following amino acids were then sequentially added as follows: Fmoc-Asp(OtBu)-OH, Fmoc-Ser(tBu)-OH, Fmoc-Lys(Boc)-OH, Fmoc-Phe-OH, Fmoc-Asn(Trt)-OH, Fmoc-Glu(tBu)-OH, Fmoc-Asp(OtBu)-OH, and Fmoc-Thr(tBu)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 8

SEQ ID NO: 59

Preparation of Kr1(72-80 Active Zone)Frag Peptide

The tide compound of Leu Asp Glu Asn Phe Lys Ser Asp Leu-NH$_2$ (SEQ ID NO: 59) can be prepared using the synthetic sequence described in synthesis example 1 and using Fmoc-Leu-OH as the initial amino acid to be attached to the resin. The following amino acids were then sequentially added as follows: Fmoc-Asp(OtBu)-OH, Fmoc-Ser(tBu)-OH, Fmoc-Lys(Boc)-OH, Fmoc-Phe-OH, Fmoc-Asn(Trt)-OH, Fmoc-Glu(tBu)-OH, Fmoc-Asp(OtBu)-OH, and Fmoc-Leu-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 9

SEQ ID NO: 60

Preparation of Kr1(73-80 Active Zone)Frag Peptide

The tide compound of Asp Glu Asn Phe Lys Ser Asp Leu-NH$_2$ (SEQ ID NO: 60) can be prepared using the synthetic sequence described in synthesis example 1 and using Fmoc-Leu-OH as the initial amino acid to be attached to the resin. The following amino acids were then sequentially added as follows: Fmoc-Asp(OtBu)-OH, Fmoc-Ser(tBu)-OH, Fmoc-Lys(Boc)-OH, Fmoc-Phe-OH, Fmoc-Asn(Trt)-OH, Fmoc-Glu(tBu)-OH, and Fmoc-Asp(OtBu)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 10

SEQ ID NO: 61

Preparation of Kr1(73-79 Active Zone)Frag Peptide

The tide compound of Asp Glu Asn Phe Lys Ser Asp-NH$_2$ (SEQ ID NO: 61) can be prepared using the synthetic sequence described in synthesis example 1 and using Fmoc-Asp(OtBu)-OH as the initial amino acid to be attached to the resin. The following amino acids were then sequentially added as follows: Fmoc-Ser(tBu)-OH, Fmoc-Lys(Boc)-OH, Fmoc-Phe-OH, Fmoc-Asn(Trt)-OH, Fmoc-Glu(tBu)-OH, and Fmoc-Asp(OtBu)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 11

SEQ ID NO: 63

Preparation of Kr2(56-79 Active Zone w Ala Sub Cys and Lys Sub Cys)Frag Peptide

The tide compound of Arg Asn Pro Gly Gly Gln Met Glu Gly Pro Trp Ala Phe Thr Gln Asn Lys Asn Val Arg Met Glu Leu Lys-NH$_2$ (SEQ ID NO: 63) can be prepared using the synthetic sequence described in synthesis example 1 and using Fmoc-Lys(Boc)-OH as the initial amino acid to be attached to the resin. The following amino acids were then sequentially added as follows: Fmoc-Leu-OH, Fmoc-Glu(tBu)-OH, Fmoc-Met-OH, Fmoc-Arg(Pbf)-OH, Fmoc-Val-OH, Fmoc-Asn(Trt)-OH, Fmoc-Lys(Boc)-OH, Fmoc-Asn(Trt)-OH, Fmoc-Gln(Trt)-OH, Fmoc-Thr(tBu)-OH, Fmoc-Phe-OH, Fmoc-Ala-OH, Fmoc-Trp(Boc)-OH, Fmoc-Pro-OH, Fmoc-Gly-OH, Fmoc-Glu(tBu)-OH, Fmoc-Met-OH, Fmoc-Gln(Trt)-OH, Fmoc-Gly-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 12

SEQ ID NO: 67

Preparation of Kr2(56-78 Active Zone w Ala Sub Cys)Frag Peptide

The tide compound of Arg Asn Pro Gly Gly Gln Met Glu Gly Pro Trp Ala Phe Thr Gln Asn Lys Asn Val Arg Met Glu Leu-NH$_2$ (SEQ ID NO: 67) can be prepared using the synthetic sequence described in synthesis example 1 and using Fmoc-Leu-OH as the initial amino acid to be attached to the resin. The following amino acids were then sequentially added as follows: Fmoc-Glu(tBu)-OH, Fmoc-Met-OH, Fmoc-Arg(Pbf)-OH, Fmoc-Val-OH, Fmoc-Asn(Trt)-OH, Fmoc-Lys(Boc)-OH, Fmoc-Asn(Trt)-OH, Fmoc-Gln(Trt)-OH, Fmoc-Thr(tBu)-OH, Fmoc-Phe-OH, Fmoc-Ala-OH, Fmoc-Trp(Boc)-OH, Fmoc-Pro-OH, Fmoc-Gly-OH, Fmoc-Glu(tBu)-OH, Fmoc-Met-OH, Fmoc-Gln(Trt)-OH, Fmoc-Gly-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 13

SEQ ID NO: 71

Kr2(56-67 Active Zone with Lys Sub Cys)Frag Peptide

The tide compound of Arg Asn Pro Gly Gly Gln Met Glu Gly Pro Trp Lys (SEQ ID NO: 71) can be prepared using the synthetic sequence described in synthesis example 1 and using Fmoc-Lys(Boc)-OH as the initial amino acid to be attached to the resin. The following amino acids were then sequentially added as follows: Fmoc-Trp(Boc)-OH, Fmoc-Pro-OH, Fmoc-Gly-OH, Fmoc-Glu(tBu)-OH, Fmoc-Met-OH, Fmoc-Gln(Trt)-OH, Fmoc-Gly-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 14

SEQ ID NO: 72

Kr2(56-66 Active Zone)Frag Peptide

The tide compound of Arg Asn Pro Gly Gly Gln Met Glu Gly Pro Trp-NH$_2$ (SEQ ID NO: 72) can be prepared using the synthetic sequence described in synthesis example 1 and using Fmoc-Trp(Boc)-OH as the initial amino acid to be attached to the resin. The following amino acids were then sequentially added as follows: Fmoc-Pro-OH, Fmoc-Gly-OH, Fmoc-Glu(tBu)-OH, Fmoc-Met-OH, Fmoc-Gln(Trt)-OH, Fmoc-Gly-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 15

SEQ ID NO: 73

Kr2(68-79 Active Zone w Lys Sub Cys)Frag Peptide

The tide compound of Phe Thr Gln Asn Lys Asn Val Arg Met Glu Leu Lys (SEQ ID NO: 73) can be prepared using the synthetic sequence described in synthesis example 1 and using Fmoc-Lys(Boc)-OH as the initial amino acid to be attached to the resin. The following amino acids were then sequentially added as follows: Fmoc-Leu-OH, Fmoc-Glu(tBu)-OH, Fmoc-Met-OH, Fmoc-Arg(Pbf)-OH, Fmoc-Val-OH, Fmoc-Asn(Trt)-OH, Fmoc-Lys(Boc)-OH, Fmoc-Asn(Trt)-OH, Fmoc-Gln(Trt)-OH, Fmoc-Thr(tBu)-OH, and Fmoc-Phe-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 16

SEQ ID NO: 74

Kr2(68-78 Active Zone)Frag Peptide

The tide compound of Phe Thr Gln Asn Lys Asn Val Arg Met Glu Leu-NH$_2$ (SEQ ID NO: 74) can be prepared using the synthetic sequence described in synthesis example 1 and using Fmoc-Leu-OH as the initial amino acid to be attached to the resin. The following amino acids were then sequentially added as follows: Fmoc-Glu(tBu)-OH, Fmoc-Met-OH, Fmoc-Arg(Pbf)-OH, Fmoc-Val-OH, Fmoc-Asn(Trt)-OH, Fmoc-Lys(Boc)-OH, Fmoc-Asn(Trt)-OH, Fmoc-Gln(Trt)-OH, Fmoc-Thr(tBu)-OH, and Fmoc-Phe-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 17

SEQ ID NO: 75

Kr2(69-78Active Zone)Frag Peptide

The tide compound of Thr Gln Asn Lys Asn Val Arg Met Glu Leu-NH$_2$ (SEQ ID NO: 75) can be prepared using the synthetic sequence described in synthesis example 1 and using Fmoc-Leu-OH as the initial amino acid to be attached to the resin. The following amino acids were then sequentially added as follows: Fmoc-Glu(tBu)-OH, Fmoc-Met-OH, Fmoc-Arg(Pbf)-OH, Fmoc-Val-OH, Fmoc-Asn(Trt)-OH, Fmoc-Lys(Boc)-OH, Fmoc-Asn(Trt)-OH, Fmoc-Gln(Trt)-OH, and Fmoc-Thr(tBu)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 18

SEQ ID NO: 76

Kr2(70-78 Active Zone)Frag Peptide

The tide compound of Gln Asn Lys Asn Val Arg Met Glu Leu-NH$_2$ (SEQ ID NO: 76) can be prepared using the synthetic sequence described in synthesis example 1 and using Fmoc-Leu-OH as the initial amino acid to be attached to the resin. The following amino acids were then sequentially added as follows: Fmoc-Glu(tBu)-OH, Fmoc-Met-OH, Fmoc-Arg(Pbf)-OH, Fmoc-Val-OH, Fmoc-Asn(Trt)-OH, Fmoc-Lys(Boc)-OH, Fmoc-Asn(Trt)-OH, and Fmoc-Gln(Trt)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 19

SEQ ID NO: 77

Kr2(70-77 Active Zone)Frag Peptide

The tide compound of Gln Asn Lys Asn Val Arg Met Glu-NH$_2$ (SEQ ID NO: 77) can be prepared using the synthetic sequence described in synthesis example 1 and using Fmoc-Glu(tBu)-OH as the initial amino acid to be attached to the resin. The following amino acids were then sequentially added as follows: Fmoc-Met-OH, Fmoc-Arg(Pbf)-OH, Fmoc-Val-OH, Fmoc-Asn(Trt)-OH, Fmoc-Lys(Boc)-OH, Fmoc-Asn(Trt)-OH, and Fmoc-Gln(Trt)-OH. The Fmoc group at the N-terminal can then be deblocked using 20% piperidine in DMF for at least up to 15 minutes. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 20

SEQ ID NO: 78

Mod-Kr1(58-81 Active Zone w Ala Sub Cys and w Lys Sub Cys)Frag Peptide

The tide compound of NAc Arg Asn Pro Gly Asn Gln Lys Glu Ala Pro Trp Ala Phe Thr Leu Asp Glu Asn Phe Lys Ser Asp Leu Lys (SEQ ID NO: 78) can be prepared using the synthetic sequence as outlined in synthesis example 1 using Fmoc-Lys-OH as the initial amino acid to be attached to the resin. The following amino acids were then sequentially added as follows: Fmoc-Leu-OH, Fmoc-Asp(OtBu)-OH, Fmoc-Ser(tBu)-OH, Fmoc-Lys(Boc)-OH, Fmoc-Phe-OH, Fmoc-Asn(Trt)-OH, Fmoc-Glu(tBu)-OH, Fmoc-Asp (OtBu)-OH, Fmoc-Leu-OH, Fmoc-Thr(tBu)-OH, Fmoc-Phe-OH, Fmoc-Ala-OH, Fmoc-Trp(Boc)-OH, Fmoc-Pro-OH, Fmoc-Ala-OH, Fmoc-Glu(tBu)-OH, Fmoc-Lys(Boc)-OH, Fmoc-Gln(Trt)-OH, Fmoc-Asn(Trt)-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes. Coupling acetic acid (HOAc) to make the amide (NAc) can be formed under similar conditions to amino acid coupling. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 21

SEQ ID NO: 106

NAc Mod-Kr1(58-69 Active Zone w Lys Sub Cys)Frag Peptide

The tide compound of NAc Arg Asn Pro Gly Asn Gln Lys Glu Ala Pro Trp Lys (SEQ ID NO: 106) can be prepared using the synthetic sequence as outlined in synthesis example 1 using Fmoc-Lys-OH as the initial amino acid to be attached to the resin. The following amino acids were then sequentially added as follows: Fmoc-Trp(Boc)-OH, Fmoc-Pro-OH, Fmoc-Ala-OH, Fmoc-Glu(tBu)-OH, Fmoc-Lys(Boc)-OH, Fmoc-Gln(Trt)-OH, Fmoc-Asn(Trt)-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes. Coupling acetic acid (HOAc) to make the amide (NAc) can be formed under similar conditions to amino acid coupling. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 22

SEQ ID NO: 107

MPA Mod-Kr1(58-69 Active Zone w Lys Sub Cys)Frag Peptide

The tide compound of MPA Arg Asn Pro Gly Asn Gln Lys Glu Ala Pro Trp Lys (SEQ ID NO: 107) can be prepared using the synthetic sequence as outlined in synthesis example 1 using Fmoc-Lys-OH as the initial amino acid to be attached to the resin. The following amino acids were then sequentially added as follows: Fmoc-Trp(Boc)-OH, Fmoc-Pro-OH, Fmoc-Ala-OH, Fmoc-Glu(tBu)-OH, Fmoc-Lys(Boc)-OH, Fmoc-Gln(Trt)-OH, Fmoc-Asn(Trt)-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes followed by coupling of 3-MPA. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 23

SEQ ID NO: 108

MPA-AEEA Mod-Kr1(58-69 Active Zone w Lys Sub Cys)Frag Peptide

The tide compound of MPA-AEEA Arg Asn Pro Gly Asn Gln Lys Glu Ala Pro Trp Lys (SEQ ID NO: 108) can be prepared using the synthetic sequence as outlined in synthesis example 1 using Fmoc-Lys-OH as the initial amino acid to be attached to the resin. The following amino acids were then sequentially added as follows: Fmoc-Trp(Boc)-OH, Fmoc-Pro-OH, Fmoc-Ala-OH, Fmoc-Glu(tBu)-OH, Fmoc-Lys(Boc)-OH, Fmoc-Gln(Trt)-OH, Fmoc-Asn(Trt)-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes followed by coupling of Fmoc-AEEA. Cleavage of the completed peptide from the resin can then be achieved using the cleavage mixture as above in synthesis example 1. The peptide product can then be purified by reverse phase HPLC and precipitated to yield a while solid upon lyophilization.

Synthesis Example 24

SEQ ID NO: 109

NAc Nε-MPA Mod-Kr1(58-69 Active Zone w Lys Sub Cys)Frag Peptide

The tide compound of NAc-Arg Asn Pro Gly Asn Gln Lys Glu Ala Pro Trp Lys-Nε-MPA (SEQ ID NO: 109) can be prepared using the synthetic sequence as outlined in synthesis example 1 using Fmoc-Lys(Aloc)-OH as the initial amino acid to be attached to the resin. The selective deblocking of the Lys(Aloc) group is preferably performed manually by treating the resin with a solution of about a three fold equivalent excess of Pd(PPh$_3$)$_4$ solvated in CHCl$_3$:NMM:HOAc (19:1:0.5) for about 2 hours. The resin can then be washed for about 6 times with CHCl$_3$, then washed with about 20% HOAc in DCM for about 6 times, and then washed with DMF for about 6 times. Afterwards the synthesis can then be automated for the addition of 3-maleimidopropionic acid. The following amino acids were then sequentially added as follows: Fmoc-Trp(Boc)-OH, Fmoc-Pro-OH, Fmoc-Ala-OH, Fmoc-Glu(tBu)-OH, Fmoc-Lys(Boc)-OH, Fmoc-Gln(Trt)-OH, Fmoc-Asn(Trt)-OH, Fmoc-Gly-OH, Fmoc-Pro-OH, Fmoc-Asn(Trt)-OH, and Fmoc-Arg(Pbf)-OH. The Fmoc group at the N-terminal can then be deblocked using 20% piperidine in DMF for at least up to 15 minutes. Coupling acetic acid (HOAc) to make the amide (NAc) can be formed under similar conditions to amino acid coupling. Cleavage of the completed peptide from the resin can then be achieved using the cleavage mixture as above in synthesis example 1. The peptide product can then be purified by reverse phase HPLC and precipitated to yield a while solid upon lyophilization.

While the invention has been described in connection with specific embodiments thereof, it will be understood that

What is claimed is:

1. An anticancer agent comprising:
   a GRP78 antagonist or a pharmaceutically acceptable salt;
   wherein the GRP78 antagonist is a plasminogen kringle 5 fragment attached to immunoglobulin;
   wherein the plasminogen kringle 5 fragment attached to immunoglobulin is selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and combinations thereof.

2. An anticancer agent comprising:
   a GRP78 antagonist or a pharmaceutically acceptable salt;
   wherein the GRP78 antagonist is an ROR1 kringle fragment attached to immunoglobulin;
   wherein the ROR1 kringle fragment attached to immunoglobulin is selected from the group consisting of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, and combinations thereof.

3. An anticancer agent comprising:
   a GRP78 antagonist or a pharmaceutically acceptable salt;
   wherein the GRP78 antagonist is an ROR2 kringle fragment attached to immunoglobulin;
   wherein the ROR2 kringle fragment attached to immunoglobulin is selected from the group consisting of SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, and combinations thereof.

\* \* \* \* \*